(12) United States Patent
Modlin et al.

(10) Patent No.: US 11,744,907 B2
(45) Date of Patent: Sep. 5, 2023

(54) PREDICTING PEPTIDE RECEPTOR RADIOTHERAPY USING A GENE EXPRESSION ASSAY

(71) Applicant: Liquid Biopsy Research LLC, Charlestown (KN)

(72) Inventors: Irvin Mark Modlin, Woodbridge, CT (US); Mark Kidd, New Haven, CT (US); Ignat Drozdov, Warwick (GB)

(73) Assignee: Liquid Biopsy Research LLC, Charlestown (KN)

( * ) Notice: Subject to any disclaimer, the term of this patent is extended or adjusted under 35 U.S.C. 154(b) by 1134 days.

(21) Appl. No.: 16/203,803

(22) Filed: Nov. 29, 2018

(65) Prior Publication Data

US 2019/0160189 A1    May 30, 2019

Related U.S. Application Data

(60) Provisional application No. 62/592,647, filed on Nov. 30, 2017.

(51) Int. Cl.

| | |
|---|---|
| *C12Q 1/68* | (2018.01) |
| *A61K 51/08* | (2006.01) |
| *C12Q 1/6837* | (2018.01) |
| *G16B 25/10* | (2019.01) |
| *C12Q 1/6874* | (2018.01) |
| *C12Q 1/6806* | (2018.01) |
| *C12Q 1/686* | (2018.01) |
| *C12Q 1/6853* | (2018.01) |
| *A61P 35/00* | (2006.01) |
| *C12Q 1/6886* | (2018.01) |

(52) U.S. Cl.
CPC .......... *A61K 51/088* (2013.01); *A61P 35/00* (2018.01); *C12Q 1/686* (2013.01); *C12Q 1/6806* (2013.01); *C12Q 1/6837* (2013.01); *C12Q 1/6853* (2013.01); *C12Q 1/6874* (2013.01); *C12Q 1/6886* (2013.01); *G16B 25/10* (2019.02); *C12Q 2600/106* (2013.01); *C12Q 2600/158* (2013.01)

(58) Field of Classification Search
None
See application file for complete search history.

(56) References Cited

U.S. PATENT DOCUMENTS

| 10,407,730 B2 | 9/2019 | Modlin et al. |
| 11,168,372 B2 | 11/2021 | Modlin et al. |
| 2016/0076106 A1* | 3/2016 | Modlin ............ G01N 33/57407 424/1.69 |

FOREIGN PATENT DOCUMENTS

| JP | 2014512172 A | 5/2014 |
| JP | 2017528164 A | 9/2017 |
| WO | WO-2012119013 A1 | 9/2012 |
| WO | WO-2016044330 A1 | 3/2016 |
| WO | WO-2019108734 A1 | 6/2019 |

OTHER PUBLICATIONS

Bodei et al; Eur J. Nucl Med Mol Imaging, vol. 43, pp. 839-851, Nov. 2015.*
Kidd etal; Endoc Relat Cancer, vol. 22, pp. 561-575, 2015.*
Ballman, K. V. (2015) "Biomarker: Predictive or Prognostic?" *J Clin Oncol*, 33:3968-3971.
Blaickner, M. (2014) "Relevance of PET for pretherapeutic prediction of doses in peptide receptor radionuclide therapy" *PET Clin*, 9:99-112.
Bodei, L. et al. (2016) "Measurement of circulating transcripts and gene cluster analysis predicts and defines therapeutic efficacy of peptide receptor radionuclide therapy (PRRT) in neuroendocrine tumors" *Eur J Nucl Med Mol Imaging*, 43:839-851.
Bodei, L. et al. (2016) "Radiolabeled Somatostatin Analogue Therapy of Gastroenteropancreatic Cancer" *Semin Nucl Med*, 46:225-238.
Brabander, T. et al. (2017) "Long-Term Efficacy, Survival, and Safety of [$^{177}$Lu-DOTA$^O$,Tyr$^3$]octreotate in Patients with Gastroenteropancreatic and Bronchial Neuroendocrine Tumors" *Clin Cancer Res*, 23:4617-4624.
Califano, A. et al. (2017) "The recurrent architecture of tumour initiation, progression and drug sensitivity" *Nat Rev Cancer*, 17:116-130.
Charoenpitakchai, M. et al. (2017) "In liver metastases from small intestinal neuroendocrine tumors, SSTR2A expression is heterogeneous" *Virchows Arch*, 470:545-552.
Cives, M. and Strosberg. J. (2017) "Radionuclide Therapy for Neuroendocrine Tumors" *Curr Oncol Rep*, 19:9; 9 pages.
Ezziddin, S. et al. (2014) "Outcome of peptide receptor radionuclide therapy with $^{177}$Lu-octreotate in advanced grade 1/2 pancreatic neuroendocrine tumours" Eur *J Nucl Med Mol Imaging*, 41:925-933.
Ezziddin, S. et al. (2014) "Predictors of long-term outcome in patients with well-differentiated gastroenteropancreatic neuroendocrine tumors after peptide receptor radionuclide therapy with $^{177}$Lu-octreotate" *J Nucl Med*, 55:183-190.
Gabriel, M. et al. (2009) "$^{68}$Ga-DOTA-Tyr$^3$-Octreotide PET for Assessing Response to Somatostatin-Receptor-Mediated Radionuclide Therapy" *J Nucl Med*, 50:1427-1434.
Genbank Accession No. NM_001654 (Oct. 21, 2018) "Homo sapiens A-Raf proto-oncogene, serine/threonine kinase (ARAF), transcript variant 1, mRNA" National Center for Biotechnology Information (NCBI) [online]. Retrieved from: https://www.ncbi.nlm.nih.gov/nuccore/NM_001654.4; retrieved on Feb. 7, 2019, 5 pages.

(Continued)

*Primary Examiner* — Jehanne S Sitton
(74) *Attorney, Agent, or Firm* — COOLEY LLP; Ivor R. Elrifi; Matthew Pavao

(57) ABSTRACT

The present invention is directed to methods for providing a peptide receptor radiotherapy treatment recommendation for a subject having a neuroendocrine tumor by determining the expression level of each of at least 9 biomarkers comprising ARAF1, BRAF, KRAS, RAF-1, ATP6V1H, OAZ2, PANK2, PLD3, and ALG9. In some embodiments, the methods can further include determining the expression level of each of NAP1L1, NOL3, and TECPR2.

11 Claims, 10 Drawing Sheets

Specification includes a Sequence Listing.

(56) References Cited

OTHER PUBLICATIONS

Genbank Accession No. NM_002537 (Dec. 16, 2018) "Homo sapiens ornithine decarboxylase antizyme 2 (OAZ2), transcript variant 1, mRNA" National Center for Biotechnology Information (NCBI) [online]. Retrieved from: https://www.ncbi.nlm.nih.gov/nuccore/NM_002537.3; retrieved on Feb. 7, 2019, 4 pages.
Genbank Accession No. NM_002880 (Jan. 1, 20193) "Homo sapiens Raf-1 proto-oncogene, serine/threonine kinase (RAFI), transcript variant 2, mRNA" National Center for Biotechnology Information (NCBI) [online], Retrieved from: https://www.ncbi.nlm.nih.gov/nuccore/NM_002880.3; retrieved on Feb. 7, 2019, 7 pages.
Genbank Accession No. NM_004333 (Jul. 1, 20177) "Homo sapiens B-Raf proto-oncogene, serine/threonine kinase (BRAF), mRNA" National Center for Biotechnology Information (NCBI) [online]. Retrieved from: https://www.ncbi.nlm.nih.gov/nuccore/NM_004333.4; retrieved on Feb. 7, 2019, 6 pages.
Genbank Accession No. NM_004985 (Feb. 3, 2019) "Homo sapiens KRAS proto-oncogene, GTPase (KRAS), transcript variant b, mRNA" National Center for Biotechnology Information (NCBI) [online]. Retrieved from: https://www.ncbi.nlm.nih.gov/nuccore/NM_004985.4; retrieved on Feb. 7, 2019, 6 pages.
Genbank Accession No. NM_015941 (Nov. 2, 20182) "Homo sapiens ATPase H+ transporting V1 subunit H (ATP6V1H), transcript variant 1, mRNA" National Center for Biotechnology Information (NCBI) [online]. Retrieved from: https://www.ncbi.nlm.nih.gov/nuccore/NM_015941; retrieved on Feb. 7, 2019, 4 pages.
Genbank Accession No. NM_024740 (Jan. 21, 2019) "Homo sapiens ALG9 alpha-1,2-mannosyltransferase (ALG9), transcript variant 1, mRNA" National Center for Biotechnology Information (NCBI) [online]. Retrieved from: https://www.ncbi.nlm.nih.gov/nuccore/NM_024740; retrieved on Feb. 7, 2019, 6 pages.
Genbank Accession No. NM_024960 (Dec. 12, 2019) "Homo sapiens pantothenate kinase 2 (PANK2), transcript variant 3, mRNA" National Center for Biotechnology Information (NCBI) [online]. Retrieved from: https://www.ncbi.nlm.nih.gov/nuccore/NM_024960.4; retrieved on Feb. 7, 2019, 4 pages.
Genbank Accession No. NM_139207 (Mar. 15, 2015) "Homo sapiens nucleosome assembly protein 1 like 1 (NAP1L1), transcript variant 1, mRNA" National Center for Biotechnology Information (NCBI) [online]. Retrieved from: https://www.ncbi.nlm.nih.gov/nuccore/NM_13 9207.2; retrieved on Feb. 7, 2019, 5 pages.
Genbank Accession No. NM_001031696 (Jan. 12, 2019) "Homo sapiens phospholipase D family member 3 (PLD3), transcript variant 1, mRNA" National Center for Biotechnology Information (NCBI) [online]. Retrieved from: https://www.ncbi.nlm.nih.gov/nuccore/NM_001031696,3; retrieved on Feb. 7, 2019, 4 pages.
Genbank Accession No. NM_001172631 (Dec. 16, 2018) "Homo sapiens tectonin beta-propeller repeat containing 2 (TECPR2), transcript variant 2, mRNA" National Center for Biotechnology Information (NCBI) [online]. Retrieved from: https://www.ncbi.nlm.nih.gov/nuccore/NM_001172631; retrieved on Feb. 7, 2019, 6 pages.
Genbank Accession No. NM_001185057 (Jul. 22, 2018) "Homo sapiens nucleolar protein 3 (NOL3), transcript variant 3, mRNA" National Center for Biotechnology Information (NCBI) [online]. Retrieved from: https://www.ncbi.nlm.nih.gov/nuccore/NM_001185057; retrieved on Feb. 7, 2019, 4 pages.
Kaijser, J. et al. (2014) "Presurgical diagnosis of adnexal tumours using mathematical models and scoring systems: a systematic review and meta-analysis" *Hum Reprod Update*, 20:449-462.
Kidd, M. (2015) "Blood and tissue nemoendocrine tumor gene cluster analysis correlate, define hallmarks and predict disease status" *Endocr Relat Cancer*, 22:561-575.
Kwekkeboom, D.J. et al. (2010) "Somatostatin-receptor-based imaging and therapy of gastroenteropancreatic neuroendocrine tumors" *Endocr Relat Cancer*, 17:R53-R73.

Li, S.C. et al. (2013) "Global microRNA profiling of well-differentiated small intestinal nemoendocrine tumors" *Mod Pathol*, 26:685-696.
Li, X.J. et al. (2013) A blood-based proteomic classifier for the molecular characterization of pulmonary nodules. Sci Transl Med, 5: 207ra142.
Mariniello, A. et al. (2016) "Long-term results of PRRT in advanced bronchopulmonary carcinoid" *Eur J Nucl Med Mol Imaging*, 43:441-452.
Modlin, I.M. (2013) "The identification of gut neuroendocrine tumor disease by multiple synchronous transcript analysis in blood" *PLOS One*, 8(5):e63364, 12 pages.
Modlin, I.M. et al. (2014) "A multianalyte PCR blood test outperforms single analyte ELISAs (chromogranin A, pancreastatin, neurokinin A) for neuroendocrine tumor detection" *Endocr Relat Cancer*, 21:615-628.
Oberg, K. et al. (2016) "A Delphic consensus assessment: imaging and biomarkers in gastroenteropancreatic nemoendocrine tumor disease management" *Endocr Connect*, 5:174-187.
Oksuz, M.O. et al. (2014) "Peptide receptor radionuclide therapy of nemoendocrine tumors with $^{90}$Y-DOTATOC: Is treatment response predictable by pre-therapeutic uptake of $^{68}$Ga-DOTATOC?" *Diagn Interv Imaging*, 95:289-300.
Oxnard, G.R. et al. (2014) "Noninvasive detection of response and resistance in EGFR-mutant lung cancer using quantitative next-generation genotyping of cell-free plasma DNA" *Clin Cancer Res*, 20:1698-1705.
Pritzker, K.P. (2015) "Predictive and prognostic cancer biomarkers revisited" *Expert Rev Mol Diagn*, 15:971-974.
Reubi, J.C. et al. (1994) "Expression of somatostatin receptors in normal, inflamed, and neoplastic human gastrointestinal tissues" *Ann NY Acad Sci*, 733:122-137.
Risch, H.A. et al. (2017) "Aspirin Use and Reduced Risk of Pancreatic Cancer" Cancer *Epidemiol Biomarkers Prev*, 26:68-74.
Sansovini, M. et al. (2013) "Treatment with the radiolabelled somatostatin analog $^{177}$Lu-DOTATATE for advanced pancreatic neuroendocrine tumors" *Neuroendocrinology*, 97:347-354.
Strosberg, J. et al. (2017) "Phase 3 Trial of $^{177}$Lu-Dotatate for Midgut Neuroendocrine Tumors" *N Engl J Med*, 376:125-135.
Thang, S.P. et al. (2017) "Peptide receptor radionuclide therapy (PRRT) in European Nemoendocrine Tumour Society (ENETS) grade 3 (G3) neuroendocrine neoplasia (NEN)—a single-institution retrospective analysis" *Eur J Nucl Med Mol Imaging*, 45:262-277.
Trusheim, M.R. (2015) "The clinical benefits, ethics, and economics of stratified medicine and companion diagnostics" *Drug Discov Today*, 20:1439-1450.
Walenkamp, A. et al. (2014) "Hallmarks of gastrointestinal nemoendocrine tumours: implications for treatment" *Endocr Relat Cancer*, 21:R445-R460.
Wang, E. (2015) "Predictive genomics: A cancer hallmark network framework for predicting tumor clinical phenotypes using genome sequencing data" *Semin Cancer Biol*, 30:4-12.
Yang, Z. (2011) "Effect of Tumor Heterogeneity on the Assessment of Ki67 Labeling Index in Well-differentiated Neuroendocrine Tumors Metastatic to the Liver: Implications for Prognostic Stratification" *Am J Surg Pathol*, 35:853-860.
Cwikla, J.B. et al. (2015) "Circulating Transcript Analysis (NETest) in GEP-NETs Treated With Somatostatin Analogs Defines Therapy" J Clin Endocrinol Metab, 100(11):E1437-E1445.
Mcveigh, T.P. et al. (2017) "Clinical use of the Oncotype DX genomic test to guide treatment decisions for patients with invasive breast cancer", Breast Cancer—Targets and Therapy, 9:393-400.
Modlin, I. et al. (2006) "The functional characterization of normal and neoplastic human enterochromaffin cells", J Clin Endocrinol Metab, 91(6):2340-2348.
Modlin, I. et al. (2013) "The Identification of gut neuroendocrine tumor disease by multiple synchronous transcript analysis in blood", Plos One, vol. 8, Issue 5, e63364, Supplementary Methods, 27 pages.
Modlin, I.M. et al. (Jan. 2016) "Blood measurement of neuroendocrine gene transcripts defines the effectiveness of operative resection and ablation strategies" Surgery, 159:336-347.

(56) References Cited

OTHER PUBLICATIONS

Schimmack et al. (May 15, 2012) "The Clinical Implications and Biologic Relevance of Neurofilament Expression in Gastroenteropancreatic Neuroendocrine Neoplasms", Cancer, 118(10):2763-2775.

Zikusoka, M.N. et al. (2005) "Molecular genetics of gastroenteropancreatic neuroendocrine tumors", Cancer, 104:2292-2309.

* cited by examiner

SEQUENCE LISTING

<160> NUMBER OF SEQ ID NOS: 12

<210> SEQ ID NO 1
<211> LENGTH: 2562
<212> TYPE: DNA
<213> ORGANISM: Homo sapiens

<400> SEQUENCE: 1
cttgacagac gtgaccctga cccaataagg gtggaaggct gagtcccgca gagccaataa      60
cgagagtccg agaggcgacg gaggcggact ctgtgaggaa acaagaagag aggcccaaga     120

```
tggagacggc ggcggctgta gcggcgtgac aggagcccca tggcacctgc ccagccccac    180
ctcagcccat cttgacaaaa tctaaggctc catggagcca ccacggggcc ccctgccaa     240 tggggccgag ccatcccggg cagtgggcac cgtcaaagta tacctgccca caagcaacg    300 cacggtggtg actgtccggg atggcatgag tgtctacgac tctctagaca aggccctgaa   360 ggtgcgggt ctaaatcagg actgctgtgt ggtctaccga ctcatcaagg gacgaaagac    420
ggtcactgcc tggacacag ccattgctcc cctggatggc gaggagctca ttgtcgaggt    480
ccttgaagat gtcccgctga ccatgcacaa ttttgtacgg aagaccttct tcagcctggc   540
gttctgtgac ttctgcctta gtttctgtt ccatggcttc cgttgccaaa cctgtggcta    600
caagttccac cagcattgtt cctccaaggt ccccacagtc tgtgttgaca tgagtaccaa   660
ccgccaacag ttctaccaca gtgtccagga tttgtccgga ggctccagac agcatgaggc   720
tccctcgaac cgcccctga atgagttgct aaccccccag ggtcccagcc ccgcaccca    780 gcactgtgac ccggagcact tcccttccc tgcccagcc aatgccccc tacagcgcat     840 ccgctccacg tccactccca acgtccatat ggtcagcacc acggccccca tggactccaa   900
cctcatccag ctcactggcc agagtttcag cactgatgct gccggtagta gaggaggtag   960
tgatggaacc ccccggggga gccccagccc agccagcgtg tcctcgggga ggaagtcccc   1020
acattccaag tcaccagcag agcagcgcga gcggaagtcc ttggccgatg acaagaagaa   1080
agtgaagaac ctggggtacc gggactcagg ctattactgg gaggtaccac ccagtgaggt   1140
gcagctgctg aagaggatcg ggacgggctc gtttggcacc gtgtttcgag ggcggtggca   1200
tggcgatgtg gccgtgaagg tgctcaaggt gtcccagccc acagctgagc aggcccaggc   1260
tttcaagaat gagatgcagg tgctcaggaa gacgcgacat gtcaacatct tgctgtttat   1320
gggcttcatg acccggccgg gatttgccat catcacacag tggtgtgagg ctccagcct    1380 ctaccatcac ctgcatgtgg ccgacacacg cttcgacatg gtccagctca tcgacgtggc   1440
ccggcagact gcccagggca tggactacct ccatgccaag aacatcatcc accgagatct   1500
caagtctaac aacatcttcc tacatgaggg gctcacggtg aagatcggtg actttggctt   1560
ggccacagtg aagactcgat ggagcggggc ccagccttg gagcagccct caggatctgt    1620
gctgtggatg cagctgagg tgatccgtat gcaggacccg aaccctaca gcttccagtc    1680 agacgtctat gcctacgggg ttgtgctcta cgagcttatg actggctcac tgccttacag   1740
ccacattggc tgccgtgacc agattatctt tatggtgggc cgtggctatc tgtccccgga   1800
cctcagcaaa atctccagca actgccccaa ggccatgcgg cgcctgctgt ctgactgcct   1860
caagttccag cggaggagc ggcccctctt ccccagatc ctggccacaa ttgagctgct    1920
gcaacggtca ctccccaaga ttgagcggag tgcctcggaa ccctccttgc accgcaccca   1980
ggccgatgag ttgcctgcct gcctactcag cgcagcccgc cttgtgcctt aggccccgcc   2040
caagccacca gggagccaat ctcagccctc cacgccaagg agccttgccc accagccaat   2100
caatgttcgt ctctgccctg atgctgcctc aggatccccc attccccacc ctgggagatg   2160 aggggtccc catgtgcttt tccagttctt ctggaattgg ggaccccg ccaaagactg     2220 agccccctgt ctcctccatc atttggtttc ctcttggctt tggggatact tctaaatttt   2280
gggagctcct ccatctccaa tggctgggat tgtggcagg gattccactc agaacctctc    2340
tggaatttgt gcctgatgtg ccttccactg gatttgggg ttcccagcac cccatgtgga    2400
ttttgggggg tccctttgt gtctcccccg ccattcaagg actcctctct ttcttcacca    2460
```

-continued

| | |
|---|---:|
| agaagcacag aattctgctg ggcctttgct tgtttaaaaa aaaaaaaaaa aaaaaaaaaa | 2520 |
| aaaaaaaaaa aaaaaaaaaa aaaaaaaaaa aaaaaaaaaa aa | 2562 |

<210> SEQ ID NO 2
<211> LENGTH: 2949
<212> TYPE: DNA
<213> ORGANISM: Homo sapiens

<400> SEQUENCE: 2

| | |
|---|---:|
| cgcctccctt cccctcccc gcccgacagc ggccgctcgg ccccggctc tcggttataa | 60 |
| gatggcggcg ctgagcggtg gcggtggtgg cggcgcggag ccgggccagg ctctgttcaa | 120 |
| cggggacatg gagcccgagg ccggcgccgg cgccggcgcc gcggcctctt cggctgcgga | 180 |
| ccctgccatt ccgaggagg tgtggaatat caaacaaatg attaagttga cacaggaaca | 240 |
| tatagaggcc ctattggaca aatttggtgg ggagcataat ccaccatcaa tatatctgga | 300 |
| ggcctatgaa gaatacacca gcaagctaga tgcactccaa caaagagaac aacagttatt | 360 |
| ggaatctctg gggaacggaa ctgattttc tgtttctagc tctgcatcaa tggataccgt | 420 |
| tacatcttct cctcttcta gcctttcagt gctaccttca tctctttcag ttttcaaaa | 480 |
| tcccacagat gtggcacgga gcaaccccaa gtcaccacaa aaacctatcg ttagagtctt | 540 |
| cctgcccaac aaacagagga cagtggtacc tgcaaggtgt ggagttacag tccgagacag | 600 |
| tctaaagaaa gcactgatga tgagaggtct aatcccagag tgctgtgctg tttacagaat | 660 |
| tcaggatgga gagaagaaac caattggttg ggacactgat atttcctggc ttactggaga | 720 |
| agaattgcat gtggaagtgt tggagaatgt tccacttaca acacacaact ttgtacgaaa | 780 |
| aacgttttc accttagcat tttgtgactt ttgtcgaaag ctgcttttcc agggtttccg | 840 |
| ctgtcaaaca tgtggttata aatttcacca gcgttgtagt acagaagttc cactgatgtg | 900 |
| tgttaattat gaccaacttg atttgctgtt tgtctccaag ttctttgaac caccccaat | 960 |
| accacaggaa gaggcgtcct tagcagagac tgccctaaca tctggatcat ccccttccgc | 1020 |
| acccgcctcg gactctattg gccccaaat tctcaccagt ccgtctcctt caaaatccat | 1080 |
| tccaattcca cagcccttcc gaccagcaga tgaagatcat cgaaatcaat ttgggcaacg | 1140 |
| agaccgatcc tcatcagctc ccaatgtgca tataaacaca atagaacctg tcaatattga | 1200 |
| tgacttgatt agagaccaag gatttcgtgg tgatggagga tcaaccacag gtttgtctgc | 1260 |
| tacccccct gcctcattac ctggctcact aactaacgtg aaagccttac agaaatctcc | 1320 |
| aggacctcag cgagaaagga agtcatcttc atcctcagaa acaggaatc gaatgaaaac | 1380 |
| acttggtaga cgggactcga gtgatgattg ggagattcct gatgggcaga ttacagtggg | 1440 |
| acaaagaatt ggatctggat catttggaac agtctacaag ggaaagtggc atggtgatgt | 1500 |
| ggcagtgaaa atgttgaatg tgacagcacc tacacctcag cagttacaag ccttcaaaaa | 1560 |
| tgaagtagga gtactcagga aaacacgaca tgtgaatatc ctactcttca tgggctattc | 1620 |
| cacaaagcca caactggcta ttgttaccca gtggtgtgag ggctccagct tgtatcacca | 1680 |
| tctccatatc attgagacca aatttgagat gatcaaactt atagatattg cacgacagac | 1740 |
| tgcacagggc atggattact acacgccaa gtcaatcatc cacagagacc tcaagagtaa | 1800 |
| taatatattt cttcatgaag acctcacagt aaaaataggt gattttggtc tagctacagt | 1860 |
| gaaatctcga tggagtgggt cccatcagtt tgaacagttg tctggatcca ttttgtggat | 1920 |
| ggcaccagaa gtcatcagaa tgcaagataa aaatccatac agctttcagt cagatgtata | 1980 |

```
tgcatttgga attgttctgt atgaattgat gactggacag ttaccttatt caaacatcaa    2040
caacagggac cagataattt ttatggtggg acgaggatac ctgtctccag atctcagtaa    2100
ggtacggagt aactgtccaa aagccatgaa gagattaatg gcagagtgcc tcaaaaagaa    2160
aagagatgag agaccactct ttccccaaat tctcgcctct attgagctgc tggcccgctc    2220
attgccaaaa attcaccgca gtgcatcaga accctccttg aatcgggctg gtttccaaac    2280
agaggatttt agtctatatg cttgtgcttc tccaaaaaca cccatccagg caggggata    2340 tggtgcgttt cctgtccact gaaacaaatg agtgagagag ttcaggagag tagcaacaaa    2400
aggaaaataa atgaacatat gtttgcttat atgttaaatt gaataaaata ctctcttttt    2460
ttttaaggtg aaccaaagaa cacttgtgtg gttaaagact agatataatt tttccccaaa    2520
ctaaaattta tacttaacat tggatttta acatccaagg gttaaaatac atagacattg    2580
ctaaaaattg gcagagcctc ttctagaggc tttactttct gttccgggtt tgtatcattc    2640
acttggttat tttaagtagt aaacttcagt ttctcatgca actttttgttg ccagctatca    2700 catgtccact agggactcca gaagaagacc ctacctatgc ctgtgtttgc aggtgagaag    2760
ttggcagtcg gttagcctgg gttagataag gcaaactgaa cagatctaat ttaggaagtc    2820
agtagaattt aataattcta ttattattct taataatttt tctataacta tttcttttta    2880
taacaatttg gaaaatgtgg atgtctttta tttccttgaa gcaataaact aagtttcttt    2940
ttataaaaa                                                            2949

<210> SEQ ID NO 3
<211> LENGTH: 5765
<212> TYPE: DNA
<213> ORGANISM: Homo sapiens

<400> SEQUENCE: 3
tcctaggcgg cggccgcggc ggcggaggca gcagcggcgg cggcagtggc ggcggcgaag      60
gtggcggcgg ctcggccagt actcccggcc cccgccattt cggactggga gcagcgcgg     120 cgcaggcact gaaggcggcg gcggggccag aggctcagcg gctcccaggt gcgggagaga     180
ggcctgctga aaatgactga atataaactt gtggtagttg gagctggtgg cgtaggcaag     240
agtgccttga cgatacagct aattcagaat cattttgtgg acgaatatga tccaacaata     300
gaggattcct acaggaagca agtagtaatt gatggagaaa cctgtctctt ggatattctc     360
gacacagcag gtcaagagga gtacagtgca atgagggacc agtacatgag gactggggag     420 ggctttctt gtgtatttgc cataaataat actaaatcat ttgaagatat tcaccattat     480
agagaacaaa ttaaaagagt taaggactct gaagatgtac ctatggtcct agtaggaaat     540
aaatgtgatt tgccttctag aacagtagac acaaaacagg ctcaggactt agcaagaagt     600
tatggaattc ctttttattga aacatcagca aagacaagac agggtgttga tgatgccttc     660
tatacattag ttcgagaaat tcgaaaacat aaagaaaaga tgagcaaaga tggtaaaaag     720
aagaaaaaga agtcaaagac aaagtgtgta attatgtaaa tacaatttgt acttttttct     780
taaggcatac tagtacaagt ggtaattttt gtacattaca ctaaattatt agcatttgtt     840
ttagcattac ctaattttt tcctgctcca tgcagactgt tagcttttac cttaaatgct     900
tattttaaaa tgacagtgga gttttttttt tcctctaagt gccagtattc ccagagtttt     960
ggtttttgaa ctagcaatgc ctgtgaaaaa gaaactgaat acctaagatt tctgtcttgg    1020 ggttttggt gcatgcagtt gattacttct tatttttctt accaattgtg aatgttggtg    1080
tgaaacaaat taatgaagct tttgaatcat ccctattctg tgttttatct agtcacataa    1140
```

```
atggattaat tactaatttc agttgagacc ttctaattgg tttttactga aacattgagg    1200
gaacacaaat ttatgggctt cctgatgatg attcttctag gcatcatgtc ctatagtttg    1260
tcatccctga tgaatgtaaa gttacactgt tcacaaaggt tttgtctcct ttccactgct    1320
attagtcatg gtcactctcc ccaaaatatt atatttttc tataaaaga aaaaatgga       1380 aaaaaattac aaggcaatgg aaactattat aaggccattt cctttccaca ttagataaat    1440
tactataaag actcctaata gcttttcctg ttaaggcaga cccagtatga atgggggatt    1500
attatagcaa ccattttggg gctatatta catgctacta aatttttata ataattgaaa     1560
agattttaac aagtataaaa aattctcata ggaattaaat gtagtctccc tgtgtcagac    1620
tgctctttca tagtataact ttaaatcttt tcttcaactt gagtctttga agatagtttt    1680
aattctgctt gtgacattaa aagattattt gggccagtta tagcttatta ggtgttgaag    1740
agaccaaggt tgcaaggcca ggccctgtgt gaacctttga gctttcatag agagtttcac    1800
agcatggact gtgtccccac ggtcatccag tgttgtcatg cattggttag tcaaaatggg    1860
gagggactag ggcagtttgg atagctcaac aagatacaat ctcactctgt ggtggtcctg    1920
ctgacaaatc aagagcattg cttttgtttc ttaagaaaac aaactctttt ttaaaaatta    1980
cttttaaata ttaactcaaa agttgagatt ttgggggtggt ggtgtgccaa gacattaatt    2040 tttttttaa acaatgaagt gaaaagttt tacaatctct aggtttggct agttctctta     2100
acactggtta aattaacatt gcataaacac ttttcaagtc tgatccatat ttaataatgc    2160
tttaaaataa aaataaaaac aatccttttg ataaatttaa aatgttactt attttaaaat    2220
aaatgaagtg agatggcatg gtgaggtgaa agtatcactg gactaggaag aaggtgactt    2280
aggttctaga taggtgtctt ttaggactct gattttgagg acatcactta ctatccattt    2340
cttcatgtta aaagaagtca tctcaaactc ttagtttttt ttttttacaa ctatgtaatt    2400
tatattccat ttacataagg atacacttat ttgtcaagct cagcacaatc tgtaaatttt    2460
taacctatgt tacaccatct tcagtgccag tcttgggcaa aattgtgcaa gaggtgaagt    2520
ttatatttga atatccattc tcgttttagg actcttcttc catattagtg tcatcttgcc    2580
tccctacctt ccacatgccc catgacttga tgcagtttta atacttgtaa ttcccctaac    2640
cataagattt actgctgctg tggatatctc catgaagttt tcccactgag tcacatcaga    2700
aatgccctac atcttatttc ctcagggctc aagagaatct gacagatacc ataaagggat    2760
ttgacctaat cactaatttt caggtggtgg ctgatgcttt gaacatctct ttgctgccca    2820
atccattagc gacagtagga tttttcaaac ctggtatgaa tagacagaac cctatccagt    2880
ggaaggagaa tttaataaag atagtgctga agaattcct taggtaatct ataactagga    2940
ctactcctgg taacagtaat acattccatt gttttagtaa ccagaaatct tcatgcaatg    3000
aaaaatactt taattcatga agcttacttt tttttttgg tgtcagagtc tcgctcttgt    3060
cacccaggct ggaatgcagt ggcgccatct cagctcactg caacctccat ctcccaggtt    3120
caagcgattc tcgtgcctcg gcctcctgag tagctgggat tacaggcgtg tgccactaca    3180
ctcaactaat ttttgtattt ttaggagaga cggggtttca ccctgttggc caggctggtc    3240
tcgaactcct gacctcaagt gattcaccca ccttggcctc ataaacctgt tttgcagaac    3300
tcatttattc agcaaatatt tattgagtgc ctaccagatg ccagtcaccg cacaaggcac    3360
tgggtatatg gtatccccaa acaagagaca taatcccggt ccttaggtag tgctagtgtg    3420
gtctgtaata tcttactaag gcctttggta tacgacccag agataacacg atgcgtattt    3480
```

```
tagttttgca aagaaggggt ttggtctctg tgccagctct ataattgttt tgctacgatt    3540
ccactgaaac tcttcgatca agctacttta tgtaaatcac ttcattgttt taaaggaata    3600
aacttgatta tattgttttt ttatttggca taactgtgat tcttttagga caattactgt    3660
acacattaag gtgtatgtca gatattcata ttgacccaaa tgtgtaatat tccagttttc    3720
tctgcataag taattaaaat atacttaaaa attaatagtt ttatctgggt acaaataaac    3780
aggtgcctga actagttcac agacaaggaa acttctatgt aaaaatcact atgatttctg    3840
aattgctatg tgaaactaca gatctttgga acactgttta ggtagggtgt taagacttac    3900
acagtacctc gtttctacac agagaaagaa atggccatac ttcaggaact gcagtgctta    3960 tgagggata tttaggcctc ttgaattttt gatgtagatg ggcattttt taaggtagtg     4020 gttaattacc tttatgtgaa ctttgaatgg tttaacaaaa gatttgtttt tgtagagatt    4080
ttaaaggggg agaattctag aaataaatgt tacctaatta ttacagcctt aaagacaaaa    4140
atccttgttg aagtttttt aaaaaaagct aaattacata gacttaggca ttaacatgtt     4200
tgtggaagaa tatagcagac gtatattgta tcatttgagt gaatgttccc aagtaggcat    4260
tctaggctct atttaactga gtcacactgc ataggaattt agaacctaac ttttataggt    4320
tatcaaaact gttgtcacca ttgcacaatt ttgtcctaat atatacatag aaactttgtg    4380
gggcatgtta agttacagtt tgcacaagtt catctcattt gtattccatt gattttttt     4440 ttcttctaaa cattttttct tcaaacagta tataactttt tttaggggat ttttttttag    4500
acagcaaaaa ctatctgaag atttccattt gtcaaaaagt aatgatttct tgataattgt    4560
gtagtaatgt ttttagaac ccagcagtta ccttaaagct gaatttatat ttagtaactt     4620
ctgtgttaat actggatagc atgaattctg cattgagaaa ctgaatagct gtcataaaat    4680
gaaactttct ttctaaagaa agatactcac atgagttctt gaagaatagt cataactaga    4740
ttaagatctg tgttttagtt taatagtttg aagtgcctgt ttgggataat gataggtaat    4800
ttagatgaat ttaggggaaa aaaaagttat ctgcagatat gttgagggcc catctctccc    4860
cccacacccc cacagagcta actgggttac agtgttttat ccgaaagttt ccaattccac    4920
tgtcttgtgt tttcatgttg aaaatacttt tgcattttc ctttgagtgc caattcctta    4980
ctagtactat ttcttaatgt aacatgttta cctggaatgt attttaacta ttttttgtata   5040 gtgtaaactg aaacatgcac attttgtaca ttgtgctttc ttttgtggga catatgcagt    5100
gtgatccagt tgttttccat catttggttg cgctgaccta ggaatgttgg tcatatcaaa    5160
cattaaaaat gaccactctt ttaattgaaa ttaactttta aatgtttata ggagtatgtg    5220
ctgtgaagtg atctaaaatt tgtaatattt ttgtcatgaa ctgtactact cctaattatt    5280
gtaatgtaat aaaaatagtt acagtgacta tgagtgtgta tttattcatg aaatttgaac    5340
tgtttgcccc gaaatggata tggaatactt tataagccat agacactata gtataccagt    5400
gaatctttta tgcagcttgt tagaagtatc ctttatttct aaaaggtgct gtggatatta    5460
tgtaaaggcg tgtttgctta aacttaaaac catatttaga agtagatgca aaacaaatct    5520
gcctttatga caaaaaaata ggataacatt atttatttat ttcctttat caagaaggt     5580 aattgataca caacaggtga cttggtttta ggcccaaagg tagcagcagc aacattaata    5640
atggaaataa ttgaatagtt agttatgtat gttaatgcca gtcaccagca ggctatttca    5700
aggtcagaag taatgactcc atacatatta tttatttcta taactacatt taaatcatta    5760
ccagg                                                               5765
```

<210> SEQ ID NO 4
<211> LENGTH: 3291
<212> TYPE: DNA
<213> ORGANISM: Homo sapiens

<400> SEQUENCE: 4

| | | | | | |
|---|---|---|---|---|---|
| agaatcggag | agccggtggc | gtcgcaggtc | gggaggacga | gcaccgagtc | gagggctcgc | 60 |
| tcgtctgggc | cgcccgagag | tcttaatcgc | gggcgcttgg | gccgccatct | tagatggcgg | 120 |
| gagtaagagg | aaaacgattg | tgaggcggga | acggctttct | gctgcctttt | ttgggccccg | 180 |
| aaaagggtca | gctggccggg | ctttggggcg | cgtgccctga | ggcgcggagc | gcgtttgcta | 240 |
| cgatgcgggg | gctgctcggg | gctccgtccc | ctgggctggg | gacgcgccga | atgtgaccgc | 300 |
| ctcccgctcc | ctcacccgcc | gcggggagga | ggagcgggcg | agaagctgcc | gccgaacgac | 360 |
| aggacgttgg | ggcggcctgg | ctccctcagg | tttaagaatt | gtttaagctg | catcaatgga | 420 |
| gcacatacag | ggagcttgga | agacgatcag | caatggtttt | ggattcaaag | atgccgtgtt | 480 |
| tgatggctcc | agctgcatct | ctcctacaat | agttcagcag | tttggctatc | agcgccgggc | 540 |
| atcagatgat | ggcaaactca | cagatccttc | taagacaagc | aacactatcc | gtgttttctt | 600 |
| gccgaacaag | caagaacag | tggtcaatgt | gcgaaatgga | atgagcttgc | atgactgcct | 660 |
| tatgaaagca | ctcaaggtga | ggggcctgca | accagagtgc | tgtgcagtgt | tcagacttct | 720 |
| ccacgaacac | aaaggtaaaa | aagcacgctt | agattggaat | actgatgctg | cgtctttgat | 780 |
| tggagaagaa | cttcaagtag | atttcctgga | tcatgttccc | ctcacaacac | acaactttgc | 840 |
| tcggaagacg | ttcctgaagc | ttgccttctg | tgacatctgt | cagaaattcc | tgctcaatgg | 900 |
| atttcgatgt | cagacttgtg | gctacaaatt | tcatgagcac | tgtagcacca | agtacctac | 960 |
| tatgtgtgtg | gactggagta | acatcagaca | actcttattg | tttccaaatt | ccactattgg | 1020 |
| tgatagtgga | gtcccagcac | taccttcttt | gactatgcgt | cgtatgcgag | agtctgtttc | 1080 |
| caggatgcct | gttagttctc | agcacagata | ttctacacct | cacgccttca | cctttaacac | 1140 |
| ctccagtccc | tcatctgaag | gttccctctc | ccagaggcag | aggtcgacat | ccacacctaa | 1200 |
| tgtccacatg | gtcagcacca | ccctgcctgt | ggacagcagg | atgattgagg | atgcaattcg | 1260 |
| aagtcacagc | gaatcagcct | caccttcagc | cctgtccagt | agcccaaca | atctgagccc | 1320 |
| aacaggctgg | tcacagccga | aaaccccgt | gccagcacaa | agagagcggg | caccagtatc | 1380 |
| tgggacccag | gagaaaaaca | aaattaggcc | tcgtggacag | agagattcaa | gctattattg | 1440 |
| ggaaatagaa | gccagtgaag | tgatgctgtc | cactcggatt | gggtcaggct | cttttggaac | 1500 |
| tgtttataag | ggtaaatggc | acggagatgt | tgcagtaaag | atcctaaagg | ttgtcgaccc | 1560 |
| aaccccagag | caattccagg | ccttcaggaa | tgaggtggct | gttctgcgca | aaacacggca | 1620 |
| tgtgaacatt | ctgcttttca | tggggtacat | gacaaaggac | aacctggcaa | ttgtgaccca | 1680 |
| gtggtgcgag | ggcagcagcc | tctacaaaca | cctgcatgtc | caggagacca | gtttcagat | 1740 |
| gttccagcta | attgacattg | cccggcagac | ggctcaggga | atggactatt | tgcatgcaaa | 1800 |
| gaacatcatc | catagagaca | tgaaatccaa | caatatattt | ctccatgaag | gcttaacagt | 1860 |
| gaaaattgga | gattttggtt | tggcaacagt | aaagtcacgc | tggagtggtt | ctcagcaggt | 1920 |
| tgaacaacct | actggctctg | tcctctggat | ggccccagag | gtgatccgaa | tgcaggataa | 1980 |
| caacccattc | agtttccagt | cggatgtcta | ctcctatggc | atcgtattgt | atgaactgat | 2040 |
| gacgggggag | cttccttatt | ctcacatcaa | caaccgagat | cagatcatct | tcatggtggg | 2100 |
| ccgaggatat | gcctccccag | atcttagtaa | gctatataag | aactgcccca | aagcaatgaa | 2160 |

-continued

| | |
|---|---|
| gaggctggta gctgactgtg tgaagaaagt aaaggaagag aggcctcttt ttccccagat | 2220 |
| cctgtcttcc attgagctgc tccaacactc tctaccgaag atcaaccgga gcgcttccga | 2280 |
| gccatccttg catcgggcag cccacactga ggatatcaat gcttgcacgc tgaccacgtc | 2340 |
| cccgaggctg cctgtcttct agttgacttt gcacctgtct tcaggctgcc aggggaggag | 2400 |
| gagaagccag caggcaccac ttttctgctc cctttctcca gaggcagaac acatgttttc | 2460 |
| agagaagctg ctgctaagga ccttctagac tgctcacagg ccttaacttc atgttgcct | 2520 |
| tcttttctat ccctttgggc cctgggagaa ggaagccatt tgcagtgctg gtgtgtcctg | 2580 |
| ctccctcccc acattcccca tgctcaaggc ccagccttct gtagatgcgc aagtggatgt | 2640 |
| tgatggtagt acaaaaagca ggggcccagc cccagctgtt ggctacatga gtatttagag | 2700 |
| gaagtaaggt agcaggcagt ccagccctga tgtggagaca catgggattt tggaaatcag | 2760 |
| cttctggagg aatgcatgtc acaggcggga ctttcttcag agagtggtgc agcgccagac | 2820 |
| attttgcaca taaggcacca aacagcccag gactgccgag actctggccg cccgaaggag | 2880 |
| cctgctttgg tactatggaa cttttcttag gggacacgtc ctcctttcac agcttctaag | 2940 |
| gtgtccagtg cattgggatg ttttccagg caaggcactc ggccaatccg catctcagcc | 3000 |
| ctctcaggga gcagtcttcc atcatgctga attttgtctt ccaggagctg cccctatggg | 3060 |
| gcggggccgc agggccagcc ttgtttctct aacaaacaaa caaacaaaca gccttgtttc | 3120 |
| tctagtcaca tcatgtgtat acaaggaagc caggaataca ggttttcttg atgatttggg | 3180 |
| ttttaatttt gttttattg cacctgacaa atacagttac tctgatggtc cctcaattat | 3240 |
| gttattttaa taaataaat taaatttagg tgtaaaaaaa aaaaaaaaaa a | 3291 |

<210> SEQ ID NO 5
<211> LENGTH: 2186
<212> TYPE: DNA
<213> ORGANISM: Homo sapiens

<400> SEQUENCE: 5

| | |
|---|---|
| agcagtcacg tgcctccgat cacgtgaccg gcgcctctgt cattctactg cggccgccct | 60 |
| ggcttccttc tacctgtgcg gccctcaacg tctccttggt gcgggacccg cttcactttc | 120 |
| ggctcccgga gtctccctcc actgctcaga cctctggacc tgacaggaga cgcctacttg | 180 |
| gctctgacgc ggcgccccag cccggctgtg tccccggcgc cccggaccac cctccctgcc | 240 |
| ggctttgggt gcgttgtggg gtcccgagga ttcgcgagat ttgttgaaag acattcaaga | 300 |
| ttacgaagtt tagatgacca aaatggatat ccgaggtgct gtggatgctg ctgtccccac | 360 |
| caatattatt gctgccaagg ctgcagaagt tcgtgcaaac aaagtcaact ggcaatccta | 420 |
| tcttcaggga cagatgattt ctgctgaaga ttgtgagttt attcagaggt ttgaaatgaa | 480 |
| acgaagccct gaagagaagc aagagatgct tcaaactgaa ggcagccagt gtgctaaaac | 540 |
| atttataaat ctgatgactc atatctgcaa agaacagacc gttcagtata tactaactat | 600 |
| ggtggatgat atgctgcagg aaaatcatca gcgtgttagc attttctttg actatgcaag | 660 |
| atgtagcaag aacactgcgt ggccctactt tctgccaatg ttgaatcgcc aggatccctt | 720 |
| cactgttcat atggcagcaa gaattattgc caagttagca gctggggaa agaactgat | 780 |
| ggaaggcagt gacttaaatt actatttcaa ttggataaaa actcagctga gttcacagaa | 840 |
| actgcgtggt agcggtgttg ctgttgaaac aggaacagtc tcttcaagtg atagttcgca | 900 |
| gtatgtgcag tgcgtggccg ggtgtttgca gctgatgctc cgggtcaatg agtaccgctt | 960 |
| tgcttgggtg gaagcagatg gggtaaattg cataatggga gtgttgagta caagtgtgg | 1020 |

```
ctttcagctc cagtatcaaa tgatttttc aatatggctc ctggcattca gtcctcaaat    1080
gtgtgaacac ctgcggcgct ataatatcat tccagttctg tctgatatcc ttcaggagtc    1140
tgtcaaagag aaagtaacaa gaatcattct tgcagcattt cgtaactttt tagaaaaatc    1200
aactgaaaga gaaactcgcc aagaatatgc cctggctatg attcagtgca agttctgaa     1260 acagttggag aacttggaac agcagaagta cgatgatgaa gatatcagcg aagatatcaa    1320 atttctttg gaaaaacttg gagagagtgt ccaggacctt agttcatttg atgaatacag      1380
ttcagaactt aaatctggaa ggttggaatg gagtcctgtg cacaaatctg agaaatttg      1440 gagagagaat gctgtgaggt taaatgagaa gaattatgaa ctcttgaaaa tcttgacaaa    1500
acttttggaa gtgtcagatg atccccaagt cttagctgtt gctgctcacg atgttggaga    1560
atatgtgcgg cattatccac gaggcaaacg ggtcatcgag cagctcggtg ggaagcagct    1620
ggtcatgaac cacatgcatc atgaagacca gcaggtccgc tataatgctc tgctggccgt    1680
gcagaagctc atggtgcaca actgggaata ccttggcaag cagctccagt ccagcagcc     1740 ccagaccgct gccgcccgaa gctaagcctg cctctggcct tcccctccgc ctcaatgcag    1800
aaccagtagt gggagcactg tgtttagagt taagagtgaa cactgtttga ttttacttgg    1860
aatttcctct gttatatagc ttttcccaat gctaatttcc aaacaacaac aacaaaataa    1920
catgtttgcc tgttaagttg tataaaagta ggtgattctg tatttaaaga aaatattact    1980
gttacatata ctgcttgcaa tttctgtatt tattgttctc tggaaataaa tatagttatt    2040
aaaggattct cactccaaac atggcctctc tctttacttg gactttgaac aaaagtcaac    2100
tgttgtctct tttcaaacca aattgggaga attgttgcaa agtagtgaat ggcaaataaa    2160
tgttttaaaa tctatcgctc tatcaa                                         2186

<210> SEQ ID NO 6
<211> LENGTH: 1947
<212> TYPE: DNA
<213> ORGANISM: Homo sapiens

<400> SEQUENCE: 6
atgcagatga ggcactcggg ggcggggcgg cggcggcggc ggcggcggtg gcggccgggg      60
agggtcagtt ggaggcaggc gctcgctgag gcaaaaggag gcgctcggcc gcggcctga     120 cagggactta gcccgcagag atcgaccccg cgcgcgtgac cccacaccca cccactcatc    180
catctatcca ctccctgcgc cgcctcctcc caccctgagc agagccgccg aggatgataa    240
acacccagga cagtagtatt tgccttttga gtaactgtcc ccagctccag tgctgcaggc    300
acattgttcc agggcctctg tggtgctcct gatgcccctc acccactgtc gaagatcccc    360
ggtgggcgag gggcggcag ggatccttct ctctcagctc taatatataa ggacgagaag     420
ctcactgtga cccaggacct ccctgtgaat gatggaaaac ctcacatcgt ccacttccag    480
tatgaggtca ccgaggtgaa ggtctcttct gggatgcag tcctgtccag ccagagcctg      540
tttgtagaaa tcccagatgg attattagct gatgggagca agaaggatt gttagcactg      600 ctagagtttg ctgaagagaa gatgaaagtg aactatgtct tcatctgctt caggaagggc    660
cgagaagaca gagctccact cctgaagacc ttcagcttct gggctttga gattgtacgt     720 ccaggccatc cctgtgtccc ctctcggcca gatgtgatgt tcatggttta tccctggac     780 cagaacttgt ccgatgagga ctaatagtca tagaggatgc tttacccaag agccacagtg    840
ggggaagagg ggaagttagg cagccctggg acagacgaga gggctcctcg ctgtctaggg    900
```

| | |
|---|---:|
| aaggacactg aggggctcag ggtgagggtt gcctattgtg ttctcggagt tgactcgttg | 960 |
| aaattgtttt ccataaagaa cagtataaac atattattca catgtaatca ccaatagtaa | 1020 |
| atgaagatgt ttatgaactg gcattagaag ctttctaaac tgcgctgtgt gatgtgttct | 1080 |
| atctagccta ggggaggaca ttgcctagag ggggagggac tgtctgggtt caggggcatg | 1140 |
| gcctggaggg ctggtgggca gcactgtcag gctcaggttt ccctgctgtt ggctttctgt | 1200 |
| tttggttatt aagacttgtg tattttcttt ctttgcttcc tgtcacccca ggggctcctg | 1260 |
| agtataggct tttcagtccc tgggcagtgt ccttgagttg ttttttgaca ctcttacctg | 1320 |
| ggcttctctg tgtgcatttg cgtctggcct ggagtaagca ggtccgaccc ctccttcttt | 1380 |
| acagcttagt gttattctgg catttggtta agctggctta atctgtttaa tgttatcagt | 1440 |
| acattttaaa tagggcatt gaaatttact cccaccacca gggcttttt gggggatgcc | 1500 |
| tgggccttta aaacactagc caaactctaa ttaattctca aatcactgcc aggagttctt | 1560 |
| gctcctggct gcaggcccag gcccaaggt ctccttcttg gggtcacaaa cagcagtaag | 1620 |
| gaagaggaat atatagcaac tcagggcctg ggaattgtgg ggcaatccgt tcttagggac | 1680 |
| tggatacttc tggctggctg agtatagtac tagctgcctc cccaccaggt tccgagtagt | 1740 |
| gtctgagact ctgctctgca gggcctaggg tagcgctggg agtgtagaag tggcctgccc | 1800 |
| ttaactgttt tcactaaaca gcttttcta aggggagagc aaggggggaga gatctagatt | 1860 |
| gggtgagggg gacgggatg tcagggaggc aagtgtgttg tgttactgtg tcaataaact | 1920 |
| gatttaaagt tgtgaaaaaa aaaaaaa | 1947 |

<210> SEQ ID NO 7
<211> LENGTH: 1712
<212> TYPE: DNA
<213> ORGANISM: Homo sapiens

<400> SEQUENCE: 7

| | |
|---|---:|
| atgctggggg aggggctggc ggcctcgacg gcagctgcgg aactaggccg agggacaaag | 60 |
| gctaagtttt tccatggttt ggactggata tcggtggaac tctggtcaag ctggtatatt | 120 |
| ttgaacccaa agacatcact gctgaagaag aagaggaaga agtggaaagt cttaaaagca | 180 |
| ttcggaagta cctgacctcc aatgtggctt atgggtctac aggcattcgg gacgtgcacc | 240 |
| tcgagctgaa ggacctgact ctgtgtggac gcaaaggcaa tctgcacttt atacgctttc | 300 |
| ccactcatga catgcctgct tttattcaaa tgggcagaga taaaaacttc tcgagtctcc | 360 |
| acactgtctt ttgtgccact ggaggtggag cgtacaaatt tgagcaggat tttctcacaa | 420 |
| taggtgatct tcagctttgc aaactggatg aactagattg cttgatcaaa ggaattttat | 480 |
| acattgactc agtcggattc aatggacggt cacagtgcta ttactttgaa acccctgctg | 540 |
| attctgaaaa gtgtcagaag ttaccatttg atttgaaaaa tccgtatcct ctgcttctgg | 600 |
| tgaacattgg ctcagggggtt agcatcttag cagtatattc caaagataat tacaaacggg | 660 |
| tcacaggtac tagtcttgga ggaggaactt tttttggtct ctgctgtctt cttactggct | 720 |
| gtaccacttt tgaagaagct cttgaaatgg catctcgtgg agatagcacc aaagtggata | 780 |
| aactagtacg agatatttat ggaggggact atgagaggtt tggactgcca ggctgggctg | 840 |
| tggcttcaag cttttggaaac atgatgagca aggagaagcg agaggctgtc agtaaagagg | 900 |
| acctggccag agcgactttg atcaccatca ccaacaacat tggctcaata gcaagaatgt | 960 |
| gtgcccttaa tgaaaacatt aaccaggtgg tatttgttgg aaatttcttg agaattaata | 1020 |
| cgatcgccat gcggctttg gcatatgctt tggattattg gtccaagggg cagttgaaag | 1080 |

```
cacttttttc ggaacacgag ggttattttg gagctgttgg agcactcctt gagctgttga      1140
agatcccgtg atcattacct ggggagggggt tcctgaaacc ttccacaatg ggatctgtgg     1200
actttcattt ttttaagaga cttactcaat ttcatgactg tactacctga aacaaagtga     1260
gaaaggacag gtgtattttt ctaagtcatc aagataaatc cttaagaatt cagtctaaat     1320
tagcaaccag gaaggaaaaa tatattaaaa acaacaaaaa agtggcacat gtccaggcag     1380
tgtgaggatt tgctgtatat aagttgcctg ctttgtattt ttgaaatctc tgcatcactc     1440
attggaagtg cttctgaaga gagctgctct gtgttcagtt gactggtttt gtgtcctgtt     1500
tgaacttgct gaatgtaagg caggctacta tgcgttataa tctaatcaca atttgtcaat     1560
atggtcttgg caatcatctg tgcattactc tggtttgcat taagcctgtg tgtgaactta     1620
ctgtaaaaca tgttttattt caaggttctg caaaattaat tgggcaggtt aattgtgtac     1680
ctgaaactta acaagcagtt tttggaaggg ca                                    1712

<210> SEQ ID NO 8
<211> LENGTH: 2207
<212> TYPE: DNA
<213> ORGANISM: Homo sapiens

<400> SEQUENCE: 8
gcatcctctc accgccggaa gctgaactga ctcgtccgcg ccgctctac cccaacaggc       60 cgccaccagc gagagtgcgg ccataaccat cacgtgaccg cccaccgaca ccagcgagag     120
tgcagtcgta accgtcacgt gaccgcccac cgtcggcccg cgctcccct ccgcccgaag      180 ctagcaagcg gcgcggccaa tgagaaaggc gcatgcctgg ccccccgccgg cctgcagtct    240 agccgtagtg cgcctgcgcg cggctaggag ggggccgtcag gcggggatac agcctggaag   300
gtaatgcatg tccatggtac acaaattcac aagtttggag accctgacac acccaccttc   360
tcacctgggc tctgcgtatc ccccagcctt gagggaagat gaagcctaaa ctgatgtacc   420
aggagctgaa ggtgcctgca gaggagcccg ccaatgagct gcccatgaat gagattgagg   480
cgtggaaggc tgcggaaaag aaagcccgct gggtcctgct ggtcctcatt ctggcggttg   540
tgggcttcgg agccctgatg actcagctgt ttctatggga atacggcgac ttgcatctct   600
ttgggcccaa ccagcgccca gcccctgct atgacccttg cgaagcagtg ctggtggaaa    660
gcattcctga gggcctggac ttccccaatg cctccacggg gaacccttcc accagccagg   720
cctggctggg cctgctcgcc ggtgcgcaca gcagcctgga catcgcctcc ttctactgga   780
ccctcaccaa caatgacacc cacacgcagg agccctctgc ccagcagggt gaggaggtcc   840
tccggcagct gcagaccctg gcaccaaagg gcgtgaacgt ccgcatcgct gtgagcaagc   900
ccagcgggcc ccagccacag gcggacctgc aggctctgct gcagagcggt gcccaggtcc   960
gcatggtgga catgcagaag ctgacccatg gcgtcctgca taccaagttc tgggtggtgg    1020
accagaccca cttctacctg ggcagtgcca acatggactg gcgttcactg acccaggtca   1080
aggagctggg cgtggtcatg tacaactgca gctgcctggc tcgagacctg accaagatct   1140
ttgaggccta ctggttcctg ggccaggcag gcagctccat cccatcaact tggccccggt   1200
tctatgacac ccgctacaac caagagacac caatggagat ctgcctcaat ggaacccctg   1260
ctctggccta cctggcgagt gcgcccccac ccctgtgtcc aagtggccgc actccagacc   1320
tgaaggctct actcaacgtg gtggacaatg cccggagttt catctacgtc gctgtcatga   1380
actacctgcc cactctggag ttctcccacc ctcacaggtt ctggcctgcc attgacgatg   1440
```

| | | | | | |
|---|---|---|---|---|---|
| ggctgcggcg | ggccacctac | gagcgtggcg | tcaaggtgcg | cctgctcatc | agctgctggg | 1500 |
| gacactcgga | gccatccatg | cgggccttcc | tgctctctct | ggctgccctg | cgtgacaacc | 1560 |
| atacccactc | tgacatccag | gtgaaactct | tgtggtccc | cgcggatgag | gcccaggctc | 1620 |
| gaatcccata | tgcccgtgtc | aaccacaaca | agtacatggt | gactgaacgc | gccacctaca | 1680 |
| tcggaaccct | caactggtct | ggcaactact | tcacggagac | ggcgggcacc | tcgctgctgg | 1740 |
| tgacgcagaa | tgggaggggc | ggcctgcgga | gccagctgga | ggccattttc | ctgagggact | 1800 |
| gggactcccc | ttacagccat | gaccttgaca | cctcagctga | cagcgtgggc | aacgcctgcc | 1860 |
| gcctgctctg | aggcccgatc | cagtgggcag | gccaaggcct | gctgggcccc | cgcggaccca | 1920 |
| ggtgctctgg | gtcacggtcc | ctgtccccgc | gcccccgctt | ctgtctgccc | cattgtggct | 1980 |
| cctcaggctc | tctcccctgc | tctcccacct | ctacctccac | ccccaccggc | ctgacgctgt | 2040 |
| ggccccggga | cccagcagag | ctgggggagg | gatcagcccc | caaagaaatg | ggggtgcatg | 2100 |
| ctgggcctgg | cccctggcc | cacccccact | ttccagggca | aaaagggccc | agggttataa | 2160 |
| taagtaaata | acttgtctgt | acagcctgaa | aaaaaaaaa | aaaaaaa | | 2207 |

<210> SEQ ID NO 9
<211> LENGTH: 6158
<212> TYPE: DNA
<213> ORGANISM: Homo sapiens

<400> SEQUENCE: 9

| | | | | | |
|---|---|---|---|---|---|
| gtcttttgtc | cctcggcgga | caccgtttgc | cagccaaagc | tatgtctgcg | cgctcaccga | 60 |
| cttcataggg | tgccgaattc | ttttttcccc | aggcttgcca | tggctagtcg | aggggctcgg | 120 |
| cagcgcctga | agggcagcgg | ggccagcagt | ggggatacgg | ccccggctgc | ggacaagctg | 180 |
| cgggagctgc | tggcagccg | agaggcgggc | ggcgcggagc | accggaccga | gttatctggg | 240 |
| aacaaagcag | gacaagtctg | ggcacctgaa | ggatctactg | ctttcaagtg | tctgctttca | 300 |
| gcaaggttat | gtgctgctct | cctgagcaac | atctctgact | gtgatgaaac | attcaactac | 360 |
| tgggagccaa | cacactacct | catctatggg | gaagggtttc | agacttggga | atattcccca | 420 |
| gcatatgcca | ttcgctccta | tgcttacctg | ttgcttcatg | cctggccagc | tgcatttcat | 480 |
| gcaagaattc | tacaaactaa | taagattctt | gtgttttact | ttttgcgatg | tcttctggct | 540 |
| tttgtgagct | gtatttgtga | actttacttt | tacaaggctg | tgtgcaagaa | gtttgggttg | 600 |
| cacgtgagtc | gaatgatgct | agccttcttg | gttctcagca | ctggcatgtt | ttgctcatca | 660 |
| tcagcattcc | ttcctagtag | cttctgtatg | tacactacgt | tgatagccat | gactggatgg | 720 |
| tatatggaca | agacttccat | tgctgtgctg | ggagtagcag | ctggggctat | cttaggctgg | 780 |
| ccattcagtg | cagctcttgg | tttacccatt | gcctttgatt | tgctggtcat | gaaacacagg | 840 |
| tggaagagtt | tctttcattg | gtcgctgatg | gccctcatac | tatttctggt | gcctgtggtg | 900 |
| gtcattgaca | gctactatta | tgggaagttg | gtgattgcac | cactcaacat | tgttttgtat | 960 |
| aatgtcttta | ctcctcatgg | acctgatctt | tatggtacag | aaccctggta | tttctattta | 1020 |
| attaatggat | ttctgaattt | caatgtagcc | tttgctttgg | ctctcctagt | cctaccactg | 1080 |
| acttctctta | tggaatacct | gctgcagaga | tttcatgttc | agaatttagg | ccacccgtat | 1140 |
| tggcttacct | tggctccaat | gtatatttgg | tttataattt | tcttcatcca | gcctcacaaa | 1200 |
| gaggagagat | ttcttttccc | tgtgtatcca | cttatatgtc | tctgtggcgc | tgtggctctc | 1260 |
| tctgcacttc | agcacagttt | tctgtacttc | cagaaatgtt | accactttgt | gtttcaacga | 1320 |
| tatcgcctgg | agcactatac | tgtgacatcg | aattggctgg | cattaggaac | tgtcttcctg | 1380 |

```
tttgggctct tgtcattttc tcgctctgtg gcactgttca gaggatatca cgggcccctt    1440
gatttgtatc cagaatttta ccgaattgct acagacccaa ccatccacac tgtcccagaa    1500
ggcagacctg tgaatgtctg tgtgggaaaa gagtggtatc gatttcccag cagcttcctt    1560
cttcctgaca attggcagct tcagttcatt ccatcagagt tcagaggtca gttaccaaaa    1620 cctttttgcag aaggacctct ggccacccgg attgttccta ctgacatgaa tgaccagaat    1680
ctagaagagc catccagata tattgatatc agtaaatgcc attatttagt ggatttggac    1740
accatgagag aaacaccccg ggagccaaaa tattcatcca ataaagaaga atggatcagc    1800
ttggcctata gaccattcct tgatgcttct agatcttcaa agctgctgcg ggcattctat    1860
gtccccttcc tgtcagatca gtatacagtg tacgtaaact acaccatcct caaaccccgg    1920
aaagcaaagc aaatcaggaa gaaaagtgga ggttagcaac acacctgtgg ccccaaagga    1980
caaccatctt gttaactatt gattccagtg acctgactcc ctgcaagtca tcgcctgtaa    2040
catttgtaat aaaggtcttc tgacatgaat actggaatct gggtgctctg gctagtcaa    2100 agtctatttc aaagtctaat caaagtcaca tttgctccct gtgtgtgtct ctgttctgca    2160
tgtaaacttt ttgcagctag gcagagaaag gccctaaagc acagatagat atattgctcc    2220
acatctcatt gttttcctc tgttcaatta tttactagac cggagaagag cagaaccaac    2280
ttacaggaag aattgaaaat cctggtactg gatggctgtg ataagctgtt ctccacactc    2340
tggcctggca tctgagaact agcaagcctc tcttaggcca tatgggcttc tccaccaaag    2400
ctgtttggca gctcctagca gaccttctta ttgaaatcct catgctgaaa atgaacacag    2460
cctagttgcc aacccacatg tcctttcac ctccagcaag actaagcttc tttaaagcac    2520
ttcacaggac taggccctg tcctggagct atctcaggaa aaaggtgacc atttgaggaa    2580
ctgtgaccta atttattat aatgatgcct ctaattttca tttcctttac aaccaactgt    2640
aactataagg ttgtattgct ttttgttca gttttagcat gctatttttt gaattctaga    2700
ctcctccatg tgaagatatc aacagacaaa actacaactg tataggacat attggagaa    2760 aattctatca attgatacat ttggatgaca tcacattttt aagtaatgta atctgaggcc    2820
attgctgagg aaattaagaa ttttccttt tttttaacca cccccagtga aaaggatcag    2880
tgtatattta tagcacctat tttttagttc tgtctgttgt gaggcacatc ctgcatgggg    2940
cacttctagt caaataggca atgataagga cctaattaaa atgtgataag tgtatactat    3000
tactttaaaa gcctttacag tcagtacttc agtttacaag gcactttcac agcatctcgt    3060
ttgatcctca cagtcacaac atgtggtaga caaggcaggt gatttttatc cccattttac    3120
agataaggaa acaggctgcg ggtggggagt gaggggaggt aaagatagtt agttgcctaa    3180
ggtcacacag ccagtaagta atagagctgg gactggaacc caggtttcct tactctcatc    3240
tattgctcct ccatattcct cactcaacca tgaaaacatt acttgaaagg actgatgagg    3300
ttaaccagag acctaactga tattgtaact ttctatttta aggaagaatt gtgtctgtat    3360
ttgagttctt tggagcctcc agtctgcctg tgtgttagac cagcacagca gtgctgtgtg    3420
atgcagcctg acctgtggca ggaaagtagt gcttctgttt ggaagtcatg ttcttttgca    3480
gccacacagg atccaaatat cagtactatt cctgtagtca atctgggtc acattatagg    3540 tgccttattt ccctaagggt aactgatctg aatatctgca aataggatga atctattttt    3600
cagaagttcc atctttcatt tttctttttt ttttgagac agagtctcat tctgtcgccc    3660
atgctggagt gcagtggcgc gatctcggct cgctgcaacc tctgcctccc aggttgaagc    3720
```

```
aattctcatg cctcagccac ccgagtagct gggattacag gcatgcgcca tcatgcccag    3780
ctaatttatg tattttttagt agagttggag tttcaccatg ttggccaggc tggtcttgga    3840
ctcctgacct caggtcatcc acccgcctca gcctcccaaa gtgctggtat tacaggcgtg    3900
agccaccgca cccagcccca tctttcattt tcaaagagaa gggcattcta ataggaactg    3960
gtgccaagag agaagaaaag aagtgataac agaagaaatg gctagttaca atattaaaaa    4020
gctcctcttt gagatctcct ctgcaggaat atcagacg gagttgaagc gctggagagg    4080
taataggtct agacagtaca gaacaataac tggggagtgt gtgaggatag actgggctcc    4140
cccttgcttg aaagatctct ggcatttaat tctcaattct tgattactat tttccagtgt    4200
aaaactagca catatgatct gactacagga cagagaattt taagtgaaac atttgcctta    4260
cttgcagtaa taatgtgctg ttcttcacag tagctaaggc cctctatgtt tcccagaggt    4320
aaataagaat ccaggaatgg aggtccatct gtgatgaatg gcttttttct aatcaaagta    4380
gtataatgct gttttatctg ttttgtcatc ttgtttttt ttttttttaa aaaaacaaaa    4440
ccttaattat aatatagcgc aaagaaaggc caggactgat gcaggattc cttggaaata    4500 tcagttccta tcactttaa aacctgattt tggatctctc tgttctatgt atgtctttag    4560
tgagagcaca atacatggca gaacgctgtg ccaaatgtta taggtaagga atatagaaat    4620
gaatgttttt tgttgtgaag gtgttttcat gtgatatttt ataaacacat tttaaaaat    4680 ctccatcact ttttagtata ggaaggatag ctttgcctgg gaaaaacagt ttcaacacac    4740
ctgctcagag tagcagttct ccctcaaaaa agcagtgttc agcctgcact gactgttctg    4800
cttgccaaaa ggaggaagca tgcaagatac ttatttctcc atagattgtg gagtatagag    4860
ggatgtggga ctacagatta ttattttttt tccccgagac agagtcttgc tctgtcgccc    4920
aggttggaac acaatggcac gacctcagct cactgcaacc tctgtctccc gggttcaagc    4980
aattctcctg cttcagcctc ctgagtagct gggattacag gcacacacca ccaccgcact    5040
cagctaattt ttgtattttt agtagaggtg gggttttacc atgttggcca ggctggtctt    5100
aaactcctga ccttgtaatc atcccgcctc ggcctcctaa agtgctagga ttacaggcat    5160
gagccaccgc acccggccca gataattttt aatagccttt gatcatgggg tgagtgaggg    5220
agtaggtata cttggcaaat gcatggttct ctgatttcta gctctaaagc agccttatct    5280
gaatccccaa atcttgtgat gctgagtacc attactgaac cagtctgcac ggtaggcatc    5340
tgctaccaaa atttacctcc tacctggtag gtgtcatctg ataagaaaga agacaggtta    5400
ttttaatttt ttgagataat cacagaaaat tgcagcccat actctttatt accgaattca    5460 agttggaaa tagacccttt gttttaaatc atgatgggtc tttatcccaa tcatttatct    5520
gggtcatttt tccaactttg gagttctagg aaagaacctt gaaaacctga tatgattctg    5580
cagcatgagg tctacggtga ccatttgggc aaagctccag tggcaatcat ttattgtgtt    5640
ttgcatttcc tgggatttat tgaaataaga attcactgtg attatgtagt cttctggcta    5700
gtatcaggca gctctgcttt taatttggtt aattttattt tctctgaaga gggagaagag    5760
gtacaattta atcttggcct ccacaagcat attaaagctc acgtgttaat cagtgcattc    5820
ttatgctcct acattaaatg ccttgggtaa atggataaat ggacatgtgc ccagctttaa    5880
ttttttttgc aacagaaaga tcagacttcc gtatggcatc gttggatttc agaggctttc    5940
tggtgtatct gtaaatctga atgttgcctt ctgccagtct gtataaccag gtgattcatg    6000
ctgcaaatga aatcaggaag cagtaaagtg ttaaagcaag agtattgtcc aattcacttg    6060
```

| | |
|---|---:|
| tcttcctgat ccttgtactt tatttcacgt gtcggtgttt acattacata cttatatttc | 6120 |
| ctgtgaaaga aagagttaaa taaattgtag cagtttga | 6158 |

<210> SEQ ID NO 10
<211> LENGTH: 4451
<212> TYPE: DNA
<213> ORGANISM: Homo sapiens

<400> SEQUENCE: 10

| | |
|---|---:|
| aaaagatatg gtggggtgct taacagagga ggttagacac cggcgggaac cagaggagcc | 60 |
| caagcgcggc gcctgggcct cggggctgca ggagtcctcg gtgggggtat ggaggtcgcc | 120 |
| ggggaaggag gacggttcag ttgctaggca acccggcctg gacccgcctc tcgctcgcgt | 180 |
| tgctgggaga ctacaaggcc gggaggaggg cggcgaaagg gccctacgtg ctgacgctaa | 240 |
| ttgtatatga gcgcgagcgg cgggctcttg ggtcttttttt agcgccatct gctcgcggcg | 300 |
| ccgcctcctg ctcctcccgc tgctgctgcc gctgccgccc tgagtcactg cctgcgcagc | 360 |
| tccggccgcc tggctcccca tactagtcgc cgatatttgg agttcttaca acatggcaga | 420 |
| cattgacaac aaagaacagt ctgaacttga tcaagatttg gatgatgttg aagaagtaga | 480 |
| agaagaggaa actggtgaag aaacaaaact caaagcacgt cagctaactg ttcagatgat | 540 |
| gcaaaatcct cagattcttg cagcccttca gaaagacttt gatggtctgg tagaaacacc | 600 |
| aacaggatac attgaaagcc tgcctagggt agttaaaaga cgagtgaatg ctctcaaaaa | 660 |
| cctgcaagtt aaatgtgcac agatagaagc caaattctat gaggaagttc acgatcttga | 720 |
| aaggaagtat gctgttctct atcagcctct atttgataag cgatttgaaa ttattaatgc | 780 |
| aatttatgaa cctacggaag aagaatgtga atggaaacca gatgaagaag atgagatttc | 840 |
| ggaggaattg aaagaaaagg ccaagattga agatgagaaa aaagatgaag aaaaagaaga | 900 |
| ccccaaagga attcctgaat tttggttaac tgtttttaag aatgttgact tgctcagtga | 960 |
| tatggttcag gaacacgatg aacctattct gaagcacttg aaagatatta agtgaagtt | 1020 |
| ctcagatgct ggccagccta tgagttttgt cttagaattt cactttgaac ccaatgaata | 1080 |
| ttttacaaat gaagtgctga caaagacata caggatgagg tcagaaccag atgattctga | 1140 |
| tccctttttct tttgatggac cagaaattat gggttgtaca gggtgccaga tagattggaa | 1200 |
| aaaaggaaag aatgtcactt tgaaaactat taagaagaag cagaaacaca agggacgtgg | 1260 |
| gacagttcgt actgtgacta aaacagtttc caatgactct ttctttaact tttttgcccc | 1320 |
| tcctgaagtt cctgagagtg gagatctgga tgatgatgct gaagctatcc ttgctgcaga | 1380 |
| cttcgaaatt ggtcactttt tacgtgagcg tataatccca agatcagtgt tatatttttac | 1440 |
| tggagaagct attgaagatg atgatgatga ttatgatgaa gaaggtgaag aagcggatga | 1500 |
| ggaagggggaa gaagaaggag atgaggaaaa tgatccagac tatgacccaa gaaggatca | 1560 |
| aaacccagca gagtgcaagc agcagtgaag caggatgtat gtggccttga ggataacctg | 1620 |
| cactggtcta ccttctgctt ccctggaaag gatgaattta catcatttga caagcctatt | 1680 |
| ttcaagttat ttgttgtttg tttgcttgtt tttgtttttg cagctaaaat aaaaatttca | 1740 |
| aatacaattt tagttcttac aagataatgt cttaattttg taccaattca ggtagaagta | 1800 |
| gaggcctacc ttgaattaag ggttatactc agttttttaac acattgttga gaaaaggta | 1860 |
| ccagcttggg aacagagatgc tatactaata agcaagtgta aaaaaaaaaa aaaaagagga | 1920 |
| agaaaatctt aagtgattga tgctgttttc ttttaaaaaa aaaaaaaaaa attcattttc | 1980 |

-continued

```
tttgggttag agctagagag aaggccccaa gcttctatgg tttcttctaa ttcttattgc    2040
ttaaagtatg agtatgtcac ttacccgtgc ttctgtttac tgtgtaatta aaatgggtag    2100
tactgtttac ctaactacct catggatgtg ttaaggcata ttgagttaaa tctcatataa    2160
tgtttctcaa tcttgttaaa agctcaaaat tttgggccta tttgtaatgc cagtgtgaca    2220
ctaagcattt tgttcacacc acgctttgat aactaaactg gaaaacaaag gtgttaagta    2280
cctctgttct ggatctgggc agtcagcact cttttagat ctttgtgtgg ctcctatttt     2340
tatagaagtg gagggatgca ctatttcaca aggtccaaga tttgttttca gatattttg     2400 atgactgtat tgtaaatact acagggatag cactatagta ttgtagtcat gagacttaaa    2460
gtggaaataa gactatttt gacaaaagat gccattaaat ttcagactgt agagccacat    2520
ttacaatacc tcaggctaat tactgttaat tttggggttg aactttttt tgacagtgag     2580 ggtggattat tggattgtca ttagaggaag gtctagattt cctgctctta ataaaattac    2640
attgaattga ttttagagg taatgaaaac ttcctttctg agaagttagt gttaaggtct     2700
tggaatgtga acacattgtt tgtagtgcta tccattcctc tcctgagatt ttaacttact    2760
actggaaatc cttaaccaat tataatagct tttttctt attttcaaaa tgatttcctt      2820
tgctttgatt agacactatg tgcttttttt ttttaaccat agttcatcga aatgcagctt    2880
tttctgaact tcaaagatag aatcccattt ttaatgaact gaagtagcaa atcatctttt    2940
ttcattcttt aggaaatagc tattgccaaa gtgaaggtgt agataatacc tagtcttgtt    3000
acataaaggg gatgtggttt gcagaagaat tttctttata aaattgaagt tttaagggac    3060
gtcagtgttt atgccatttt tccagttcca aaatgattcc attccattct agaaatttga    3120
agtatgtaac ctgaaatcct taataaaatt tggatttaat tttataaaat gtactggtga    3180
tattttgggt gttttttttt aaatgaatgt atatactttt tttttgaaga gtggagagta    3240
gtgatgtcta gagggagcta ttttgtgctg aggccactat gttctgtaaa tatataattt    3300
taagagcaac ctcacaatcc ctgctaagtg gagtttatta tttgaagact aaaatggaat    3360
tccatagttc ctgataggtt atattctggg ttattattct gagttatcta caaacatttt    3420
tgagatttgt ctttacactc tgattgtagt ttccagcagc ccatgcacac tgccaagtaa    3480
gtctcatttt ttcctgttag aaatggtgaa atatcatata atcacttata aagaaaactg    3540
atatgaaaaa atttagagt tgtttgcttt atggtcactc aagtagggta agtgttccac    3600
aaattccaca agttgatagt ttaacatgga tgtctgaaag ccacatatat aatttcttag    3660
gattcttaaa ttagtaaatc tagcttactg aagcagtatt agcatcacta ttttagattg    3720
caaaaatacc ttaattgtgt ggaactggct tgtagagtgg tacttaagaa aaatgggatt    3780
ctacctctat ttctgtttta gcacacttaa tcaggaaagg atatattaac tttcataaaa    3840
atatttttgt tgtgtgaata ggttaatgat atggtaaggc ccctaaaata actgaattaa    3900
ttgtttattg taattgtagg ccattcccat tattaaaaat aaagacaaaa cttgaagtaa    3960
ctgaaaatct tatcgtgcta tgtagaaata ttgaactaat attcaaatat ttgaatgctt    4020
tggtttcagg gattggttta aaattggagt ccttttttat gggttagtct tacaaaaatt    4080
taagccttta tatttttgac tttaaatcaa aacaaatgtt attttaaatg tacagaatag    4140
attggtagtg cagaagagtg taagttcttc ataggagctt tagaaaagag aaatatgtgc    4200
taattcagtt ttttttttaat ctgcactgta catatatact tggtaattat gagcttgatt   4260 ttgttttgg aaatatgtgt tcataattta ggtaatttgc tacttaaagc actagtctc      4320 tgatacctga aaagtacatg taaatggtga tggtgaaata atactgcagt taacttaata   4380
```

```
gatgtatact ggtgattttt gtatgctgga ttaaaactcc agatattaaa atataacctg    4440
gataaaaagc c                                                         4451

<210> SEQ ID NO 11
<211> LENGTH: 1530
<212> TYPE: DNA
<213> ORGANISM: Homo sapiens

<400> SEQUENCE: 11
ggcattcaga gagtagatgc cagtcctggg aaaggcaggg gaggagagga gagccacggc      60
tgacgcttgg ggacagaagg aggagcctga ggaggagaca ggacagagcg tctggagagg     120
caggaggaca ccgagttccc cgtgttggcc tccaggtcct gtgcttgcgg agccgtccgg     180
cggctgggat cgagccccga caatgggcaa cgcgcaggag cggccgtcag agactatcga     240
ccgcgagcgg aaacgcctgg tcgagacgct gcaggcggac tcgggactgc tgttggacgc     300
gctgctggcg cggggcgtgc tcaccggggcc agagtacgag gcattggatg cactgcctga     360
tgccgagcgc agggtgcgcc gcctactgct gctggtgcag ggcaagggcg aggccgcctg     420
ccaggagctg ctacgctgtg cccagcgtac cgcgggggcg ccggacccccg cttgggactg     480 gcagcacgct accgggaccg cagctatgac cctccatgcc caggccactg gacgccggag     540
gcacccggct cggggaccac atgcccgggg ttgcccagag cttcagaccc tgacgaggcc     600
gggggccctg agggctccga ggcggtgcaa tccgggaccc cggaggagcc agagccagag     660
ctggaagctg aggcctctaa agaggctgaa ccggagccgg agccagagcc agagctggaa     720
cccgaggctg aagcagaacc agagccggaa ctggagccag aaccggaccc agagcccgag     780
cccgacttcg aggaaaggga cgagtccgaa gattcctgaa ggccagagct ctgacaggcg     840
gtgccccgcc catgctggat aggacctggg atgctgctgg agctgaatcg gatgccacca     900
aggctcggtc cagcccagta ccgctggaag tgaataaact ccggagggtc ggacgggacc     960
tgggctctct ccacgattct ggctgtttgc ccaggaactt agggtgggta cctctgagtc    1020
ccagggacct gggcaggccc aagcccacca cgagcatcat ccagtcctca gccctaatct    1080
gcccttagga gtccaggctg caccctggag atcccaaacc tagcccccta gtgggacaag    1140
gacctgaccc tcctgcccgc atacacaacc catttcccct ggtgagccac ttggcagcat    1200
atgtaggtac cagctcaacc ccacgcaagt tcctgagctg aacatggagc aaggggaggg    1260
tgacttctct ccacataggg agggcttaga gctcacagcc ttgggaagtg agactagaag    1320 agggggagcag aaagggacct tgagtagaca aaggccacac acatcattgt cattactgtt    1380
ttaattgtct ggcttctctc tggactggga gctcagtgag gattctgacc agtgacttac    1440
acaaaaggcg ctctatacat attataatat attcgcttac taaatgaata aggactttcc    1500
aaaaaaaaaa aaaaaaaaa aaaaaaaaa                                       1530

<210> SEQ ID NO 12
<211> LENGTH: 4427
<212> TYPE: DNA
<213> ORGANISM: Homo sapiens

<400> SEQUENCE: 12
cccccggcgg agccagctgc tgctcttcgg tgctggcccc ggtgccggcc ccgttgccca      60
gggaacaggc tccccgcagc cccgcggccc cggagtccat cccgcctcct ccggcccggc     120
ggggccgacg agtccggagg ggctgccgcg ggagccccca ggtttcccta gatgacaaat     180
```

```
aaacattcct tttcctgcgt gaagatagtc tgtggaaacc ttggccatgg catcgatatc    240
agagcctgtt acattcagag agttctgccc gttgtactat ctcctcaatg ccattccgac    300
aaagatccag aagggtttcc gctctatcgt ggtctatctc acggccctcg acaccaacgg    360
ggactacatc gcggtgggca gcagcatcgg catgctctat ctgtactgcc ggcacctcaa    420
ccagatgagg aagtacaact tgaggggaa gacggaatct atcactgtgg tgaagctgct     480
gagctgcttt gatgacctgg tggcagcagg cacagcctct ggcagggttg cagtttttca    540
acttgtatct tcattgccag ggagaaataa acagcttcgg agatttgatg tcactggtat    600
tcacaaaaat agcattacag ctctggcttg gagccccaat ggaatgaaat tgttctctgg    660
agatgacaaa ggcaaaattg tttattcttc tctggatcta gaccaggggc tctgtaactc    720
ccagctggtg ttggaggagc catcttccat tgtgcagctg gattatagcc agaaagtgct    780
gctggtctct actctgcaaa gaagtctgct cttttacact gaagaaaagt ctgtaaggca    840
aattggaaca caaccaagga aaagtactgg gaaatttggt gcttgtttta taccaggact    900
ctgtaagcaa agtgatctaa ccttgtatgc gtcacggccc gggctccggc tatggaaggc    960
tgatgtccac gggactgttc aagccacgtt tatcttaaaa gatgcttttg ccggggagt    1020 caagcctttt gaactgcacc cgcgtctgga atccccaac agtggaagtt gcagcttacc    1080
tgagaggcac ctgggcttg tttcatgttt ctttcaagaa ggctgggtgc tgagttggaa    1140
tgaatatagt atctatctcc tagacacagt caaccaggcc acagttgctg gtttggaagg    1200
atccggtgat attgtgtctg tttcgtgcac agaaaatgaa atattttcct tgaaaggaga    1260
taggaacatt ataagaattt caagcaggcc tgaaggatta acatcaacag tgagagatgg    1320
tctggagatg tctggatgct cagagcgtgt ccacgtgcag caagcggaga gctgccagg    1380 ggccacagtt tctgagacga ggctcagagg ctcttccatg ccagctccg tggccagcga    1440 gccaaggagc aggagcagct cgctcaactc caccgacagc ggctccgggc tcctgcccc    1500 tgggctccag gccaccccctg agctgggcaa gggcagccag ccctgtcac agagattcaa    1560 cgccatcagc tcagaggact ttgaccagga gcttgtcgtg aagcctatca agtgaaaag    1620 gaagaagaag aagaagaaga cagaaggtgg aagcaggagc acctgtcaca gctccctgga    1680
atcgacaccc tgctccgaat tcctgggga cagtccccag tccttgaaca cagacttgct    1740
gtcgatgacc tcaagtgtcc tgggcagtag cgtggatcag ttaagtgcag agtctccaga    1800
ccaggaaagc agcttcaatg gtgaagtgaa cggtgtccca caggaaaata ctgaccccga    1860 aacgttaat gtcctggagg tgtcaggatc aatgcctgat tctctggctg aggaagatga    1920
cattagaact gaaatgccac actgtcacca tgcacatggg cgggagctgc tcaatggagc    1980
gagggaagat gtgggaggca gtgatgtcac gggactcgga gatgagccgt gtcctgcaga    2040
tgatggacca aatagcacac agttaccctt ccaagaacag acagctctc ctggggcgca     2100 tgatggggaa gacatccaac ccattggccc ccaaagcact ttttgtgaag tcccctcct    2160 gaactcactc actgtgcctt ccagcctcag ctggccccca agtgctgaac agtggctgcc    2220
tgggaccaga gctgatgaag gcagccccgt ggagcccagc caagagcagg acatcctaac    2280
cagcatggag gcctctggcc acctcagcac aaatctctgg catgctgtca ctgatgatga    2340
cacaggtcag aaagaaatac ccatttctga acgtgtcttg gggagtgtgg gaggacagct    2400
gactccggtc tctgccttgg cagccagcac tcacaagccc tggcttgagc agcctccacg    2460
ggatcagaca ttgacgtcca gcgatgagga ggacatctat gcccacgggc ttccttcttc    2520
atcctcagag acgagtgtga cagagctcgg acctagttgc tcccagcagg acctgagccg    2580
```

```
gctgggtgca gaggacgccg ggctgctcaa gccagatcag tttgcagaaa gctggatggg    2640
ctactcgggt cccggctatg gcatcctcag cttggtggtc tccgagaagt atatctggtg    2700
cctggactac aaaggcggcc tgttctgcag cgcgttgccg ggcgccgggc tgcgctggca    2760
gaagtttgaa gatgctgtcc agcaggtggc agtctcgccc tcaggagccc ttctctggaa    2820
gattgaacag aaatctaacc gggcttttgc ttgtgggaaa gtcaccatca aggggaagcg    2880
gcactggtac gaagccctgc cccaggcagt gtttgtggcc ctgagcgatg acacggcctg    2940
gatcatcagg accagtgggg acctatactt gcagacaggt ctgagcgtgg atcgcccttg    3000
tgccagagcc gtaaaggtgg actgtcccta cccgctgtcc cagatcacag cccggaacaa    3060
tgtggtgtgg gcgctgacag agcagagggc cctcctgtac cgggagggcg tgagcagctt    3120
ctgtccggaa ggcgagcagt ggaagtgtga cattgtcagc gaaaggcaag ctttagaacc    3180
cgtctgcata acgctcgggg atcagcagac tctctgggcc ctggacatcc atgggaacct    3240
gtggttcaga actggcatta tttccaagaa gccccaagga gatgacgacc attggtggca    3300
agtgagcatc acggactatg tggtgtttga ccagtgcagc ttatttcaga cgataatcca    3360
tgccactcac tcggtggcca cagcagccca agccccgta gaaaaggtgg cagataagct    3420
gcgcatggcg ttttggtccc agcagcttca gtgccagcca agccttctcg gggtcaataa    3480
cagcggtgtc tggatctcct cgggcaagaa tgaattccac gtcgctaagg gaagtctcat    3540
aggcacctac tggaatcatg tggttccccg tgggacagct tctgctacaa aatgggcctt    3600
tgtgttggct tctgcagctc ccacgaagga aggaagcttc ctgtggctgt gccagagcag    3660
caaggacctg tgcagcgtca gcgcccagag cgcacagtcg cggccctcca cggtgcagct    3720
gcctcccgaa gccgagatgc gcgcctatgc cgcctgccag gatgcgctgt gggcgctgga    3780
cagcctcggc caggtgttca tcaggacgct ctccaagagc tgccccacgg gcatgcactg    3840
gaccaggctg gacctctccc agctaggagc tgtaaaattg acaagcttgg catgtggaaa    3900
tcagcacatc tgggcctgtg attccagggg tggagtttac ttccgtgtag ggactcagcc    3960
tctcaatccc agtctcatgc ttccagcctg gataatgatt gagccacctg tccaggtaag    4020
cagaagttag ctggtggaac tcactcttca gtaagacaga aactgtgagg atgctggtac    4080
tgggaaaaag gatctgcaca gcctctagag gcctcccagc aaatgcgggg agccatgccc    4140
ccagggtcta cacactctcg ttcatcaaca tcacaactgg aattcgggat ttgtgaagtt    4200
tagagctgaa cagactgtta cagattatga gtcaacacgt atattttctc tttcaaaata    4260
ataatatttc gtttttgact ttttactaag tgaatattat tttttaaatc tgcctatata    4320
ttggaacctc tattttataa taataatgat aataaatcag tacccagaag tataaagaag    4380
gtaaaagtta ctttgaaaaa aaaaaaaaaa aaaaaaaaa aaaaaaa                    4427
```

PREDICTING PEPTIDE RECEPTOR RADIOTHERAPY USING A GENE EXPRESSION ASSAY

CROSS-REFERENCE TO RELATED APPLICATIONS

This application claims priority to, and the benefit of, U.S. Provisional Application No. 62/592,647, filed Nov. 30, 2017, the contents of which is incorporated herein by reference in its entirety.

SEQUENCE LISTING

The instant application contains a Sequence Listing which has been submitted in ASCII format via EFS-Web and is hereby incorporated by reference in its entirety. Said ASCII copy, created on Nov. 15, 2018, is named "LBIO-003_001US_ST25.txt" and is 52,601 bytes in size.

FIELD OF THE INVENTION

The present invention relates to the prediction of response to peptide receptor radiotherapy (PRRT) using a gene expression assay.

BACKGROUND OF THE INVENTION

The most commonly used form of radionuclide therapy in neuroendocrine tumors is peptide receptor radionuclide therapy (PRRT). This utilizes the overexpression of somatostatin receptors that are a central feature of NETs. PRRT uses an analog of somatostatin, octreotide, as a peptide to target the receptors. Radiolabeled derivatives of this analog include $^{177}$Lu-DOTA-Tyr$^3$,Thr$^8$-octreotide or $^{177}$Lu-octreotate. This therapeutic strategy is widely used in Europe and has more recently been introduced into the USA.

Diverse non-controlled studies in pancreatic and bronchopulmonary NETs have demonstrated that $^{177}$Lu-octreotate is effective with objective responses and a positive impact on survival parameters. Most recently a phase III, randomized, controlled trial of midgut NETs progressive on standard octreotide LAR treatment (NETTER-1) demonstrated $^{177}$Lu-octreotate to be more effective than high-dose octreotide somatostatin analogs.

The decision to use PRRT is currently made on the basis of somatostatin receptor (SSR) expression levels. Information is usually obtained either by tissue biopsy and immunohistochemistry or by a somatostatin-based scan like an $^{111}$In-pentetreotide scan or a $^{68}$Ga-DOTATATE/DOTATOC PET/CT.

Immunohistochemistry is, however, limited since somatostatin receptor expression is heterogeneous in tumors, individual antibodies can have different binding affinities and assessment of staining by a pathologist does not provide an objective output. Further limiting factors include the inability to define receptor functionality and to determine expression in other tumors that are not biopsied.

Assessment of somatostatin expression using imaging involves comparing a radioactive uptake on a target lesion with a non-tumor organ like the spleen. The degree of uptake is graded from low to intensely positive per the Krenning grade. This approach has low predictive activity, however. For example, an intensely positive tumor—Krenning grade 4, at $^{111}$In-pentetreotide scan—only has a 60% accuracy of responding. Various semi-quantitative tools have been attempted but all have failed. Somatostatin receptor expression is useful for identifying whether a tumor can be targetable and isotope delivered but it does not provide an accurate assessment of the likelihood of radiation susceptibility (and therapeutic efficacy).

Other clinical parameters (such as extent of disease), tumor grading and biomarkers (such as chromogranin A) have been investigated as potential predictive tools. None, however, have proven effective as robust predictors of the effect of therapy, although grading using morphological criteria or KI67 evaluation has demonstrated some clinical utility. The accuracy of grading is about 70% for predicting PRRT. Typically, low grade tumors (well-differentiated grade 1 or 2 i.e., KI67 detectable in ≤20% of tumor cells) respond to PRRT more often than high grade (KI67>20%) tumors. Grading, however, is limited by tumor heterogeneity, subjective observer variations and a low kappa value. Furthermore, tissue biopsies are rarely obtained from more than one location and metastases often differ significantly from the primary lesion biopsied for diagnosis.

It is evident that the complexity of the molecular drivers in tumor cells that define responsiveness to therapy in cancer or disease progression require more sophisticated assessment tools. The development of technologies based upon the delineation of the molecular biology of diverse cancers has led to the evolution of strategies to evaluate circulating molecular information emanating from neoplasia. Such strategies or "liquid biopsies", have proven remarkably effective in lung neoplasia e.g., for monitoring treatment responses to EFGR inhibitors through identification of mutation T790M in circulating tumor DNA. The opportunity to limit biopsies, define potential therapeutic targets and to provide a real-time monitoring tool to evaluate disease evolution has considerable clinical allure.

SUMMARY OF THE INVENTION

The present disclosure provides a method of providing a peptide receptor radiotherapy (PRRT) treatment recommendation for a subject having a neuroendocrine tumor (NET), the method comprising: determining the expression level of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and providing a recommendation that the NET will respond to PRRT when the third score is equal to or less than a second predetermined cutoff value, or providing a recommendation that the NET will not respond to PRRT when the third score is above the second predetermined cutoff value.

In the preceding method of the present disclosure, a first predetermined cutoff value can be 5.9. The second predetermined cutoff value can be 0.

The present disclosure provides a method of providing a peptide receptor radiotherapy (PRRT) treatment recommendation for a subject having a neuroendocrine tumor (NET), the method comprising: determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2 PLD3, NAP1L1, NOL3, and TECPR2, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and providing a recommendation that the NET will respond to PRRT when the third score is equal to or less than a second predetermined cutoff value, or providing a recommendation that the NET will not respond to PRRT when the third score is above the second predetermined cutoff value.

In the preceding method of the present disclosure, a first predetermined cutoff value can be 10.9. A second predetermined cutoff value can be 0.

The present disclosure provides a method of providing a peptide receptor radiotherapy (PRRT) treatment recommendation for a subject having a neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2 thereby obtaining a summated expression level; and providing a recommendation that the NET will respond to PRRT when the summated expression level is equal to or greater than a predetermined cutoff value, or providing a recommendation that the NET will not respond to PRRT when the summated expression level is less than the predetermined cutoff value.

In the preceding method of the present disclosure, the predetermined cutoff value can be 10.9.

The present disclosure provides a method of providing a peptide receptor radiotherapy (PRRT) treatment recommendation for a subject having a low grade or high grade neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; and providing a recommendation that the low grade or high grade NET will respond to PRRT when the summated expression level is equal to or greater than a predetermined cutoff value, or providing a recommendation that the low grade or high grade NET will not respond to PRRT when the summated expression level is less than the predetermined cutoff value.

In the preceding method of the present disclosure, wherein the predetermined cutoff value cam be 10.9.

The present disclosure provides a method of providing a peptide receptor radiotherapy (PRRT) treatment recommendation for a subject having a low grade or high grade neuroendocrine tumor (NET), the method comprising: determining the expression level of each of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; and providing a recommendation that the low grade or high grade NET will respond to PRRT when the summated expression level is equal to or greater than a predetermined cutoff value, or providing a recommendation that the low grade or high grade NET will not respond to PRRT when the summated expression level is less than the predetermined cutoff value.

In methods of the present disclosure, at least one of the at least 9 biomarkers can be RNA, cDNA, or protein. In aspects wherein a biomarker is RNA, the RNA can be reverse transcribed to produce cDNA, and the produced cDNA expression level can be detected. In aspects wherein a biomarker is protein, the protein can be detected by forming a complex between the biomarker and a labeled probe or primer.

In methods of the present disclosure, expression level of a biomarker can be detected by forming a complex between a biomarker and a labeled probe or primer.

In methods of the present disclosure, when a biomarker is RNA or cDNA, the RNA or cDNA can be detected by forming a complex between the RNA or cDNA and a labeled nucleic acid probe or primer. A complex between the RNA or cDNA and the labeled nucleic acid probe or primer can be a hybridization complex.

In methods of the present disclosure, a test sample can be blood, serum, plasma, or neoplastic tissue. In methods of the present disclosure, the test sample can be blood.

In methods of the present disclosure, a NET can be designated high grade when the NET is poorly differentiated.

In methods of the present disclosure, a NET can be designated low grade when the NET is well differentiated, bronchial typical carcinoid, or bronchial atypical carcinoid.

Methods of the present disclosure can further comprise administering PRRT to the subject when the third score is equal to or less than the second predetermined cutoff value.

Methods of the present disclosure can further comprise administering PRRT to the subject when the summated expression level is equal to or greater than the predetermined cutoff value.

Methods of the present disclosure can have a sensitivity of greater than 90%. Methods of the present disclosure can have a specificity of greater than 90%.

The present disclosure provides a method of treating a subject with peptide receptor radiotherapy (PRRT), wherein the subject has a neuroendocrine tumor (NET), the method comprising: determining the expression level of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value.

The present disclosure provides a method of treating a subject with peptide receptor radiotherapy (PRRT), wherein the subject has a neuroendocrine tumor (NET), the method comprising: determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value.

The present disclosure provides a method of treating a subject with peptide receptor radiotherapy (PRRT), wherein the subject has a neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2 thereby obtaining a summated expression level; and administering PRRT to the subject when the summated expression level is equal to or greater than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; and administering PRRT to the subject when the summated expression level is equal to or greater than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; and administering PRRT to the subject when the summated expression level is equal to or greater than the predetermined cutoff value.

In methods of the present disclosure, administering PRRT to the subject can comprise administering a $^{177}$Lu-based-PRRT. A $^{177}$Lu-based-PRRT can be $^{177}$Lu-DOTA-Tyr$^3$-Thr$^8$-octreotide.

In methods of the present disclosure, $^{177}$Lu-DOTA-Tyr$^3$-Thr$^8$-octreotide can be administered at a dose of about 7.4 GBq (200 mCi) about once every 8 weeks for a total of about 4 doses. $^{177}$Lu-DOTA-Tyr$^3$-Thr$^8$-octreotide can be administered at a dose of about 6.5 GBq about once every 8 weeks for a total of about 4 doses. $^{177}$Lu-DOTA-Tyr$^3$-Thr$^8$-octreotide can be administered at a dose of about 4.6 GBq about once every 8 weeks for a total of about 4 doses. $^{177}$Lu-DOTA-Tyr$^3$-Thr$^8$-octreotide can be administered at a dose of about 3.2 GBq (100 mCi) about once every 8 weeks for a total of about 4 doses. $^{177}$Lu-DOTA-Tyr$^3$-Thr$^8$-octreotide can be administered at a dose of about 3.7 GBq about once every 8 weeks for a total of about 4 doses.

In methods of the present disclosure, $^{177}$Lu-based-PRRT can be administered intravenously. $^{177}$Lu-based-PRRT can be administered intra-arterially.

In some embodiments of any one of the above aspects, the method further comprises administering PRRT to the subject when it's predicted that the NET will respond to PRRT.

Any of the above aspects can be combined with any other aspect.

Unless otherwise defined, all technical and scientific terms used herein have the same meaning as commonly understood by one of ordinary skill in the art to which this disclosure belongs. In the Specification, the singular forms also include the plural unless the context clearly dictates otherwise; as examples, the terms "a," "an," and "the" are understood to be singular or plural and the term "or" is understood to be inclusive. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

Although methods and materials similar or equivalent to those described herein can be used in the practice or testing of the present disclosure, suitable methods and materials are described below. All publications, patent applications, patents, and other references mentioned herein are incorporated by reference in their entirety. The references cited herein are not admitted to be prior art to the claimed invention. In the case of conflict, the present Specification, including definitions, will control. In addition, the materials, methods, and examples are illustrative only and are not intended to be limiting. Other features and advantages of the disclosure will be apparent from the following detailed description and claim.

BRIEF DESCRIPTION OF THE DRAWINGS

FIG. 6A shows PPQ in PRRT and comparator cohorts in Biomarker positive cases. In prediction-responders i.e., PPQ "positive" groups, the mPFS was not reached in PRRT treated patients (Validation Cohort I (n=44) and Validation Cohort II (n=42)) compared to those treated with SSAs or in the Registry.

FIG. 6B shows PPQ in PRRT and comparator cohorts in Biomarker negative cases: In prediction-non-responders i.e., PPQ "negative" groups, the mPFS was similar irrespective of treatment with PRRT or not.

FIG. 6C shows ideal Predictive Biomarker "Positive": In this idealized example, a "treatment effect" i.e., a quantitative difference in mPFS is noted between those undergoing treatment (mPFS undefined) and those not undergoing treatment (17 months).

FIG. 6D shows ideal Predictive Biomarker "Negative": In this idealized example, the mPFS is the same (18 months) irrespective of treatment.

DETAILED DESCRIPTION OF THE INVENTION

Figure 1:
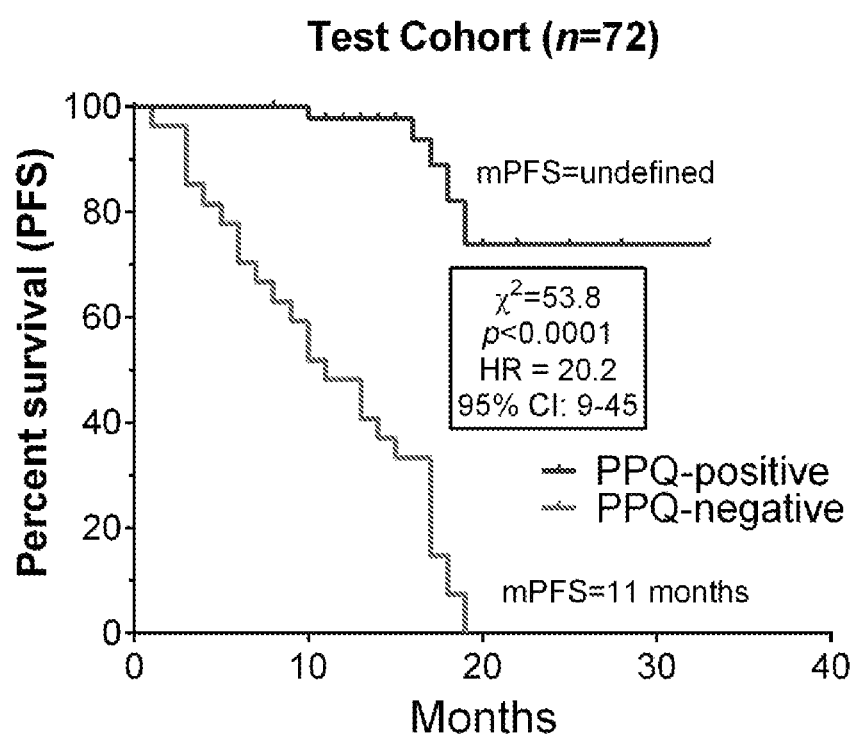
FIG. 1 is a graph showing the utility of the PRRT prediction quotient for predicting PFS in the test cohort. Test cohort (n=72): In patients predicted to respond pre-therapy by the PPQ (biomarker positive), mPFS was not reached. For those predicted not to respond (biomarker negative), the mPFS was 8 months. This was significantly different (HR 36.4, p<0.0001).

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs. All patents and publications cited in this specification are incorporated herein by reference in their entireties.

This invention is based, in part, on the discovery that the expression levels of circulating neuroendocrine tumor (NET) transcripts can predict whether a patient with a NET will respond to peptide receptor radiotherapy (PRRT). The circulating NET transcripts include the following: (a) growth factor (GF)-related genes (ARAF1, BRAF, KRAS and RAF-1); and (b) genes involved in metabolism (M) (ATP6V1H, OAZ2, PANK2 and PLD3). The expression levels of these genes can be normalized to ALG9, which serves as a housekeeping gene. It was discovered that when the summated expression level (post normalization) of ARAF1, BRAF, KRAS, RAF-1, ATP6V1H, OAZ2, PANK2, PLD3 is equal to or greater than a predetermined cutoff value, the NET will respond to PRRT, regardless of the histological grade of the NET. In addition, when the summated expression level (post normalization) of ARAF1, BRAF, KRAS, RAF-1, ATP6V1H, OAZ2, PANK2, PLD3 is less than a predetermined cutoff value, the NET will not respond to PRRT, regardless of the histological grade of the NET. In some embodiments, the circulating NET transcripts can further include genes involved in proliferation (P) (NAP1L1, NOL3, and TECPR2). The expression levels of NAP1L1, NOL3, and TECPR2 can also be measured and normalized to the expression level of ALG9.

In some embodiments, the summated expression level of ARAF1, BRAF, KRAS, RAF-1, ATP6V1H, OAZ2, PANK2, PLD3 can be obtained by implementing the following steps: (a1) determining the expression level of each of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; (b1) normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; and (c1) summing the normalized expression level of each of ARAF1, BRAF, KRAS, RAF-1, ATP6V1H, OAZ2, PANK2, and PLD3, thereby obtaining a summated expression level.

Alternatively, the summated expression level of ARAF1, BRAF, KRAS, RAF-1, ATP6V1H, OAZ2, PANK2, PLD3 can also be obtained by implementing the following steps after the expression level of each of the at least 9 biomarkers is determined: (a2) summing the expression level of each of ARAF1, BRAF, KRAS, RAF-1, ATP6V1H, OAZ2, PANK2, and PLD3, thereby obtaining a summated value; and (b2) normalizing the summated value to the expression level of ALG9, thereby obtaining a summated expression level.

One aspect of the present disclosure provides a method of providing a PRRT treatment recommendation for a subject having a low grade or high grade NET, the method comprising providing a recommendation that the low grade or high grade NET will respond to PRRT when the summated expression level of ARAF1, BRAF, KRAS, RAF-1, ATP6V1H, OAZ2, PANK2, PLD3 is equal to or greater than a predetermined cutoff value, or providing a recommendation that the low grade or high grade NET will not respond to PRRT when the summated expression level is less than the predetermined cutoff value. In some embodiments, the NET is designated high grade when the NET is poorly differentiated. In some embodiments, the NET is designated low grade when the NET is well differentiated, bronchial typical carcinoid, or bronchial atypical carcinoid.

In a similar aspect, the present disclosure provides a method of providing a PRRT treatment recommendation for a subject having a NET, the method comprising providing a recommendation that the NET will respond to PRRT when the summated expression level of ARAF1, BRAF, KRAS, RAF-1, ATP6V1H, OAZ2, PANK2, PLD3 is equal to or greater than a predetermined cutoff value, or providing a recommendation that the NET will not respond to PRRT when the summated expression level is less than the predetermined cutoff value.

In some embodiments, the predetermined cutoff value is 5.9. This cutoff value is derived from a scenario where the summated expression level of ARAF1, BRAF, KRAS, RAF-1, ATP6V1H, OAZ2, PANK2, PLD3 is 5.9 times the expression level of ALG9.

In another aspect, the histological grade of the NET can also be used in conjunction with the expression levels of the circulating neuroendocrine tumor transcripts. Accordingly, the present disclosure provides a method of providing a PRRT treatment recommendation for a subject having a NET, the method comprising: (a3) determining a first score, wherein the first score is 1 when the summated expression level of ARAF1, BRAF, KRAS, RAF-1, ATP6V1H, OAZ2, PANK2, PLD3 is equal to or greater than a first predetermined cutoff value, or the first score is 0 when the summated expression level is below the first predetermined cutoff value; (b3) determining a second score based on the histological grade of the NET, wherein the second score is 1 when the NET is designated high grade, or the second score is 0 when the NET is designated low grade; (c3) calculating a third score based on the following equation: Third Score=39.22787−40.80341*(First Score)−18.441*(Second Score); and (d3) providing a recommendation that the NET will respond to PRRT when the third score is equal to or less than a second predetermined cutoff value, or providing a recommendation that the NET will not respond to PRRT when the third score is above the second predetermined cutoff value.

In some embodiments, the first predetermined cutoff value is 5.9. This cutoff value is derived from a scenario where the summated expression level of ARAF1, BRAF, KRAS, RAF-1, ATP6V1H, OAZ2, PANK2, PLD3 is 5.9 times the expression level of ALG9.

In some embodiments, the second predetermined cutoff value is 0.

In one aspect, the present disclosure provides a method of providing a PRRT treatment recommendation for a subject having a low grade or high grade NET, the method comprising: (a) determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; (b) normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; (c) summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; and (d) providing a recommendation that the low grade or high grade NET will respond to PRRT when the summated expression level is equal to or greater than a predetermined cutoff value, or providing a recommendation that the low grade or high grade NET will not respond to PRRT when the summated expression level is less than the predetermined cutoff value. In some embodiments, the predetermined cutoff value is 10.9.

In another aspect, the present disclosure provides a method of providing a PRRT treatment recommendation for a subject having a NET, the method comprising: (a) determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; (b) normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; (c) summing the normalized expression level of each of ARAF1, BRAF, KRAS, RAF-1, ATP6V1H, OAZ2, PANK2, PLD3, NAP1L1, NOL3, and TECPR2 thereby obtaining a summated expression level; and (d) providing a recommendation that the NET will respond to PRRT when the summated expression level is equal to or greater than a predetermined cutoff value, or providing a recommendation that the NET will not respond to PRRT when the summated expression level is less than the predetermined cutoff value. In some embodiments, the predetermined cutoff value is 10.9.

In another aspect, the present disclosure provides a method of providing a PRRT treatment recommendation for a subject having a NET, the method comprising: (a) determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; (b) normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; (c) summing the normalized expression level of each of ARAF1, BRAF, KRAS, RAF-1, ATP6V1H, OAZ2, PANK2 PLD3, NAP1L1, NOL3, and TECPR2, thereby obtaining a summated expression level; (d) determining a first score, wherein the first score is 1 when the summated expression level is equal to or greater than a first predetermined cutoff value, or the first score is 0 when the summated expression level is below the first predetermined cutoff value; (e) determining a second score based on the histological grade of the NET, wherein the second score is 1 when the NET is designated high grade, or the second score is 0 when the NET is designated low grade; (f) calculating a third score based on the following equation: Third Score=39.22787−40.80341*(First Score)−18.441*(Second Score); and (f) providing a recommendation that the NET will respond to PRRT when the third score is equal to or less than a second predetermined cutoff value, or providing a recommendation that the NET will not respond to PRRT when the third score is above the second predetermined cutoff value. In some embodiments, the first predetermined cutoff value is 10.9. In some embodiments, the second predetermined cutoff value is 0.

A responder (i.e., the NET will respond to PRRT) refers to an individual predicted by the methods described herein as achieving disease stabilization or demonstrating a partial response. A non-responder (i.e., the NET will not respond to PRRT) refers to an individual exhibiting progressive disease.

The test sample can be any biological fluid obtained from the subject. Preferably, the test sample is blood, serum, plasma or neoplastic tissue. In some embodiments, the test sample is blood. In some embodiments, the test sample is serum. In some embodiments, the test sample is plasma.

The expression level can be measured in a number of ways, including, but not limited to: measuring the mRNA encoded by the selected genes; measuring the amount of protein encoded by the selected genes; and measuring the activity of the protein encoded by the selected genes.

The biomarker can be RNA, cDNA, or protein. When the biomarker is RNA, the RNA can be reverse transcribed to produce cDNA (such as by RT-PCR, and the produced cDNA expression level is detected. The expression level of the biomarker can be detected by forming a complex between the biomarker and a labeled probe or primer. When the biomarker is RNA or cDNA, the RNA or cDNA detected by forming a complex between the RNA or cDNA and a labeled nucleic acid probe or primer. The complex between the RNA or cDNA and the labeled nucleic acid probe or primer can be a hybridization complex.

Gene expression can also be detected by microarray analysis. Differential gene expression can also be identified, or confirmed using the microarray technique. Thus, the expression profile biomarkers can be measured in either fresh or fixed tissue, using microarray technology. In this method, polynucleotide sequences of interest (including cDNAs and oligonucleotides) are plated, or arrayed, on a microchip substrate. The arrayed sequences are then hybridized with specific DNA probes from cells or tissues of interest. The source of mRNA typically is total RNA isolated from a biological sample, and corresponding normal tissues or cell lines may be used to determine differential expression.

In some embodiments of the microarray technique, PCR amplified inserts of cDNA clones are applied to a substrate in a dense array. Preferably at least 10,000 nucleotide sequences are applied to the substrate. The microarrayed genes, immobilized on the microchip at 10,000 elements each, are suitable for hybridization under stringent conditions. Fluorescently labeled cDNA probes may be generated through incorporation of fluorescent nucleotides by reverse transcription of RNA extracted from tissues of interest. Labeled cDNA probes applied to the chip hybridize with specificity to each spot of DNA on the array. After stringent washing to remove non-specifically bound probes, the microarray chip is scanned by a device such as, confocal laser microscopy or by another detection method, such as a CCD camera. Quantitation of hybridization of each arrayed element allows for assessment of corresponding mRNA abundance. With dual color fluorescence, separately labeled cDNA probes generated from two sources of RNA are hybridized pair-wise to the array. The relative abundance of the transcripts from the two sources corresponding to each specified gene is thus determined simultaneously. Microarray analysis can be performed by commercially available equipment, following manufacturer's protocols.

In some embodiments, the biomarkers can be detected in a biological sample using qRT-PCR. The first step in gene expression profiling by RT-PCR is extracting RNA from a biological sample followed by the reverse transcription of the RNA template into cDNA and amplification by a PCR reaction. The reverse transcription reaction step is generally primed using specific primers, random hexamers, or oligo-dT primers, depending on the goal of expression profiling. The two commonly used reverse transcriptases are avilo myeloblastosis virus reverse transcriptase (AMV-RT) and Moloney murine leukemia virus reverse transcriptase (MLV-RT).

When the biomarker is protein, the protein can be detected by forming a complex between the protein and a labeled antibody. The label can be any label for example a fluorescent label, chemiluminescence label, radioactive label, etc. Exemplary methods for protein detection include, but are not limited to, enzyme immunoassay (EIA), radioimmunoassay (MA), Western blot analysis and enzyme linked immunoabsorbant assay (ELISA). For example, the biomarker can be detected in an ELISA, in which the biomarker antibody is bound to a solid phase and an enzyme-antibody conjugate is employed to detect and/or quantify biomarker present in a sample. Alternatively, a western blot assay can be used in which solubilized and separated biomarker is bound to nitrocellulose paper. The combination of a highly specific, stable liquid conjugate with a sensitive chromogenic substrate allows rapid and accurate identification of samples.

In some embodiments, the methods described herein further comprise administering PRRT to the subject when it's predicted that the NET will respond to PRRT. For example, in accordance with some aspects of the present disclosure, the method further comprises administering PRRT to the subject when the summated expression level is equal to or greater than the predetermined cutoff value. In accordance with other aspects of the present disclosure, the method further comprises administering PRRT to the subject when the third score is equal to or less than the second predetermined cutoff value. In PRRT, a cell-targeting protein (or peptide) called octreotide is combined with a small amount of radioactive material, or radionuclide, creating a special type of radiopharmaceutical called a radiopeptide. When injected into the patient's bloodstream, this radiopeptide travels to and binds to neuroendocrine tumor cells, delivering a high dose of radiation to the cancer.

When it's predicted that the NET will not respond to PRRT, the methods described herein further comprise monitoring the subject over a period of time, e.g., 1-6 months.

In some embodiments, the methods described herein can have a specificity, sensitivity, and/or accuracy of at least 75%, 80%, 85%, 90%, 91%, 92%, 93%, 94%, 95%, 96%, 97%, 98%, or 99%.

The present disclosure provides a method of treating a subject with peptide receptor radiotherapy (PRRT), wherein the subject has a neuroendocrine tumor (NET), the method comprising: determining the expression level of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value.

The present disclosure provides a method of treating a subject with peptide receptor radiotherapy (PRRT), wherein the subject has a neuroendocrine tumor (NET), the method comprising: determining the expression level of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value or administering an alternative form of therapy to the subject when the third score is less than the predetermined cutoff value.

The present disclosure provides a method of treating a subject with peptide receptor radiotherapy (PRRT), wherein the subject has a neuroendocrine tumor (NET), the method comprising: determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2 PLD3, NAP1L1, NOL3, and TECPR2, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value.

The present disclosure provides a method of treating a subject with peptide receptor radiotherapy (PRRT), wherein the subject has a neuroendocrine tumor (NET), the method comprising: determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2 PLD3, NAP1L1, NOL3, and TECPR2, thereby obtaining a summated expression level; determining a first score, wherein the first score is 1 when the summated expression level is equal to or greater than a first predetermined cutoff value, or the first score is 0 when the summated expression level is below the first predetermined cutoff value; determining a second score based on the histological grade of the NET, wherein the second score is 1 when the NET is designated high grade, or the second score is 0 when the NET is designated low grade; calculating a third score based on the following equation: Third Score=39.22787−40.80341*(First Score)−18.441*(Second Score); and administering PRRT to the subject when the third score is equal to or greater than the predetermined cutoff value or administering an alternative form of therapy to the subject when the third score is less than the predetermined cutoff value.

The present disclosure provides a method of treating a subject with peptide receptor radiotherapy (PRRT), wherein the subject has a neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2 thereby obtaining a summated expression level; and administering PRRT to the subject when the summated expression level is equal to or greater than the predetermined cutoff value.

The present disclosure provides a method of treating a subject with peptide receptor radiotherapy (PRRT), wherein the subject has a neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2 thereby obtaining a summated expression level; and administering PRRT to the subject when the summated expression level is equal to or greater than the predetermined cutoff value or administering an alternative form of therapy to the subject when the summated expression level is less than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; and administering PRRT to the subject when the summated expression level is equal to or greater than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9; normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2; summing the normalized expression level of each of ARAF1, BRAF, KRAS, RAF-1, ATP6V1H, OAZ2, PANK2, PLD3, NAP1L1, NOL3, and TECPR2, thereby obtaining a summated expression level; and administering PRRT to the subject when the summated expression level is equal to or greater than the predetermined cutoff value or administering an alternative form of therapy to the subject when the summated expression level is less than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; and administering PRRT to the subject when the summated expression level is equal to or greater than the predetermined cutoff value.

The present disclosure provides a method of treating a subject with peptide receptor radiotherapy (PRRT), wherein the subject has a low grade or high grade neuroendocrine tumor (NET), the method comprising: determining the expression level of each of at least 9 biomarkers from a test sample from the subject by contacting the test sample with a plurality of agents specific to detect the expression of the at least 9 biomarkers, wherein the 9 biomarkers comprise ARAF1, BRAF, KRAS, RAF-1, ATP6V1H, OAZ2, PANK2, PLD3, and ALG9; normalizing the expression level of each of ARAF1, BRAF, KRAS, RAF-1, ATP6V1H, OAZ2, PANK2, and PLD3 to the expression level of ALG9, thereby obtaining a normalized expression level of each of ARAF1, BRAF, KRAS, RAF-1, ATP6V1H, OAZ2, PANK2, and PLD3; summing the normalized expression level of each of ARAF1, BRAF, KRAS, RAF-1, ATP6V1H, OAZ2, PANK2, and PLD3, thereby obtaining a summated expression level; and administering PRRT to the subject when the summated expression level is equal to or greater than the predetermined cutoff value or administering an alternative form of therapy to the subject when the summated expression level is less than the predetermined cutoff value.

In methods of the present disclosure, administering PRRT to the subject can comprise administering a $^{177}$Lu-based-PRRT. A $^{177}$Lu-based-PRRT can be $^{177}$Lu-DOTA-Tyr$^3$-Thr$^8$-octreotide (Lutathera).

In methods of the present disclosure, $^{177}$Lu-DOTA-Tyr$^3$-Thr$^8$-octreotide can be administered at a dose of about 7.4 GBq (200 mCi) about once every 8 weeks for a total of about 4 doses. $^{177}$Lu-DOTA-Tyr$^3$-Thr$^8$-octreotide can be administered at a dose of about 6.5 GBq about once every 8 weeks for a total of about 4 doses. $^{177}$Lu-DOTA-Tyr$^3$-Thr$^8$-octreotide can be administered at a dose of about 4.6 GBq about once every 8 weeks for a total of about 4 doses. $^{177}$Lu-DOTA-Tyr$^3$-Thr$^8$-octreotide can be administered at a dose of about 3.2 GBq (100 mCi) about once every 8 weeks for a total of about 4 doses. $^{177}$Lu-DOTA-Tyr$^3$-Thr$^8$-octreotide can be administered at a dose of about 3.7 GBq about once every 8 weeks for a total of about 4 doses.

In methods of the present disclosure, PRRT can be administered intravenously. Alternatively, PRRT can be administered intra-arterially.

In methods of the present disclosure, $^{177}$Lu-based-PRRT can be administered intravenously. Alternatively, $^{177}$Lu-based-PRRT can be administered intra-arterially.

In methods of the present disclosure, an alternative form of therapy can comprise administering chemotherapy to a subject. An alternative form of therapy can comprise administering immunotherapy to a subject. An alternative form of therapy can comprise administering radiation therapy to a subject. An alternative form of therapy can comprise administering a combination of PRRT and chemotherapy to a subject. An alternative form of therapy can comprise administering a combination of PRRT and immunotherapy to a subject. An alternative form of therapy can comprise administering a combination of PRRT and radiation therapy to a subject. An alternative form of therapy can comprise administering a combination of PRRT, immunotherapy and chemotherapy to a subject. An alternative form of therapy can comprise administering a combination of PRRT, immunotherapy, chemotherapy and radiation therapy to a subject. An alternative form of therapy can comprise administering a combination of immunotherapy and chemotherapy to a subject.

Immunotherapy can comprise administering checkpoint inhibitors. Checkpoint inhibitors can comprise antibodies. Checkpoint inhibitors include, but are not limited to, anti-CTLA4 antibodies, anti-PD-1 antibodies, anti-PD-L1 antibodies, anti-AZAR antibodies, anti-B7-H3 antibodies, anti-B7-H4 antibodies, anti-BTLA antibodies, anti-IDO antibodies, anti-KIR antibodies, anti-LAG3 antibodies, anti-TIM3 antibodies and anti-VISTA (V-domain Ig suppressor of T cell activation) antibodies.

Anti-CTLA4 antibodies can include, but are not limited to, ipilimumab, tremelimumab and AGEN-1884. Anti-PD-1 antibodies include, but are not limited to, pembrolizumab, nivolumab pidilizumab, cemiplimab, REGN2810, AMP-224, MEDI0680, PDR001 and CT-001. Anti-PD-L1 antibodies include, but are not limited to atezolizumab, avelumab and durvalumab. Anti-CD137 antibodies include, but are not limited to, urelumab. Anti-B7-H3 antibodies include, but are not limited to, MGA271. Anti-KIR antibodies include, but are not limited to, Lirilumab. Anti-LAG3 antibodies include, but are not limited to, BMS-986016.

The term "immunotherapy" can refer to activating immunotherapy or suppressing immunotherapy. As will be appreciated by those in the art, activating immunotherapy refers to the use of a therapeutic agent that induces, enhances, or promotes an immune response, including, e.g., a T cell response while suppressing immunotherapy refers to the use of a therapeutic agent that interferes with, suppresses, or inhibits an immune response, including, e.g., a T cell response. Activating immunotherapy may comprise the use of checkpoint inhibitors. Activating immunotherapy may comprise administering to a subject a therapeutic agent that activates a stimulatory checkpoint molecule. Stimulatory checkpoint molecules include, but are not limited to, CD27, CD28, CD40, CD122, CD137, OX40, GITR and ICOS. Therapeutic agents that activate a stimulatory checkpoint molecule include, but are not limited to, MEDI0562, TGN1412, CDX-1127, lipocalin.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. An antibody that binds to a target refers to an antibody that is capable of binding the target with sufficient affinity such that the antibody is useful as a diagnostic and/or therapeutic agent in targeting the target. In one embodiment, the extent of binding of an anti-target antibody to an unrelated, non-target protein is less than about 10% of the binding of the antibody to target as measured, e.g., by a radioimmunoassay (MA) or biacore assay. In certain embodiments, an antibody that binds to a target has a dissociation constant (Kd) of <1 µM, <100 nM, <10 nM, <1 nM, <0.1 nM, <0.01 nM, or <0.001 nM (e.g. $10^8$ M or less, e.g. from $10^8$ M to $10^{13}$ M, e.g., from $10^9$ M to $10^{13}$ M). In certain embodiments, an anti-target antibody binds to an epitope of a target that is conserved among different species.

A "blocking antibody" or an "antagonist antibody" is one that partially or fully blocks, inhibits, interferes, or neutralizes a normal biological activity of the antigen it binds. For example, an antagonist antibody may block signaling through an immune cell receptor (e.g., a T cell receptor) so as to restore a functional response by T cells (e.g., proliferation, cytokine production, target cell killing) from a dysfunctional state to antigen stimulation.

An "agonist antibody" or "activating antibody" is one that mimics, promotes, stimulates, or enhances a normal biological activity of the antigen it binds. Agonist antibodies can also enhance or initiate signaling by the antigen to which it binds. In some embodiments, agonist antibodies cause or activate signaling without the presence of the natural ligand. For example, an agonist antibody may increase memory T cell proliferation, increase cytokine production by memory T cells, inhibit regulatory T cell function, and/or inhibit regulatory T cell suppression of effector T cell function, such as effector T cell proliferation and/or cytokine production.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Administering chemotherapy to a subject can comprise administering a therapeutically effective dose of at least one chemotherapeutic agent. Chemotherapeutic agents include, but are not limited to, 13-cis-Retinoic Acid, 2-CdA, 2-Chlorodeoxyadenosine, 5-Azacitidine, 5-Fluorouracil, 5-FU, 6-Mercaptopurine, 6-MP, 6-TG, 6-Thioguanine, Abemaciclib, Abiraterone acetate, Abraxane, Accutane, Actinomycin-D, Adcetris, Ado-Trastuzumab Emtansine, Adriamycin, Adrucil, Afatinib, Afinitor, Agrylin, Ala-Cort, Aldesleukin, Alemtuzumab, Alecensa, Alectinib, Alimta, Alitretinoin, Alkaban-AQ, Alkeran, All-transretinoic Acid, Alpha Interferon, Altretamine, Alunbrig, Amethopterin, Amifostine, Aminoglutethimide, Anagrelide, Anandron, Anastrozole, Apalutamide, Arabinosylcytosine, Ara-C, Aranesp, Aredia, Arimidex, Aromasin, Arranon, Arsenic Trioxide, Arzerra, Asparaginase, Atezolizumab, Atra, Avastin, Avelumab, Axicabtagene Ciloleucel, Axitinib, Azacitidine, Bavencio, Bcg, Beleodaq, Belinostat, Bendamustine, Bendeka, Besponsa, Bevacizumab, Bexarotene, Bexxar, Bicalutamide, Bicnu, Blenoxane, Bleomycin, Blinatumomab, Blincyto, Bortezomib, Bosulif, Bosutinib, Brentuximab Vedotin, Brigatinib, Busulfan, Busulfex, C225, Cabazitaxel, Cabozantinib, Calcium Leucovorin, Campath, Camptosar, Camptothecin-11, Capecitabine, Caprelsa, Carac, Carboplatin, Carfilzomib, Carmustine, Carmustine Wafer, Casodex, CCI-779, Ccnu, Cddp, Ceenu, Ceritinib, Cerubidine, Cetuximab, Chlorambucil, Cisplatin, Citrovorum Factor, Cladribine, Clofarabine, Clolar, Cobimetinib, Cometriq, Cortisone, Cosmegen, Cotellic, Cpt-11, Crizotinib, Cyclophosphamide, Cyramza, Cytadren, Cytarabine, Cytarabine Liposomal, Cytosar-U, Cytoxan, Dabrafenib, Dacarbazine, Dacogen, Dactinomycin, Daratumumab, Darbepoetin Alfa, Darzalex, Dasatinib, Daunomycin, Daunorubicin, Daunorubicin Cytarabine (Liposomal), daunorubicin-hydrochloride, Daunorubicin Liposomal, DaunoXome, Decadron, Decitabine, Degarelix, Delta-Cortef, Deltasone, Denileukin Diftitox, Denosumab, DepoCyt, Dexamethasone, Dexamethasone Acetate, Dexamethasone Sodium Phosphate, Dexasone, Dexrazoxane, Dhad, Dic, Diodex, Docetaxel, Doxil, Doxorubicin, Doxorubicin Liposomal, Droxia, DTIC, Dtic-Dome, Duralone, Durvalumab, Eculizumab, Efudex, Ellence, Elotuzumab, Eloxatin, Elspar, Eltrombopag, Emcyt, Empliciti, Enasidenib, Enzalutamide, Epirubicin, Epoetin Alfa, Erbitux, Eribulin, Erivedge, Erleada, Erlotinib, *Erwinia* L-asparaginase, Estramustine, Ethyol, Etopophos, Etoposide, Etoposide Phosphate, Eulexin, Everolimus, Evista, Exemestane, Fareston, Farydak, Faslodex, Femara, Filgrastim, Firmagon, Floxuridine, Fludara, Fludarabine, Fluoroplex, Fluorouracil, Fluorouracil (cream), Fluoxymesterone, Flutamide, Folinic Acid, Folotyn, Fudr, Fulvestrant, G-Csf, Gazyva, Gefitinib, Gemcitabine, Gemtuzumab ozogamicin, Gemzar, Gilotrif, Gleevec, Gleostine, Gliadel Wafer, Gm-Csf, Goserelin, Granix, Granulocyte—Colony Stimulating Factor, Granulocyte Macrophage Colony Stimulating Factor, Halaven, Halotestin, Herceptin, Hexadrol, Hexalen, Hexamethylmelamine, Hmm, Hycamtin, Hydrea, Hydrocort Acetate, Hydrocortisone, Hydrocortisone Sodium Phosphate, Hydrocortisone Sodium Succinate, Hydrocortone Phosphate, Hydroxyurea, Ibrance, Ibritumomab, Ibritumomab Tiuxetan, Ibrutinib, Iclusig, Idamycin, Idarubicin, Idelalisib, Idhifa, Ifex, IFN-alpha, Ifosfamide, IL-11, IL-2, Imbruvica, Imatinib Mesylate, Imfinzi, Imidazole Carboxamide, Imlygic, Inlyta, Inotuzumab Ozogamicin, Interferon-Alfa, Interferon Alfa-2b (PEG Conjugate), Interleukin-2, Interleukin-11, Intron A (interferon alfa-2b), Ipilimumab, Iressa, Irinotecan, Irinotecan (Liposomal), Isotretinoin, Istodax, Ixabepilone, Ixazomib, Ixempra, Jakafi, Jevtana, Kadcyla, Keytruda, Kidrolase, Kisqali, Kymriah, Kyprolis, Lanacort, Lanreotide, Lapatinib, Lartruvo, L-Asparaginase, Lbrance, Lcr, Lenalidomide, Lenvatinib, Lenvima, Letrozole, Leucovorin, Leukeran, Leukine, Leuprolide, Leurocristine, Leustatin, Liposomal Ara-C, Liquid Pred, Lomustine, Lonsurf, L-PAM, L-Sarcolysin, Lupron, Lupron Depot, Lynparza, Marqibo, Matulane, Maxidex, Mechlorethamine, Mechlorethamine Hydrochloride, Medralone, Medrol, Megace, Megestrol, Megestrol Acetate, Mekinist, Mercaptopurine, Mesna, Mesnex, Methotrexate, Methotrexate Sodium, Methylprednisolone, Meticorten, Midostaurin, Mitomycin, Mitomycin-C, Mitoxantrone, M-Prednisol, MTC, MTX, Mustargen, Mustine, Mutamycin, Myleran, Mylocel, Mylotarg, Navelbine, Necitumumab, Nelarabine, Neosar, Neratinib, Nerlynx, Neulasta, Neumega, Neupogen, Nexavar, Nilandron, Nilotinib, Nilutamide, Ninlaro, Nipent, Niraparib, Nitrogen Mustard, Nivolumab, Nolvadex, Novantrone, Nplate, Obinutuzumab, Octreotide, Octreotide Acetate, Odomzo, Ofatumumab, Olaparib, Olaratumab, Omacetaxine, Oncospar, Oncovin, Onivyde, Ontak, Onxal, Opdivo, Oprelvekin, Oraped, Orasone, Osimertinib, Otrexup, Oxaliplatin, Paclitaxel, Paclitaxel Protein-bound, Palbociclib, Pamidronate, Panitumumab, Panobinostat, Panretin, Paraplatin, Pazopanib, Pediapred, Peg Interferon, Pegaspargase, Pegfilgrastim, Peg-Intron, PEG-L-asparaginase, Pembrolizumab, Pemetrexed, Pentostatin, Perjeta, Pertuzumab, Phenylalanine Mustard, Platinol, Platinol-AQ, Pomalidomide, Pomalyst, Ponatinib, Portrazza, Pralatrexate, Prednisolone, Prednisone, Prelone, Procarbazine, Procrit, Proleukin, Prolia, Prolifeprospan 20 with Carmustine Implant, Promacta, Provenge, Purinethol, Radium 223 Dichloride, Raloxifene, Ramucirumab, Rasuvo, Regorafenib, Revlimid, Rheumatrex, Ribociclib, Rituxan, Rituxan Hycela, Rituximab, Rituximab Hyalurodinase, Roferon-A (Interferon Alfa-2a), Romidepsin, Romiplostim, Rubex, Rubidomycin Hydrochloride, Rubraca, Rucaparib, Ruxolitinib, Rydapt, Sandostatin, Sandostatin LAR, Sargramostim, Siltuximab, Sipuleucel-T, Soliris, Solu-Cortef, Solu-Medrol, Somatuline, Sonidegib, Sorafenib, Sprycel, Sti-571, Stivarga, Streptozocin, SU11248, Sunitinib, Sutent, Sylvant, Synribo, Tafinlar, Tagrisso, Talimogene Laherparepvec, Tamoxifen, Tarceva, Targretin, Tasigna, Taxol, Taxotere, Tecentriq, Temodar, Temozolomide, Temsirolimus, Teniposide, Tespa, Thalidomide, Thalomid, TheraCys, Thioguanine, Thioguanine Tabloid, Thiophosphoamide, Thioplex, Thiotepa, Tice, Tisagenlecleucel, Toposar, Topotecan, Toremifene, Torisel, Tositumomab, Trabectedin, Trametinib, Trastuzumab, Treanda, Trelstar, Tretinoin, Trexall, Trifluridine/Tipiricil, Triptorelin pamoate, Trisenox, Tspa, T-VEC, Tykerb, Valrubicin, Valstar, Vandetanib, VCR, Vectibix, Velban, Velcade, Vemurafenib, Venclexta, Venetoclax, VePesid, Verzenio, Vesanoid, Viadur, Vidaza, Vinblastine, Vinblastine Sulfate, Vincasar Pfs, Vincristine, Vincristine Liposomal, Vinorelbine, Vinorelbine Tartrate, Vismodegib, Vlb, VM-26, Vorinostat, Votrient, VP-16, Vumon, Vyxeos, Xalkori Capsules, Xeloda, Xgeva, Xofigo, Xtandi, Yervoy, Yescarta, Yondelis, Zaltrap, Zanosar, Zarxio, Zejula, Zelboraf, Zevalin, Zinecard, Ziv-aflibercept, Zoladex, Zoledronic Acid, Zolinza, Zometa, Zydelig, Zykadia, Zytiga, or any combination thereof.

Table 1 details the biomarker/housekeeper sequence information. The amplicon positions identified for each biomarker are underlined.

TABLE 1

| Gene Name | RefSeq Accession | Sequence | SEQ ID NO: |
|---|---|---|---|
| ARAF1 | NM_001654.4 | CTTGACAGACGTGACCCTGACCCAATAAGGGTGGAAGGCTGAGTCC<br>CGCAGAGCCAATAACGAGAGTCCGAGAGGCGACGGAGGCGGACTCT<br>GTGAGGAAACAAGAAGAGAGGCCCAAGATGGAGACGGCGGCGGCTG<br>TAGCGGCGTGACAGGAGCCCCATGGCACCTGCCCAGCCCCACCTCA<br>GCCCATCTTGACAAAATCTAAGGCTCCATGGAGCCACCACGGGGCC<br>CCCCTGCCAATGGGGCCGAGCCATCCCGGGCAGTGGGCACCGTCAA<br>AGTATACCTGCCCAACAAGCAACGCACGGTGGTGACTGTCCGGGAT<br>GGCATGAGTGTCTACGACTCTCTAGACAAGGCCCTGAAGGTGCGGG<br>GTCTAAATCAGGACTGCTGTGTGGTCTACCGACTCATCAAGGGACG<br>AAAGACGGTCACTGCCTGGGACACAGCCATTGCTCCCCTGGATGGC<br>GAGGAGCTCATTGTCGAGGTCCTTGAAGATGTCCCGCTGACCATGC<br>ACAATTTTGTACGGAAGACCTTCTTCAGCCTGGCGTTCTGTGACTT<br>CTGCCTTAAGTTTCTGTTCCATGGCTTCCGTTGCCAAACCTGTGGC<br>TACAAGTTCCACCAGCATTGTTCCTCCAAGGTCCCCACAGTCTGTG<br>TTGACATGAGTACCAACCGCCAACAGTTCTACCACAGTGTCCAGGA<br>TTTGTCCGGAGGCTCCAGACAGCATGAGGCTCCCTCGAACCGCCCC<br>CTGAATGAGTTGCTAACCCCCCAGGGTCCCAGCCCCCGCACCCAGC<br>ACTGTGACCCGGAGCACTTCCCCTTCCCTGCCCCAGCCAATGCCCC<br>CCTACAGCGCATCCGCTCCACGTCCACTCCCAACGTCCATATGGTC<br>AGCACCACGGCCCCCATGGACTCCAACCTCATCCAGCTCACTGGCC<br>AGAGTTTCAGCACTGATGCTGCCGGTAGTAGAGGAGGTAGTGATGG<br>AACCCCCCGGGGGAGCCCCAGCCCAGCCAGCGTGTCCTCGGGGAGG<br>AAGTCCCCACATTCCAAGTCACCAGCAGAGCAGCGCGAGCGGAAGT<br>CCTTGGCCGATGACAAGAAGAAAGTGAAGAACCTGGGGTACCGGGA<br>CTCAGGCTATTACTGGGAGGTACCACCCAGTGAGGTGCAGCTGCTG<br>AAGAGGATCGGGACGGGCTCGTTTGGCACCGTGTTTCGAGGGCGGT<br>GGCATGGCGATGTGGCCGTGAAGGTGCTCAAGGTGTCCCAGCCCAC<br>AGCTGAGCAGGCCCAGGCTTTCAAGAATGAGATGCAGGTGCTCAGG<br>AAGACGCGACATGTCAACATCTTGCTGTTTATGGGCTTCATGACCC<br>GGCCGGGATTTGCCATCATCACACAGTGGTGTGAGGGCTCCAGCCT<br>CTACCATCACCTGCATGTGGCCGACACAC<u>GCTTCGACATGGTCCAG</u><br><u>CTCATCGACGTGGCCCGGCAGACTGCCCAGGGCATGGACTACCTCC</u><br><u>ATGCCAAGAACATCATCCACCGAGATCTCAAGTCTAACAACATCTT</u><br>CCTACATGAGGGGCTCACGGTGAAGATCGGTGACTTTGGCTTGGCC<br>ACAGTGAAGACTCGATGGAGCGGGCCCAGCCCTTGGAGCAGCCCT<br>CAGGATCTGTGCTGTGGATGGCAGCTGAGGTGATCCGTATGCAGGA<br>CCCGAACCCCTACAGCTTCCAGTCAGACGTCTATGCCTACGGGGTT<br>GTGCTCTACGAGCTTATGACTGGCTCACTGCCTTACAGCCACATTG<br>GCTGCCGTGACCAGATTATCTTTATGGTGGGCCGTGGCTATCTGTC<br>CCCGGACCTCAGCAAAATCTCCAGCAACTGCCCCAAGGCCATGCGG<br>CGCCTGCTGTCTGACTGCCTCAAGTTCCAGCGGGAGGAGCGGCCCC<br>TCTTCCCCCAGATCCTGGCCACAATTGAGCTGCTGCAACGGTCACT<br>CCCCAAGATTGAGCGGAGTGCCTCGGAACCCTCCTTGCACCGCACC<br>CAGGCCGATGAGTTGCCTGCCTGCCTACTCAGCGCAGCCCGCCTTG<br>TGCCTTAGGCCCCGCCCAAGCCACCAGGGAGCCAATCTCAGCCCTC<br>CACGCCAAGGAGCCTTGCCCACCAGCCAATCAATGTTCGTCTCTGC<br>CCTGATGCTGCCTCAGGATCCCCCATTCCCCACCCTGGGAGATGAG<br>GGGGTCCCCATGTGCTTTTCCAGTTCTTCTGGAATTGGGGGACCCC<br>CGCCAAAGACTGAGCCCCCTGTCTCCTCCATCATTTGGTTTCCTCT<br>TGGCTTTGGGGATACTTCTAAATTTTGGGAGCTCCTCCATCTCCAA<br>TGGCTGGGATTTGTGGCAGGGATTCCACTCAGAACCTCTCTGGAAT<br>TTGTGCCTGATGTGCCTTCCACTGGATTTTGGGGTTCCCAGCACCC | 1 |

TABLE 1-continued

| Gene Name | RefSeq Accession | Sequence | SEQ ID NO: |
|---|---|---|---|
| | | CATGTGGATTTTGGGGGGTCCCTTTTGTGTCTCCCCCGCCATTCAA<br>GGACTCCTCTCTTTCTTCACCAAGAAGCACAGAATTCTGCTGGGCC<br>TTTGCTTGTTTAAAAAAAAAAAAAAAAAAAAAAAAAAAAAAAAAA<br>AAAAAAAAAAAAAAAAAAAAAAAAAAAAAA | |
| BRAF | NM_004333.4 | CGCCTCCCTTCCCCCTCCCCGCCCGACAGCGGCCGCTCGGGCCCCG<br>GCTCTCGGTTATAAGATGGCGGCGCTGAGCGGTGGCGGTGGTGGCG<br>GCGCGGAGCCGGGCCAGGCTCTGTTCAACGGGGACATGGAGCCCGA<br>GGCCGGCGCCGGCGCCGGCGCCGCGGCCTCTTCGGCTGCGGACCCT<br>GCCATTCCGGAGGAGGTGTGGAATATCAAACAAATGATTAAGTTGA<br>CACAGGAACATATAGAGGCCCTATTGGACAAATTTGGTGGGAGCA<br>TAATCCACCATCAATATATCTGGAGGCCTATGAAGAATACACCAGC<br>AAGCTAGATGCACTCCAACAAAGAGAACAACAGTTATTGGAATCTC<br>TGGGGAACGGAACTGATTTTTCTGTTTTCTAGCTCTGCATCAATGGA<br>TACCGTTACATCTTCTTCCTCTTCTAGCCTTTCAGTGCTACCTTCA<br>TCTCTTTCAGTTTTTCAAAATCCCACAGATGTGGCACGGAGCAACC<br>CCAAGTCACCACAAAAACCTATCGTTAGAGTCTTCCTGCCCAACAA<br>ACAGAGGACAGTGGTACCTGCAAGGTGTGGAGTTACAGTCCGAGAC<br>AGTCTAAAGAAAGCACTGATGATGAGAGGTCTAATCCCAGAGTGCT<br>GTGCTGTTTACAGAATTCAGGATGGAGAGAAGAAACCAATTGGTTG<br>GGACACTGATATTTCCTGGCTTACTGGAGAAGAATTGCATGTGGAA<br>GTGTTGGAGAATGTTCCACTTACAACACACAACTTTGTACGAAAAA<br>CGTTTTTCACCTTAGCATTTTGTGACTTTTGTCGAAAGCTGCTTTT<br>CCAGGGTTTCCGCTGTCAAACATGTGGTTATAAATTTCACCAGCGT<br>TGTAGTACAGAAGTTCCACTGATGTGTGTTAATTATGACCAACTTG<br>ATTTGCTGTTTGTCTCCAAGTTCTTTGAACACCACCCAATACCACA<br>GGAAGAGGCGTCCTTAGCAGAGACTGCCCTAACATCTGGATCATCC<br>CCTTCCGCACCCGCCTCGGACTCTATTGGGCCCCAAATTCTCACCA<br>GTCCGTCTCCTTCAAAATCCATTCCAATTCCACAGCCCTTCCGACC<br>AGCAGATGAAGATCATCGAAATCAATTTGGGCAACGAGACCGATCC<br>TCATCAGCTCCCAATGTGCATATAAACACAATAGAACCTGTCAATA<br>TTGATGACTTGATTAGAGACCAAGGATTTCGTGGTGATGGAGGATC<br>AACCACAGGTTTGTCTGCTACCCCCCTGCCTCATTACCTGGCTCA<br>CTAACTAACGTGAAAGCCTTACAGAAATCTCCAGGACCTCAGCGAG<br>AAAGGAAGTCATCTTCATCCTCAGAAGACAGGAATCGAATGAAAAC<br>ACTTGGTAGACGGGACTCGAGTGATGATTGGGAGATTCCTGATGGG<br>CAGATTACAGTGGGACAAAGAATTGGATCTGGATCATTTGGAACAG<br>TCTACAAGGGAAAGTGGCATGGTGATGTGGCAGTGAAAATGTTGAA<br>TGTGACAGCACCTACACCTCAGCAGTTACAAGCCTTCAAAAATGAA<br>GTAGGAGTACTCAGGAAAACACGACATGTGAATATCCTACTCTTCA<br>TGGGCTATTCCACAAAGCCACAACTGGCTATTGTTACCCAGTGGTG<br>TGAGGGCTCCAGCTTGTATCACCATCTCCATATCATTGAGACCAAA<br>TTTGAGATGATCAAACTTATAGATATTGCACGACAGACTGCACAGG<br>GCATGGATTACTTACACGCCAAGTCAATCATCCACAGAGACCTCAA<br>GAGTAATAATATATTTCTTCATGAAGACCTCACAGTAAAAATAGGT<br>GATTTTGGTCTAGCTACAGTGAAATCTCGATGGAGTGGGTCCCATC<br>AGTTTGAACAGTTGTCTGGATCCATTTTGTGGATGGCACCAGAAGT<br>CATCAGAATGCAAGATAAAAATCCATACAGCTTTCAGTCAGATGTA<br>TATGCATTTGGAATTGTTCTGTATGAATTGATGACTGGACAGTTAC<br>CTTATTCAAACATCAACAACAGGGACCAGATAATTTTTATGGTGGG<br>ACGAGGATACCTGTCTCCAGATCTCAGTAAGGTACGGAGTAACTGT<br>CCAAAAGCCATGAAGAGATTAATGGCAGAGTGCCTCAAAAAGAAAA<br>GAGATGAGAGACCACTCTTTCCCCAAATTCTCGCCTCTATTGAGCT<br>GCTGGCCCGCTCATTGCCAAAAATTCACCGCAGTGCATCAGAACCC<br>TCCTTGAATCGGGCTGGTTTCCAAACAGAGGATTTTAGTCTATATG<br>CTTGTGCTTCTCCAAAAACACCCATCCAGGCAGGGGATATGGTGC<br>GTTTCCTGTCCACTGAAACAAATGAGTGAGAGTTCAGGAGAGTA<br>GCAACAAAAGGAAATAAATGAACATATGTTTGCTTATATGTTAAA<br>TTGAATAAAATACTCTCTTTTTTTTTAAGGTGAACCAAAGAACACT<br>TGTGTGGTTAAAGACTAGATATAATTTTTCCCCAAACTAAAATTTA<br>TACTTAACATTGGATTTTTAACATCCAAGGGTTAAAATACATAGAC<br>ATTGCTAAAAATTGGCAGAGCCTCTTCTAGAGGCTTTACTTTCTGT<br>TCCGGGTTTGTATCATTCACTTGGTTATTTTAAGTAGTAAACTTCA<br>GTTTCTCATGCAACTTTTGTTGCCAGCTATCACATGTCCACTAGGG<br>ACTCCAGAAGAAGACCCTACCTATGCCTGTGTTTGCAGGTGAGAAG<br>TTGGCAGTCGGTTAGCCTGGGTTAGATAAGGCAAACTGAACAGATC<br>TAATTTAGGAAGTCAGTAGAATTTAATAATTCTATTATTATTCTTA<br>ATAATTTTTCTATAACTATTTCTTTTTATAACAATTTGGAAAATGT<br>GGATGTCTTTTATTTCCTTGAAGCAATAAACTAAGTTTCTTTTTAT<br>AAAAA | 2 |
| KRAS | NM_004985.4 | TCCTAGGCGGCGGCCGCGGCGGCGGAGGCAGCAGCGGCGGCGGCAG<br>TGGCGGCGGCGAAGGTGGCGGCGGCTCGGCCAGTACTCCCGGCCCC<br>CGCCATTTCGGACTGGGAGCGAGCGCGGCGCAGGCACTGAAGGCGG<br>CGGCGGGGCCAGAGGCTCAGCGGCTCCCAGGTGCGGGAGAGAGGCC<br>TGCTGAAAATGACTGAATATAAACTTGTGGTAGTTGGAGCTGGTGG<br>CGTAGGCAAGAGTGCCTTGACGATACAGCTAATTCAGAATCATTTT | 3 |

TABLE 1-continued

| Gene Name | RefSeq Accession | Sequence | SEQ ID NO: |
|---|---|---|---|
| | | GTGGACGAATATGATCCAACAATAGAGGATTCCTACAGGAAGCAAG<br>TAGTAATTGATGGAGAAACCTGTCTCTTGGATATTCTCGACACAGC<br>AGGTCAAGAGGAGTACAGTGCAATGAGGGACCAGTACATGAGGACT<br>GGGGAGGGCTTTCTTTGTGTATTTGCCATAAATAATACTAAATCAT<br>TTGAAGATATTCACCATTATAGAGAACAAATTAAAAGAGTTAAGGA<br>CTCTGAAGATGTACCTATGGTCCTAGTAGGAAATAAATGTGATTTG<br>CCTTCTAGAACAGTAGAC<u>ACAAAACAGGCTCAGGACTTAGCAAGAA</u><br><u>GTTATGGAATTCCTTTTATTGAAACATCAGCAAAGACAAGACAGGG</u><br><u>TGTTGATGATGCCTTCTATACATTAGTTCGAGAAATTCGAAAACAT</u><br><u>AAA</u>GAAAAGATGAGCAAAGATGGTAAAAAGAAGAAAAAGAAGTCAA<br>AGACAAAGTGTGTAATTATGTAAATACAATTTGTACTTTTTTCTTA<br>AGGCATACTAGTACAAGTGGTAATTTTTGTACATTACACTAAATTA<br>TTAGCATTTGTTTTAGCATTACCTAATTTTTTCCTGCTCCATGCA<br>GACTGTTAGCTTTTACCTTAAATGCTTATTTTAAAATGACAGTGGA<br>AGTTTTTTTTTCCTCTAAGTGCCAGTATTCCCAGAGTTTTGGTTTT<br>TGAACTAGCAATGCCTGTGAAAAAGAAACTGAATACCTAAGATTTC<br>TGTCTTGGGGTTTTTGGTGCATGCAGTTGATTACTTCTTATTTTC<br>TTACCAATTGTGAATGTTGGTGTGAAACAAATTAATGAAGCTTTTG<br>AATCATCCCTATTCTGTGTTTTATCTAGTCACATAAATGGATTAAT<br>TACTAATTTCAGTTGAGACCTTCTAATTGGTTTTTACTGAAACATT<br>GAGGGAACACAAATTTATGGGCTTCCTGATGATGATTCTTCTAGGC<br>ATCATGTCCTATAGTTTGTCATCCCTGATGAATGTAAAGTTACACT<br>GTTCACAAAGGTTTTGTCTCCTTTCCACTGCTATTAGTCATGGTCA<br>CTCTCCCCAAAATATTATATTTTTCTATAAAAAGAAAAAAATGGA<br>AAAAAATTACAAGGCAATGGAAACTATTATAAGGCCATTTCCTTTT<br>CACATTAGATAAATTACTATAAAGACTCCTAATAGCTTTTCCTGTT<br>AAGGCAGACCCAGTATGAAATGGGGATTATTATAGCAACCATTTTG<br>GGGCTATATTTACATGCTACTAAATTTTTATAATAATTGAAAAGAT<br>TTTAACAAGTATAAAAAATTCTCATAGGAATTAAATGTAGTCTCCC<br>TGTGTCAGACTGCTCTTTCATAGTATAACTTTAAATCTTTTCTTCA<br>ACTTGAGTCTTTGAAGATAGTTTTAATTCTGCTTGTGACATTAAAA<br>GATTATTTGGGCCAGTTATAGCTTATTAGGTGTTGAAGAGACCAAG<br>GTTGCAAGGCCAGGCCCTGTGTGAACCTTTGAGCTTTCATAGAGAG<br>TTTCACAGCATGGACTGTGTCCCCACGGTCATCCAGTGTTGTCATG<br>CATTGGTTAGTCAAAATGGGGAGGGACTAGGGCAGTTTGGATAGCT<br>CAACAAGATACAATCTCACTCTGTGGTGGTCCTGCTGACAAATCAA<br>GAGCATTGCTTTTGTTTCTTAAGAAAACAAACTCTTTTTTAAAAAT<br>TACTTTTAAATATTAACTCAAAAGTTGAGATTTTGGGGTGGTGGTG<br>TGCCAAGACATTAATTTTTTTTTTAAACAATGAAGTGAAAAAGTTT<br>TACAATCTCTAGGTTTGGCTAGTTCTCTTAACACTGGTTAAATTAA<br>CATTGCATAAACACTTTTCAAGTCTGATCCATATTTAATAATGCTT<br>TAAAATAAAAATAAAAACAATCCTTTTGATAAATTTAAAATGTTAC<br>TTATTTTAAAATAAATGAAGTGAGATGGCATGGTGAGGTGAAAGTA<br>TCACTGGACTAGGAAGAAGGTGACTTAGGTTCTAGATAGGTGTCTT<br>TTAGGACTCTGATTTTGAGGACATCACTTACTATCCATTTCTTCAT<br>GTTAAAAGAAGTCATCTCAAACTCTTAGTTTTTTTTTTTACAACT<br>ATGTAATTTATATTCCATTTACATAAGGATACACTTATTTGTCAAG<br>CTCAGCACAATCTGTAAATTTTTAACCTATGTTACACCATCTTCAG<br>TGCCAGTCTTGGGCAAAATTGTGCAAGAGGTGAAGTTTATATTTGA<br>ATATCCATTCTCGTTTTAGGACTCTTCTTCCATATTAGTGTCATCT<br>TGCCTCCCTACCTTCCACATGCCCATGACTTGATGCAGTTTTAAT<br>ACTTGTAATTCCCCTAACCATAAGATTTACTGCTGCTGTGGATATC<br>TCCATGAAGTTTTCCCACTGAGTCACATCAGAAATGCCCTACATCT<br>TATTTCCTCAGGGCTCAAGAGAATCTGACAGATACCATAAAGGGAT<br>TTGACCTAATCACTAATTTTCAGGTGGTGGCTGATGCTTTGAACAT<br>CTCTTTGCTGCCCAATCCATTAGCGACAGTAGGATTTTTCAAACCT<br>GGTATGAATAGACAGAACCCTATCCAGTGGAAGGAGAATTTAATAA<br>AGATAGTGCTGAAAGAATTCCTTAGGTAATCTATAACTAGGACTAC<br>TCCTGGTAACAGTAATACATTCCATTGTTTTAGTAACCAGAAATCT<br>TCATGCAATGAAAAATACTTTAATTCATGAAGCTTACTTTTTTTTT<br>TTGGTGTCAGAGTCTCGCTCTTGTCACCCAGGCTGGAATGCAGTGG<br>CGCCATCTCAGCTCACTGCAACCTCCATCTCCCAGGTTCAAGCGAT<br>TCTCGTGCCTCGGCCTCCTGAGTAGCTGGGATTACAGGCGTGTGCC<br>ACTACACTCAACTAATTTTTGTATTTTTAGGAGAGACGGGGTTTCA<br>CCCTGTTGGCCAGGCTGGTCTCGAACTCCTGACCTCAAGTGATTCA<br>CCCACCTTGGCCTCATAAACCTGTTTTGCAGAACTCATTTATTCAG<br>CAAATATTTATTGAGTGCCTACCAGATGCCAGTCACCGCACAAGGC<br>ACTGGGTATATGGTATCCCAAACAAGAGACATAATCCCGGTCCTT<br>AGGTAGTGCTAGTGTGGTCTGTAATATCTTACTAAGGCCTTTGGTA<br>TACGACCCAGAGATAACACGATGCGTATTTAGTTTTGCAAAGAAG<br>GGGTTTGGTCTCTGTGCCAGCTCTATAATTGTTTTGCTACGATTCC<br>ACTGAAACTCTTCGATCAAGCTACTTTATGTAAATCACTTCATTGT<br>TTTAAAGGAATAAACTTGATTATATTGTTTTTTTATTTGGCATAAC<br>TGTGATTCTTTTAGGACAATTACTGTACACATTAAGGTGTATGTCA<br>GATATTCATATTGACCCAAATGTGTAATATTCCAGTTTTCTCTGCA<br>TAAGTAATTAAAAATATACTTAAAAATTAATAGTTTTATCTGGGTAC<br>AAATAAACAGGTGCCTGAACTAGTTCACAGACAAGGAAACTTCTAT | |

TABLE 1-continued

| Gene Name | RefSeq Accession | Sequence | SEQ ID NO: |
|---|---|---|---|
| | | GTAAAAATCACTATGATTTCTGAATTGCTATGTGAAACTACAGATC<br>TTTGGAACACTGTTTAGGTAGGGTGTTAAGACTTACACAGTACCTC<br>GTTTCTACACAGAGAAAGAAATGGCCATACTTCAGGAACTGCAGTG<br>CTTATGAGGGGATATTTAGGCCTCTTGAATTTTTGATGTAGATGGG<br>CATTTTTTTAAGGTAGTGGTTAATTACCTTTATGTGAACTTTGAAT<br>GGTTTAACAAAAGATTTGTTTTTGTAGAGATTTTAAAGGGGGAGAA<br>TTCTAGAAATAAATGTTACCTAATTATTACAGCCTTAAAGACAAAA<br>ATCCTTGTTGAAGTTTTTTTAAAAAAAGCTAAATTACATAGACTTA<br>GGCATTAACATGTTTGTGGAAGAATATAGCAGACGTATATTGTATC<br>ATTTGAGTGAATGTTCCCAAGTAGGCATTCTAGGCTCTATTTAACT<br>GAGTCACACTGCATAGGAATTTAGAACCTAACTTTTATAGGTTATC<br>AAAACTGTTGTCACCATTGCACAATTTTGTCCTAATATATACATAG<br>AAACTTTGTGGGGCATGTTAAGTTACAGTTTGCACAAGTTCATCTC<br>ATTTGTATTCCATTGATTTTTTTTTCTTCTAAACATTTTTTCTTC<br>AAACAGTATATAACTTTTTTTAGGGGATTTTTTTTAGACAGCAAA<br>AACTATCTGAAGATTTCCATTTGTCAAAAAGTAATGATTTCTTGAT<br>AATTGTGTAGTAATGTTTTTTAGAACCCAGCAGTTACCTTAAAGCT<br>GAATTTATATTTAGTAACTTCTGTGTTAATACTGGATAGCATGAAT<br>TCTGCATTGAGAAACTGAATAGCTGTCATAAAATGAAACTTTCTTT<br>CTAAAGAAAGATACTCACATGAGTTCTTGAAGAATAGTCATAACTA<br>GATTAAGATCTGTGTTTTAGTTTAATAGTTTGAAGTGCCTGTTTGG<br>GATAATGATAGGTAATTTAGATGAATTTAGGGGAAAAAAAAGTTAT<br>CTGCAGATATGTTGAGGGCCCATCTCTCCCCCCACACCCCCACAGA<br>GCTAACTGGGTTACAGTGTTTTATCCGAAAGTTTCCAATTCCACTG<br>TCTTGTGTTTTCATGTTGAAAATACTTTTGCATTTTTCCTTTGAGT<br>GCCAATTTCTTACTAGTACTATTTCTTAATGTAACATGTTTACCTG<br>GAATGTATTTTAACTATTTTTGTATAGTGTAAACTGAAACATGCAC<br>ATTTTGTACATTGTGCTTTCTTTTGTGGGACATATGCAGTGTGATC<br>CAGTTGTTTTCCATCATTTGGTTGCGCTGACCTAGGAATGTTGGTC<br>ATATCAAACATTAAAAATGACCACTCTTTTAATTGAAATTAACTTT<br>TAAATGTTTATAGGAGTATGTGCTGTGAAGTGATCTAAAATTTGTA<br>ATATTTTTGTCATGAACTGTACTACTCCTAATTATTGTAATGTAAT<br>AAAAAATAGTTACAGTGACTATGAGTGTGTATTTATTCATGAAATTT<br>GAACTGTTTGCCCCGAAATGGATATGAATACTTTATAAGCCATAG<br>ACACTATAGTATACCAGTGAATCTTTTATGCAGCTTGTTAGAAGTA<br>TCCTTTATTTCTAAAAGGTGCTGTGGATATTATGTAAAGGCGTGTT<br>TGCTTAAACTTAAAACCATATTTAGAAGTAGATGCAAAACAAATCT<br>GCCTTTATGACAAAAAAATAGGATAACATTATTTATTTATTTCCTT<br>TTATCAAAGAAGGTAATTGATACACAACAGGTGACTTGGTTTTAGG<br>CCCAAAGGTAGCAGCAGCAACATTAATAATGGAAATAATTGAATAG<br>TTAGTTATGTATGTTAATGCCAGTCACCAGCAGGCTATTTCAAGGT<br>CAGAAGTAATGACTCCATACATATTATTTATTTCTATAACTACATT<br>TAAATCATTACCAGG | |
| RAF-1 | NM_002880.3 | AGAATCGGAGAGCCGGTGGCGTCGCAGGTCGGGAGGACGAGCACCG<br>AGTCGAGGGCTCGCTCGTCTGGGCCGCCCGAGAGTCTTAATCGCGG<br>GCGCTTGGGCCGCCATCTTAGATGGCGGGAGTAAGAGGAAAACGAT<br>TGTGAGGCGGGAACGGCTTTCTGCTGCCTTTTTTGGGCCCCGAAAA<br>GGGTCAGCTGGCCGGGCTTTGGGGCGCGTGCCCTGAGGCGCGGAGC<br>GCGTTTGCTACGATGCGGGGCTGCTCGGGGCTCCGTCCCCTGGGC<br>TGGGGACGCGCCGAATGTGACCGCCTCCCGCTCCCTCACCCGCCGC<br>GGGGAGGAGGAGCGGGCGAGAAGCTGCCGCCGAACGACAGGACGTT<br>GGGGCGGCCTGGCTCCCTCAGGTTTAAGAATTGTTTAAGCTGCATC<br>AATGGAGCACATACAGGGAGCTTGGAAGACGATCAGCAATGGTTTT<br>GGATTCAAAGATGCCGTGTTTGATGGCTCCAGCTGCATCTCTCCTA<br>CAATAGTTCAGCAGTTTGGCTATCAGCGCCGGGCATCAGATGATGG<br>CAAACTCACAGATCCTTCTAAGACAAGCAACACTATCCGTGTTTTC<br>TTGCCGAACAAGCAAAGAACAGTGGTCAATGTGCGAAATGGAATGA<br>GCTTGCATGACTGCCTTATGAAAGCACTCAAGGTGAGGGGCCTGCA<br>ACCAGAGTGCTGTGCAGTGTTCAGACTTCTCCACGAACACAAAGGT<br>AAAAAAGCACGCTTAGATTGGAATACTGATGCTGCGTCTTTGATTG<br>GAGAAGAACTTCAAGTAGATTTCCTGGATCATGTTCCCCTCACAAC<br>ACACAACTTTGCTCGGAAGACGTTCCTGAAGCTTGCCTTCTGTGAC<br>ATCTGTCAGAAATTCCTGCTCAATGGATTTCGATGTCAGACTTGTG<br>GCTACAAATTTCATGAGCACTGTAGCACCAAAGTACCTACTATGTG<br>TGTGGACTGAGTAACATCAGACAACTCTTATTGTTTCCAAATTCC<br>ACTATTGGTGATAGTGGAGTCCCAGCACTACCTTCTTTGACTATGC<br>GTCGTATGCGAGAGTCTGTTTCCAGGATGCCTGTTAGTTCTCAGCA<br>CAGATATTCTACACCTCACGCCTTCACCTTTAACACCTCCAGTCCC<br>TCATCTGAAGGTTCCCTCTCCCAGAGGCAGAGGT<u>GACATCCACAC</u><br><u>CTAATGTCCACATGGTCAGCACCACCCTGCCTGTGGACAGCAGGAT</u><br><u>GATTGAGGATGCAATTCGAAGTCACAGCGAATCAGCCTCCACCTTCA</u><br>GCCCTGTCCAGTAGCCCCAACAATCTGAGCCCAACAGGCTGGTCAC<br>AGCCGAAAACCCCCGTGCCAGCACAAAGAGAGCGGGCACCAGTATC<br>TGGGACCCAGGAGAAAAACAAAATTAGGCCTCGTGGACAGAGAGAT<br>TCAAGCTATTATTGGGAAATAGAAGCCAGTGAAGTGATGCTGTCCA<br>CTCGGATTGGGTCAGGCTCTTTTGGAACTGTTTATAAGGGTAAATG | 4 |

TABLE 1-continued

| Gene Name | RefSeq Accession | Sequence | SEQ ID NO: |
|---|---|---|---|
| | | GCACGGAGATGTTGCAGTAAAGATCCTAAAGGTTGTCGACCCAACC<br>CCAGAGCAATTCCAGGCCTTCAGGAATGAGGTGGCTGTTCTGCGCA<br>AAACACGGCATGTGAACATTCTGCTTTTCATGGGGTACATGACAAA<br>GGACAACCTGGCAATTGTGACCCAGTGGTGCGAGGGCAGCAGCCTC<br>TACAAACACCTGCATGTCCAGGAGACCAAGTTTCAGATGTTCCAGC<br>TAATTGACATTGCCCGGCAGACGGCTCAGGGAATGGACTATTTGCA<br>TGCAAAGAACATCATCCATAGAGACATGAAATCCAACAATATATTT<br>CTCCATGAAGGCTTAACAGTGAAAATTGGAGATTTTGGTTTGGCAA<br>CAGTAAAGTCACGCTGGAGTGGTTCTCAGCAGGTTGAACAACCTAC<br>TGGCTCTGTCCTCTGGATGGCCCCAGAGGTGATCCGAATGCAGGAT<br>AACAACCCATTCAGTTTCCAGTCGGATGTCTACTCCTATGGCATCG<br>TATTGTATGAACTGATGACGGGGGAGCTTCCTTATTCTCACATCAA<br>CAACCGAGATCAGATCATCTTCATGGTGGGCCGAGGATATGCCTCC<br>CCAGATCTTAGTAAGCTATATAAGAACTGCCCCAAAGCAATGAAGA<br>GGCTGGTAGCTGACTGTGTGAAGAAAGTAAAGGAAGAGAGGCCTCT<br>TTTTCCCCAGATCCTGTCTTCCATTGAGCTGCTCCAACACTCTCTA<br>CCGAAGATCAACCGGAGCGCTTCCGAGCCATCCTTGCATCGGGCAG<br>CCCACACTGAGGATATCAATGCTTGCACGCTGACCACGTCCCCGAG<br>GCTGCCTGTCTTCTAGTTGACTTTGCACCTGTCTTCAGGCTGCCAG<br>GGGAGGAGGAGAAGCCAGCAGGCACCACTTTTCTGCTCCCTTTCTC<br>CAGAGGCAGAACACATGTTTTCAGAGAAGCTGCTGCTAAGGACCTT<br>CTAGACTGCTCACAGGGCCTTAACTTCATGTTGCCTTCTTTTCTAT<br>CCCCTTTGGGCCCTGGGAGAAGGAAGCCATTTGCAGTGCTGGTGTGT<br>CCTGCTCCCTCCCCACATTCCCCATGCTCAAGGCCCAGCCTTCTGT<br>AGATGCGCAAGTGGATGTTGATGGTAGTACAAAAAGCAGGGGCCCA<br>GCCCCAGCTGTTGGCTACATGAGTATTTAGAGGAAGTAAGGTAGCA<br>GGCAGTCCAGCCCTGATGTGGAGACACATGGGATTTTGGAAATCAG<br>CTTCTGGAGGAATGCATGTCACAGGCGGGACTTTCTTCAGAGAGTG<br>GTGCAGCGCCAGACATTTTGCACATAAGGCACCAAACAGCCCAGGA<br>CTGCCGAGACTCTGGCCGCCCGAAGGAGCCTGCTTTGGTACTATGG<br>AACTTTTCTTAGGGGACACGTCCTCCTTTCACAGCTTCTAAGGTGT<br>CCAGTGCATTGGGATGGTTTTCCAGGCAAGGCACTCGGCCAATCCG<br>CATCTCAGCCCTCTCAGGGAGCAGTCTTCCATCATGCTGAATTTTG<br>TCTTCCAGGAGCTGCCCCTATGGGGCGGGGCCGCAGGGCCAGCCTT<br>GTTTCTCTAACAAACAAACAAACAAACAGCCTTGTTTCTCTAGTCA<br>CATCATGTGTATACAAGGAAGCCAGGAATACAGGTTTTCTTGATGA<br>TTTGGGTTTTAATTTTGTTTTTATTGCACCTGACAAAATACAGTTA<br>TCTGATGGTCCCTCAATTATGTTATTTTAATAAAATAAATTAAATT<br>GTAAAAAAAAAAAAAAAAAAAA | |
| ATP6V1H | NM_015941.3 | AGCAGTCACGTGCCTCCGATCACGTGACCGGCGCCTCTGTCATTCT<br>ACTGCGGCCGCCCTGGCTTCCTTCTACCTGTGCGGCCCTCAACGTC<br>TCCTTGGTGCGGGACCCGCCTTCACTTTCGGCTCCCGGAGTCTCCCT<br>CCACTGCTCAGACCTCTGGACCTGACAGGAGACGCCTACTTGGCTC<br>TGACGCGGCGCCCCAGCCCGGCTGTGTCCCCGGCGCCCCGGACCAC<br>CCTCCCTGCCGGCTTTGGGTGCGTTGTGGGGTCCCGAGGATTCGCG<br>AGATTTGTTGAAAGACATTCAAGATTACGAAGTTTAGATGACCAAA<br>ATGGATATCCGAGGTGCTGTGGATGCTGCTGTCCCCACCAATATTA<br>TTGCTGCCAAGGCTGCAGAAGTTCGTGCAAACAAAGTCAACTGGCA<br>ATCCTATCTTCAGGGACAGATGATTTCTGCTGAAGATTGTGAGTTT<br>ATTCAGAGGTTTGAAATGAAACGAAGCCCTGAAGAGAAGCAAGAGA<br>TGCTTCAAACTGAAGGCAGCCAGTGTGCTAAAACATTTATAAATCT<br>GATGACTCATATCTGCAAAGAACAGACCGTTCAGTATATACTAACT<br>ATGGTGGATGATATGCTGCAGGAAAATCATCAGCGTGTTAGCATTT<br>TCTTTGACTATGCAAGATGTAGCAAGAACACTGCGTGGCCCTACTT<br>TCTGCCAATGTTGAATCGCCAGGATCCCTTCACTGTTCATATGGCA<br>GCAAGAATTATTGCCAAGTTAGCAGCTTGGGGAAAAGAACTGATGG<br>AAGGCAGTGACTTAAATTACTATTTCAATTGGATAAAAACTCAGCT<br>GAGTTCACAGAAACTGCGTGGTAGCGGTGTTGCTGTTGAAACAGGA<br>ACAGTCTCTTCAAGTGATAGTTCGCAGTATGTGCAGTGCGTGGCCG<br>GGTGTTTGCAGCTGATGCTCCGGGTCAATGAGTACCGCTTTGCTTG<br>GGTGGAAGCAGATGGGTAAATTGCATAATGGGAGTGTTGAGTAAC<br>AAGTGTGGCTTTCAGCTCCAGTATCAAATGATTTTTTCAATATGGC<br>TCCTGGCATTCAGTCCTCAAATGTGTGAACACCTGCGGCGCTATAA<br>TATCATTCCAGTTCTGTCTGATATCCTTCAGGAGTCTGTCAAAGAG<br>AAAGTAACAAGAATCATTCTTGCAGCATTTCGTAACTTTTTAGAAA<br>AATCAACTGAAAGAGAAACTCGCCAAGAATATGCCCTGGCTATGAT<br>TCAGTGCAAAGTTCTGAAACAGTTGGGAGAACTTGGAACAGCAGAAG<br>TACGATGATGAAGATATCAGCGAAGATATCAAATTTCTTTTGGAAA<br>AACTTGGAGAGAGTGTCCAGGACCTTAGTTCATTTGATGAATACAG<br>TTCAGAACTTAAATCTGGAAGGTTGGAATGGAGTCCTGTGCACAAA<br>TCTGAGAAATTTTGGAGAGAATGCTGTGAGGTTAAATGAGAGA<br>ATTATGAACTCTTGAAAATCTTGACAAAACTTTTGGAAGTGTCAGA<br>TGATCCCCAAGTCTTAGCTGTTGCTGCTCACGATGTTGGAGAATAT<br>GTGCGGCATTATCCACGAGGCAAACGGGTCATCGAGCAGCTCGGTG<br>GGAAGCAGCTGGTCATGAAC<u>CACATGCATCATGAAGACCAGCAGGT</u><br><u>CCGCTATAATGCTCTGCTGGCCGTGCAGAAGCTCATGGTGCACAAC</u> | 5 |

TABLE 1-continued

| Gene Name | RefSeq Accession | Sequence | SEQ ID NO: |
|---|---|---|---|
| | | TGGGAATACCTTGGCAAGCAGCTCCAGTCCGAGCAGCCCCAGACCG<br>CTGCCGCCCGAAGCTAAGCCTGCCTCTGGCCTTCCCCTCCGCCTCA<br>ATGCAGAACCAGTAGTGGGAGCACTGTGTTTAGAGTTAAGAGTGAA<br>CACTGTTTGATTTTACTTGGAATTTCCTCTGTTATATAGCTTTTCC<br>CAATGCTAATTTCCAAACAACAACAACAAAATAACATGTTTGCCTG<br>TTAAGTTGTATAAAAGTAGGTGATTCTGTATTTAAAGAAAATATTA<br>CTGTTACATATACTGCTTGCAATTTCTGTATTTATTGTTCTCTGGA<br>AATAAATATAGTTATTAAAGGATTCTCACTCCAAACATGGCCTCTC<br>TCTTTACTTGGACTTTGAACAAAAGTCAACTGTTGTCTCTTTTCAA<br>ACCAAATTGGGAGAATTGTTGCAAAGTAGTGAATGGCAAATAAATG<br>TTTTAAAATCTATCGCTCTATCAA | |
| OAZ2 | NM_002537.3 | ATGCAGATGAGGCACTCGGGGGCGGGGCGGCGGCGGCGGCGGC<br>GGTGGCGGCCGGGGAGGGTCAGTTGGAGGCAGGCGCTCGCTGAGGC<br>AAAAGGAGGCGCTCGGCCCGCGGCCTGACAGGGACTTAGCCCGCAG<br>AGATCGACCCCGCGCGCGTGACCCCACACCCACCCACTCATCCATC<br>TATCCACTCCCTGCGCCGCCTCCTCCCACCCTGAGCAGAGCCGCCG<br>AGGATGATAAACACCCAGGACAGTAGTATTTTGCCTTTGAGTAACT<br>GTCCCCAGCTCCAGTGCTGCAGGCACATTGTTCCAGGGCCTCTGTG<br>GTGCTCCTGATGCCCCTCACCCACTGTCGAAGATCCCCGGTGGGCG<br>AGGGGGCGGCAGGGATCCTTCTCTCTCAGCTCTAATATATAAGGAC<br>GAGAAGCTCACTGTGACCCAGGACCTCCCTGTGAATGATGGAAAAC<br>CTCACATCGTCCACTTCCAGTATGAGGTCACCGAGGTGAAGGTCTC<br>TTCTTGGGATGCAGTCCTGTCCAGCCAGAGCCTGTTTGTAGAAATC<br>CCAGATGGATTATTAGCTGATGGGAGCAAAGAAGGATTGTTAGCAC<br>TGCTAGAGTTTGCTGAAGAGAAGATGAAAGTGAACTATGTCTTCAT<br>CTGCTTCAGGAAGGGCCGAGAAGACAGAGCTCCACTCCTGAAGACC<br>TTCAGCTTCTTGGGCTTTGAGATTGTACGTCCAGGCCATCCCTGTG<br>TCCCCTCTCGGCCAGATGTGATGTTCATGGTTTATCCCCTGGACCA<br>GAACTTGTCCGATGAGGACTAATAGTCATAGAGGATGCTTTACCCA<br>AGAGCCACAGTGGGGGAAGAGGGGAAGTTAGGCAGCCCTGGGACAG<br>ACGAGAGGGCTCCTCGCTGTCTAGGGAAGGACACTGAGGGGCTCAG<br>GGTGAGGGTTGCCTATTGTGTTCTCGGAGTTGACTCGTTGAAATTG<br>TTTTCCATAAAGAACAGTATAAACATATTATTCACATGTAATCACC<br>AATAGTAAATGAAGATGTTTATGAACTGGCATTAGAAGCTTTCTAA<br>ACTGCGCTGTGTGATGTGTTCTATCTAGCCTAGGGGAGGACATTGC<br>CTAGAGGGGAGGGACTGTCTGGGTTCAGGGGCATGGCCTGGAGGG<br>CTGGTGGGCAGCACTGTCAGGCTCAGGTTTCCCTGCTGTTGGCTTT<br>CTGTTTTGGTTATTAAGACTTGTGTATTTTCTTTCTTTGCTTCCTG<br>TCACCCCAGGGGCTCCTGAGTATAGGCTTTTCAGTCCCTGGGCAGT<br>GTCCTTGAGTTGTTTTTTGACACTCTTACCTGGGCTTCTCTGTGTG<br>CATTTGCGTCTGGCCTGGAGTAAGCAGGTCCGACCCCTCCTTCTTT<br>ACAGCTTAGTGTTATTCTGGCATTTGTTAAGCTGGCTTAATCTGT<br>TTAATGTTATCAGTACATTTTAAATAGGGGCATTGAAATTTACTCC<br>CACCACCAGGGCTTTTTTGGGGGATGCCTGGGCCTTTAAAACACTA<br>GCCAAACTCTAATTAATTCTCAAATCACTGCCAGGAGTTCTTGCTC<br>CTGGCTGCAGGCCCAGGCCCCAAGGTCTCCTTCTTGGGGTCACAAA<br>CAGCAGTAAGGAAGAGGAATATATAGCAACTCAGGGCCTGGGAATT<br>GTGGGGCAATCCGTTCTTAGGGACTGGATACTTCGGCTGGCTGAG<br>TATAGTACTAGCTGCCTCCCCACCAGGTTCCGAGTAGTGTCTGAGA<br>CTCTGCTCTGCAGGGCCTAGGGTAGCGCTGGGAGTGTAGAAGTGGC<br>CTGCCCTTAACTGTTTTCACTAAACAGCTTTTTCTAAGGGGAGAGC<br>AAGGGGGAGAGATCTAGATTGGGTGAGGGGGACGGGGATGTCAGGG<br>AGGCAAGTGTGTTGTGTTACTGTGTCAATAAACTGATTTAAAGTTG<br>GAAAAAAAAAAAAA | 6 |
| PANK2 | NM_024960.4 | ATGCTGGGGGAGGGGCTGGCGGCCTCGACGGCAGCTGCGGAACTAG<br>GCCGAGGGACAAAGGCTAAGTTTTTCCATGGTTTGGACTGGATATC<br>GGTGGAACTCTGGTCAAGCTGGTATATTTTGAACCCAAAGACATCA<br>CTGCTGAAGAAGAAGAGGAAGAGTGGAAAGTCTTAAAAGCATTCG<br>GAAGTACCTGACCTCCAATGTGGCTTATGGGTCTACAGGCATTCGG<br>GACGTGCACCTCGAGCTGAAGGACCTGACTCTGTGTGGACGCAAAG<br>GCAATCTGCACTTTATACGCTTTCCCACTCATGACATGCCTGCTTT<br>TATTCAAATGGGCAGAGATAAAAACTTCTCGAGTCTCCACACTGTC<br>TTTTGTGCCACTGGAGGTGGAGCGTACAAATTTGAGCAGGATTTTC<br>TCACAATAGGTGATCTTCAGCTTTGCAAACTGGATGAACTAGATTG<br>CTTGATCAAAGGAATTTTATACATTGACTCAGTCGGATTCAATGGA<br>CGGTCACAGTGCTATTACTTTGAAAACCCTGCTGATTCTGAAAAGT<br>GTCAGAAGTTACCATTTGATTTGAAAAATCCGTATCCTCTGCTTCT<br>GGTGAACATTGGCTCAGGGGTTAGCATCTTAGCAGTATATTCCAAA<br>GATAATTACAAACGGGTCACAGGTACTAGTCTTGGAGGAGGAACTT<br>TTTTGGTCTCTGCTGTCTTCTTACTGGCTGTACCACTTTTGAAGA<br>AGCTCTTGAAATGGCATCTCGTGGAGATAGCACCAAAGTGGATAAA<br>CTAGTACGAGATATTTATGAGGGGACTATGAGAGGTTTGGACTGC<br>CAGGCTGGGCTGTGGCTTCAAGCTTTGGAAACATGATGAGCAAGGA<br>GAAGCGAGAGGCTGTCAGTAAAGAGGACCTGGCCAGAGCGACTTTG<br>ATCACCATCACCAACAACATTGGCTCAATAGCAAGAATGTGTGCCC | 7 |

TABLE 1-continued

| Gene Name | RefSeq Accession | Sequence | SEQ ID NO: |
|---|---|---|---|
| | | TTAATGAAAACATTAACCAGGTGGTATTTGTTGGAAATTTCTTGAG<br>AATTAATACGATCGCCATGCGGCTTTTGGCATATGCTTTGGATTAT<br>TGGTCCAAGGGGCAGTTGAAAGCACTTTTTTCGGAACACGAGGGTT<br>ATTTTGGAGCTGTTGGAGCACTCCTTGAGCTGTTGAAGATCCCGTG<br>ATCATTACCTGGGGAGGGGTTCCTGAAACCTTCCACAATGGGATCT<br>GTGGACTTTCATTTTTTTAAGAGACTTACTCAATTTCATGACTGTA<br>CTACCTGAAACAAAGTGAGAAAGGACAGGTGTATTTTTCTAAGTCA<br>TCAAGATAAATCCTTAAGAATTCAGTCTAAATTAGCAACCAGGAAG<br>GAAAAATATATTAAAAACAACAAAAAAGTGGCACATGTCCAGGCAG<br>TGTGAGGATTTGCTGTATATAAGTTGCCTGCTTTGTATTTTTGAAA<br>TCTCTGCATCACTCATTGGAAGTGCTTCTGAAGAGAGCTGCTCTGT<br>GTTCAGTTGACTGGTTTTGTGTCCTGTTTGAACTTGCTGAATGTAA<br>GGCAGGCTACTATGCGTTATAATCTAATCACAATTTGTCAATATGG<br>TCTTGGCAATCATCTGTGCATTACTCTGGTTTGCATTAAGCCTGTG<br>TGTGAACTTACTGTAAAACATGTTTTATTTCAAGGTTCTGCAAAAT<br>TAATTGGGCAGGTTAATTGTGTACCTGAAACTTAACAAGCAGTTTT<br>TGGAAGGGCA | |
| PLD36.3 | NM_00103169 | GCATCCTCTCACCGCCGGAAGCTGAACTGACTCGTCCGCGGCCGCT<br>CTACCCCAACAGGCCGCCACCAGCGAGAGTGCGGCCATAACCATCA<br>CGTGACCGCCCACCGACACCAGCGAGAGTGCAGTCGTAACCGTCAC<br>GTGACCGCCCACCGTCGGCCCGGCGCTCCCCTCCGCCCGAAGCTAG<br>CAAGCGGCGCGGCCAATGAGAAAGGCGCATGCCTGGCCCCCGCCGG<br>CCTGCAGTCTAGCCGTAGTGCGCCTGCGCGCGGCTAGGAGGGGCCG<br>TCAGGCGGGGATACAGCCTGGAAGGTAATGCATGTCCATGGTACAC<br>AAATTCACAAGTTTGGAGACCCTGACACACCCACCTTCTCACCTGG<br>GCTCTGCGTATCCCCCAGCCTTGAGGGAAGATGAAGCCTAAACTGA<br>TGTACCAGGAGCTGAAGGTGCCTGCAGAGGAGCCCGCCAATGAGCT<br>GCCCATGAATGAGATTGAGGCGTGGAAGGCTGCGGAAAAGAAAGCC<br>CGCTGGGTCCTGCTGGTCCTCATTCTGGCGGTTGTGGGCTTCGGAG<br>CCCTGATGACTCAGCTGTTTCTATGGGAATACGGCGACTTGCATCT<br>CTTTGGGCCCAACCAGCGCCCAGCCCCTGCTATGACCCTTGCGAA<br>GCAGTGCTGGTGGAAAGCATTCCTGAGGGCCTGGACTTCCCCAATG<br>CCTCCACGGGGAACCCTTCCACCAGCCAGGCCTGGCTGGGCCTGCT<br>CGCCGGTGCGCACAGCAGCCTGGACATCGCCTCCTTCTACTGG<u>ACC</u><br><u>CTCACCAACAATGACACCCACACGCAGGAGCCCTCTGCCCAGCAGG</u><br><u>GTGAGGAGGTCCTCCGGCAGCTGCAGACCCTGGCACCAAAGGGCGT</u><br><u>GAACGTCCG</u>CATCGCTGTGAGCAAGCCCAGCGGGCCCCAGCCACAG<br>GCGGACCTGCAGGCTCTGCTGCAGAGCGGTGCCCAGGTCCGCATGG<br>TGGACATGCAGAAGCTGACCCATGGCGTCCTGCATACCAAGTTCTG<br>GGTGGTGGACCAGACCCACTTCTACCTGGGCAGTGCCAACATGGAC<br>TGGCGTTCACTGACCCAGGTCAAGGAGCTGGGCGTGGTCATGTACA<br>ACTGCAGCTGCCTGGCTCGAGACCTGACCAAGATCTTTGAGGCCTA<br>CTGGTTCCTGGGCCAGGCAGGCAGCTCCATCCCATCAACTTGGCCC<br>CGGTTCTATGACACCCGCTACAACAAGAGACACCAATGGAGATCT<br>GCCTCAATGGAACCCCTGCTCTGGCCTACCTGGCGAGTGCGCCCCC<br>ACCCCTGTGTCCAAGTGGCCGCACTCCAGACCTGAAGGCTCTACTC<br>AACGTGGTGGACAATGCCCGGAGTTTCATCTACGTCGCTGTCATGA<br>ACTACCTGCCCACTCTGGAGTTCTCCCACCCTCACAGGTTCTGGCC<br>TGCCATTGACGATGGGCTGCGGCGGGCCACCTACGAGCGTGGCGTC<br>AAGGTGCGCCTGCTCATCAGCTGCTGGGGACACTCGGAGCCATCCA<br>TGCGGGCCTTCCTGCTCTCTCTGGCTGCCCTGCGTGACAACCATAC<br>CCACTCTGACATCCAGGTGAAACTCTTTGTGGTCCCCGCGGATGAG<br>GCCCAGGCTCGAATCCCATATGCCCGTGTCAACCACAACAAGTACA<br>TGGTGACTGAACGCGCCACCTACATCGGAACCTCCAACTGGTCTGG<br>CAACTACTTCACGGAGACGGCGGGCACCTCGCTGCTGGTGACGCAG<br>AATGGGAGGGGCGGCCTGCGGAGCCAGCTGGAGGCCATTTTCCTGA<br>GGGACTGGGACTCCCCTTACAGCCATGACCTTGACACCTCAGCTGA<br>CAGCGTGGGCAACGCCTGCCGCCTGCTCTGAGGCCCGATCCAGTGG<br>GCAGGCCAAGGCCTGCTGGGCCCCCGCGGACCCAGGTGCTCTGGGT<br>CACGGTCCCTGTCCCCGCGCCCCCGCTTCGTCTGCCCCATTGTGG<br>CTCCTCAGGCTCTCTCCCCTGCTCTCCCACCTCTACCTCCACCCCC<br>ACCGGCCTGACGCTGTGGCCCCGGGACCCAGCAGAGCTGGGGGAGG<br>GATCAGCCCCCAAAGAAATGGGGGTGCATGCTGGGCCTGGCCCCCT<br>GGCCCACCCCCACTTTCCAGGGCAAAAAGGGCCCAGGGTTATAATA<br>AGTAAATAACTTGTCTGTACAGCCTGAAAAAAAAAAAAAAAAAAA | 8 |
| ALG9 | NM_024740.2 | GTCTTTTGTCCCTCGGCGGACACCGTTTGCCAGCCAAAGCTATGTC<br>TGCGCGCTCACCGACTTCATAGGGTGCCGAATTCTTTTTTCCCCAG<br>GCTTGCCATGGCTAGTCGAGGGGCTCGGCAGCGCCTGAAGGGCAGC<br>GGGGCCAGCAGTGGGGATACGGCCCCGGCTGCGGACAAGCTGCGGG<br>AGCTGCTGGGCAGCCGAGAGGCGGGCGGCGGAGCACCGGACCGA<br>GTTATCTGGGAACAAAGCAGGACAAGTCTGGGCACCTGAAGGATCT<br>ACTGCTTTCAAGTGTCTGCTTTCAGCAAGGTTATGTGCTGCTCTCC<br>TGAGCAACATCTCTGACTGTGATGAAACATTCAACTACTGGGAGCC<br>AACACACTACCTCATCTATGGGGAAGGGTTTCAGACTTGGGAATAT<br>TCCCCAGCATATGCCATTCGCTCCTATGCTTACCTGTTGCTTCATG | 9 |

TABLE 1-continued

| Gene Name | RefSeq Accession | Sequence | SEQ ID NO: |
|---|---|---|---|
| | | CCTGGCCAGCTGCATTTCATGCAAGAATTCTACAAACTAATAAGAT<br>TCTTGTGTTTTACTTTTTGCGATGTCTTCTGGCTTTTGTGAGCTGT<br>ATTTGTGAACTTTACTTTTACAAGGCTGTGTGCAAGAAGTTTGGGT<br>TGCACGTGAGTCGAATGATGCTAGCCTTCTTGGTTCTCAGCACTGG<br>CATGTTTTGCTCATCATCAGCATTCCTTCCTAGTAGCTTCTGTATG<br>TACACTACGTTGATAGCCATGACTGGATGGTATATGGACAAGACTT<br>CCATTGCTGTGCTGGGAGTAGCAGCTGGGGCTATCTTAGGCTGGCC<br>ATTCAGTGCAGCTCTTGGTTTACCCATTGCCTTTGATTTGCTGGTC<br>ATGAAACACAGGTGGAAGAGTTTCTTTCATTGGTCGCTGATGGCCC<br>TCATACTATTTCTGGTGCCTGTGGTGGTCATTGACAGCTACTATTA<br>TGGGAAGTTGGTGATTGCACCACTCAACATTGTTTTGTATAATGTC<br>TTTACTCCTCATGGACCTGATCTTTATGGTACAGAACCCTGGTATT<br>TCTATTTAATTAATGGATTTCTGAATTTCAATGTAGCCTTTGCTTT<br>GGCTCTCCTAGTCCTACCACTGACTTCTCTTATGGAATACCTGCTG<br>CAGAGATTTCATGTTCAGAATTTAGGCCACCCGTATTGGCTTACCT<br>TGGCTCCAATGTATATTTGGTTTATAATTTTCTTCATCCAGCCTCA<br>CAAAGAGGAGAGATTTCTTTTCCCTGTGTATCCACTTATATGTCTC<br>TGTGGCGCTGTGGCTCTCTCTGCACTTCAGCACAGTTTTCTGTACT<br>TCCAGAAATGTTACCACTTTGTGTTTCAACGATATCGCCTGGAGCA<br>CTATACTGTGACATCGAATTGGCTGGCATTAGGAACTGTCTTCCTG<br>TTTGGGCTCTTGTCATTTTCTCGCTCTGTGGCACTGTTCAGAGGAT<br>ATCACGGGCCCCTTGATTTGTATCCAGAATTTTACCGAATTGCTAC<br>AGACCCAACCATCCACACTGTCCCAGAAGGCAGACCTGTGAATGTC<br>TGTGTGGGAAAAGAGTGGTATCGATTTCCCAGCAGCTTCCTTCTTC<br>CTGACAATTGGCAGCTTCAGTTCATTCCATCAGAGTTCAGAGGTCA<br>GTTACCAAAACCTTTTGCAGAAGGACCTCTGGCCACCCGGATTGTT<br>CCTACTGACATGAATGACCAGAATCTAGAAGAGCCATCCAGATATA<br>TTGATATCAGTAAATGCCATTATTTAGTGGATTTGGACACCATGAG<br>AGAAACACCCCGGGAGCCAAAATATTCATCCAATAAAGAAGAATGG<br>ATCAGCTTGGCCTATAGACCATTCCTTGATGCTTCTAGATCTTCAA<br>AGCTGCTGCGGGCATTCTATGTCCCCTTCCTGTCAGATCAGTATAC<br>AGTGTACGTAAACTACACCATCCTCAAACCCCGGAAAGCAAAGCAA<br>ATCAGGAAGAAAAGTGGAGGTTAGCAACACACCTGTGGCCCCAAAG<br>GACAACCATCTTGTTAACTATTGATTCCAGTGACCTGACTCCCTGC<br>AAGTCATCGCCTGTAACATTTGTAATAAAGGTCTTCTGACATGAAT<br>ACTGGAATCTGGGTGCTCTGGGCTAGTCAAAGTCTATTTCAAAGTC<br>TAATCAAAGTCACATTTGCTCCCTGTGTGTGTCTCTGTTCTGCATG<br>TAAACTTTTTGCAGCTAGGCAGAGAAAGGCCCTAAAGCACAGATAG<br>ATATATTGCTCCACATCTCATTGTTTTTCCTCTGTTCAATTATTTA<br>CTAGACCGGAGAAGAGCAGAACCAACTTACAGGAAGAATTGAAAAT<br>CCTGGTACTGGATGGCTGTGATAAGCTGTTCTCCACACTCTGGCCT<br>GGCATCTGAGAACTAGCAAGCCTCTCTTAGGCCATATGGGCTTCTC<br>CACCCAAAGCTGTTTGGCAGCTCCTAGCAGACCTTCTTATTGAAATC<br>CTCATGCTGAAAATGAACACAGCCTAGTTGCCAACCCACATGTCCT<br>TTTCACCTCCAGCAAGACTAAGCTTCTTTAAAGCACTTCACAGGAC<br>TAGGACCCTGTCCTGGAGCTATCTCAGGAAAAAGGTGACCATTTGA<br>GGAACTGTGACCTAATTTTATTATAATGATGCCTCTAATTTTCATT<br>TCCTTTACAACCAACTGTAACTATAAGGTTGTATTGCTTTTTTGTT<br>CAGTTTTAGCATGCTATTTTTTGAATTCTAGACTCCTCCATGTGAA<br>GATATCAACAGACAAAACTACAACTGTATAGGACATATTTGGAGAA<br>AATTCTATCAATTGATACATTTGGATGACATCACATTTTTAAGTAA<br>TGTAATCTGAGGCCATTGCTGAGGAAATTAAGAATTTTCCTTTTTT<br>TTTAACCACCCCCAGTGAAAAGGATCAGTGTATATTTATAGCACCT<br>ATTTTTTAGTTCTGTCTGTTGTGAGGCACATCCTGCATGGGCACT<br>TCTAGTCAAATAGGCAATGATAAGGACCTAATTAAAATGTGATAAG<br>TGTATACTATTACTTTAAAAGCCTTTACAGTCAGTACTTCAGTTTA<br>CAAGGCACTTTCACAGCATCTCGTTTGATCCTCACAGTCACAACAT<br>GTGGTAGACAAGGCAGGTGATTTTTATCCCCATTTTACAGATAAGG<br>AAACAGGCTGCGGGTGGGAGTGAGGGGAGGTAAAGATAGTTAGTT<br>GCCTAAGGTCACACAGCCAGTAAGTAATAGAGCTGGGACTGGAACC<br>CAGGTTTCCTTACTCTCATCTATTGCTCCTCCATATTCCTCACTCA<br>ACCATGAAAACATTACTTGAAAGGACTGATGAGGTTAACCAGAGAC<br>CTAACTGATATTGTAACTTTCTATTTTAAGGAAGAATTGTGTCTGT<br>ATTTGAGTTCTTTGGAGCCTCCAGTCTGCCTGTGTGTTAGACCAGC<br>ACAGCAGTGCTGTGTGATGCAGCCTGACCTGTGGCAGGAAAGTAGT<br>GCTTCTGTTTGGAAGTCATGTTCTTTTGCAGCCACACAGGATCCAA<br>ATATCAGTACTATTCCTGTAGTCAATCGGGGTCACATTATAGGTG<br>CCTTATTTCCCTAAGGGTAACTGATCTGAATATCTGCAAATAGGAT<br>GAATCTATTTTCAGAAGTTCCATCTTTCATTTTTCTTTTTTTTT<br>TGAGACAGAGTCTCATTCTGTCGCCCATGCTGGAGTGCAGTGGCGC<br>GATCTCGGCTCGCTGCAACCTCTGCCTCCCAGGTTGAAGCAATTCT<br>CATGCCTCAGCCACCCGAGTAGCTGGGATTACAGGCGTGCGCCATC<br>ATGCCCAGCTAATTTATGTATTTTTAGTAGAGTTGGAGTTTCACCA<br>TGTTGGCCAGGCTGGTCTTGGACTCCTGACCTCAGGTCATCCACCC<br>GCCTCAGCCTCCCAAAGTGCTGGTATTACAGGCGTGAGCCACCGCA<br>CCCAGCCCCATCTTTCATTTTCAAAGAGAAGGGCATTCTAATAGGA<br>ACTGGTGCCAAGAGAGAAGAAAAGAAGTGATAACAGAAGAAATGGC | |

TABLE 1-continued

| Gene Name | RefSeq Accession | Sequence | SEQ ID NO: |
|---|---|---|---|
| | | TAGTTACAATATTAAAAAGCTCCTCTTTGAGATCTCCTCTGCAGGA<br>ATATCAGAGACGGAGTTGAAGCGCTGGAGAGGTAATAGGTCTAGAC<br>AGTACAGAACAATAACTGGGGAGTGTGTGAGGATAGACTGGGCTCC<br>CCCTTGCTTGAAAGATCTCTGGCATTTAATTCTCAATTCTTGATTA<br>CTATTTTCCAGTGTAAAACTAGCACATATGATCTGACTACAGGACA<br>GAGAATTTTAAGTGAAACATTTGCCTTACTTGCAGTAATAATGTGC<br>TGTTCTTCACAGTAGCTAAGGCCCTCTATGTTTCCCAGAGGTAAAT<br>AAGAATCCAGGAATGGAGGTCCATCTGTGATGAATGGCTTTTTTCT<br>AATCAAAGTAGTATAATGCTGTTTTATCTGTTTTGTCATCTTGTTT<br>TTTTTTTTTTTAAAAAAACAAAACCTTAATTATAATATAGCGCAA<br>AGAAAGGCCAGGACTGATGCAGGGATTCCTTGGAAATATCAGTTCC<br>TATCACTTTTAAAACCTGATTTTGGATCTCTCTGTTCTATGTATGT<br>CTTTAGTGAGAGCACAATACATGGCAGAACGCTGTGCCAAATGTTA<br>TAGGTAAGGAATATAGAAATGAATGTTTTTTGTTGTGAAGGTGTTT<br>TCATGTGATATTTTATAAACACATTTTAAAAAATCTCCATCACTTT<br>TTAGTATAGGAAGGATAGCTTTGCCTGGGAAAAACAGTTTCAACAC<br>ACCTGCTCAGAGTAGCAGTTCTCCCTCAAAAAAGCAGTGTTCAGCC<br>TGCACTGACTGTTCTGCTTGCCAAAAGGAGGAAGCATGCAAGATAC<br>TTATTTCTCCATAGATTGTGGAGTATAGAGGGATGTGGGACTACAG<br>ATTATTATTTTTTTCCCCGAGACAGAGTCTTGCTCTGTCGCCCAG<br>GTTGGAACACAATGGCACGACCTCAGCTCACTGCAACCTCTGTCTC<br>CCGGGTTCAAGCAATTCTCCTGCTTCAGCCTCCTGAGTAGCTGGGA<br>TTACAGGCACACACCACCACCGCACTCAGCTAATTTTTGTATTTTT<br>AGTAGAGGTGGGGTTTTACCATGTTGGCCAGGCTGGTCTTAAACTC<br>CTGACCTTGTAATCATCCCGCCTCGGCCTCCTAAAGTGCTAGGATT<br>ACAGGCATGAGCCACCGCACCCGGCCCAGATAATTTTTAATAGCCT<br>TTGATCATGGGGTGAGTGAGGGAGTAGGTATACTTGGCAAATGCAT<br>GGTTCTCTGATTTCTAGCTCTAAAGCAGCCTTATCTGAATCCCCAA<br>ATCTTGTGATGCTGAGTACCATTACTGAACCAGTCTGCACGGTAGG<br>CATCTGCTACCAAAATTTACCTCCTACCTGGTAGGTGTCATCTGAT<br>AAGAAAGAAGACAGGTTATTTTAATTTTTTGAGATAATCACAGAAA<br>ATTGCAGCCCATACTCTTTATTACCGAATTCAAGTTTGGAAATAGA<br>CCCTTTGTTTTAAATCATGATGGGTCTTTATCCCAATCATTTATCT<br>GGGTCATTTTTCCAACTTTGGAGTTCTAGGAAAGAACCTTGAAAAC<br>CTGATATGATTCTGCAGCATGAGGTCTACGGTGACCATTTGGGCAA<br>AGCTCCAGTGGCAATCATTTATTGTGTTTTGCATTTCCTGGGATTT<br>ATTGAAATAAGAATTCACTGTGATTATGTAGTCTTCTGGCTAGTAT<br>CAGGCAGCTCTGCTTTTAATTTGGTTAATTTTATTTTCTCTGAAGA<br>GGGAGAAGAGGTACAATTTAATCTTGGCCTCCACAAGCATATTAAA<br>GCTCACGTGTTAATCAGTGCATTCTTATGCTCCTACATTAAATGCC<br>TTGGGTAAATGGATAAATGGACATGTGCCCAGCTTTAATTTTTTTT<br>GCAACAGAAAGATCAGACTTCCGTATGGCATCGTTGGATTTCAGAG<br>GCTTTCTGGTGTATCTGTAAATCTGAATGTTGCCTTCTGCCAGTCT<br>GTATAACCAGGTGATTCATGCTGCAAATGAAATCAGGAAGCAGTAA<br>AGTGTTAAAGCAAGAGTATTGTCCAATTCACTTGTCTTCCTGATCC<br>TTGTACTTTATTTCACGTGTCGGTGTTTACATTACATACTTATATT<br>TCCTGTGAAAGAAAGAGTTAAATAAATTGTAGCAGTTTGA | |
| NAP1L | NM_139207.2 | AAAAGATATGGTGGGGTGCTTAACAGAGGAGGTTAGACACCGGCGG<br>GAACCAGAGGAGCCCAAGCGCGGCGCCTGGGCCTCGGGGCTGCAGG<br>AGTCCTCGGTGGGGGTATGGAGGTCGCCGGGGAAGGAGGACGGTTC<br>AGTTGCTAGGCAACCCGGCCTGGACCCGCCTCTCGCTCGCGTTGCT<br>GGGAGACTACAAGGCCGGGAGGAGGGCGGCGAAAGGGCCCTACGTG<br>CTGACGCTAATTGTATATGAGCGCGAGCGGCGGGCTCTTGGGTCTT<br>TTTTAGCGCCATCTGCTCGCGGCGCCGCCTCCTGCTCCTCCCGCTG<br>CTGCTGCCGCTGCCGCCCTGAGTCACTGCCTGCGCAGCTCCGGCCG<br>CCTGGCTCCCCATACTAGTCGCCGATATTTGGAGTTCTTACAACAT<br>GGCAGACATTGACAACAAAGAACAGTCTGAACTTGATCAAGATTTG<br>GATGATGTTGAAGAAGTAGAAGAAGAGGGAAACTGGTGAAGAAACAA<br>AACTCAAAGCACGTCAGCTAACTGTTCAGATGATGCAAAATCCTCA<br>GATTCTTGCAGCCCTTCAAGAAAGACTTGATGGTCTGGTAGAAACA<br>CCAACAGGATACATTGAAAGCCTGCCTAGGGTAGTTAAAAGACGAG<br>TGAATGCTCTCAAAAACCTGCAAGTTAAATGTGCACAGATAGAAGC<br>CAAATTCTATGAGGAAGTTCACGATCTTGAAAGGAAGTATGCTGTT<br>CTCTATATCAGCCTCTATTTGATAAGCGATTTGAAATTATTAATGCAA<br>TTTATGAACCTACGGAAGAAGAATGTGAATGGAAACCAGATGAAGA<br>AGATGAGATTCGGAGGAATTGAAAGAAAAGGCCAAGATTGAAGAT<br>GAGAAAAAAGATGAAGAAAAAGAAGACCCCAAAGGAATTCCTGAAT<br>TTTGGTTAACTGTTTTTAAGAATGTTGACTTGCTCAGTGATATGGT<br>TCAGGAACACGATGAACCTATTCTGAAGCACTTGAAAGATATTAAA<br>GTGAAGTTCTCAGATGCTGGCCAGCCTATGAGTTTTGTCTTAGAAT<br>TTCACTTTGAACCCAATGAATATTTTACAAATGAAGTGCTGACAAA<br>GACATACAGGATGAGGTCAGAACCAGATGATTCTGATCCCTTTTCT<br>TTTGATGGACCAGAAATTATGGGTTGTACAGGGTGCCAGATAGATT<br>GGAAAAAAGGAAAGAATGTCACTTTGAAAACTATTAAGAAGAAGCA<br>GAAACACAAGGGACGTGGGACAGTTCGTACTGTGACTAAAACAGTT<br>TCCAATGACTCTTTCTTTAACTTTTTTTGCCCCTCCTGAAGTTCCTG | 10 |

TABLE 1-continued

| Gene Name | RefSeq Accession | Sequence | SEQ ID NO: |
|---|---|---|---|
| | | AGAGTGGAGATCTGGATGATGATGCTGAAGCTATCCTTGCTGCAGA<br>CTTCGAAATTGGTCACTTTTTACGTGAGCGTATAATCCCAAGATCA<br>GTGTTATATTTTACTGGAGAAGCTATTGAAGATGATGATGATGATT<br>ATGATGAAGAAGGTGAAGAAGCGGATGAGGAAGGGGAAGAAGAAGG<br>AGATGAGGAAAATGATCCAGACTATGACCCAAAGAAGGATCAAAAC<br>CCAGCAGAGTGCAAGCAGCAGTGAAGCAGGATGTATGTGGCCTTGA<br>GGATAACCTGCACTGGTCTACCTTCTGCTTCCCTGGAAAGGATGAA<br>TTTACATCATTTGACAAGCCTATTTTCAAGTTATTTGTTGTTTGTT<br>TGCTTGTTTTTGTTTTTGCAGCTAAAATAAAAATTTCAAATACAAT<br>TTTAGTTCTTACAAGATAATGTCTTAATTTTGTACCAATTCAGGTA<br>GAAGTAGAGGCCTACCTTGAATTAAGGGTTATACTCAGTTTTTAAC<br>ACATTGTTGAAGAAAAGGTACCAGCTTTGGAACGAGATGCTATACT<br>AATAAGCAAGTGTAAAAAAAAAAAAAAAGAGGAAGAAAATCTTAA<br>GTGATTGATGCTGTTTTCTTTTAAAAAAAAAAAAAAAATTCATTT<br>TCTTTGGGTTAGAGCTAGAGAGAAGGCCCCAAGCTTCTATGGTTTC<br>TTCTAATTCTTATTGCTTAAAGTATGAGTATGTCACTTACCCGTGC<br>TTCTGTTTACTGTGTAATTAAAATGGGTAGTACTGTTTACCTAACT<br>ACCTCATGGATGTGTTAAGGCATATTGAGTTAAATCTCATATAATG<br>TTTCTCAATCTTGTTAAAAGCTCAAAATTTTGGGCCTATTTGTAAT<br>GCCAGTGTGACACTAAGCATTTTGTTCACACCACGCTTTGATAACT<br>AAACTGGAAAACAAAGGTGTTAAGTACCTCTGTTCTGGATCTGGGC<br>AGTCAGCACTCTTTTTAGATCTTTGTGTGGCTCCTATTTTTATAGA<br>AGTGGAGGGATGCACTATTTCACAAGGTCCAAGATTTGTTTTCAGA<br>TATTTTTGATGACTGTATTGTAAATACTACAGGGATAGCACTATAG<br>TATTGTAGTCATGAGACTTAAAGTGGAAATAAGACTATTTTTGACA<br>AAAGATGCCATTAAATTTCAGACTGTAGAGCCACATTTACAATACC<br>TCAGGCTAATTACTGTTAATTTTGGGGTTGAACTTTTTTTTGACAG<br>TGAGGGTGGATTATTGGATTGTCATTAGAGGAAGGTCTAGATTTCC<br>TGCTCTTAATAAAATTACATTGAATTGATTTTTAGAGGTAATGAAA<br>ACTTCCTTTCTGAGAAGTTAGTGTTAAGGTCTTGGAATGTGAACAC<br>ATTGTTTGTAGTGCTATCCATTCCTCTCCTGAGATTTTAACTTACT<br>ACTGGAAATCCTTAACCAATTATAATAGCTTTTTTTCTTTATTTTC<br>AAAATGATTTCCTTTGCTTTGATTAGACACTATGTGCTTTTTTTTT<br>TTAACCATAGTTCATCGAAATGCAGCTTTTTCTGAACTTCAAAGAT<br>AGAATCCCATTTTTAATGAACTGAAGTAGCAAAATCATCTTTTTCA<br>TTCTTTAGGAAATAGCTATTGCCAAAGTGAAGGTGTAGATAATACC<br>TAGTCTTGTTACATAAAGGGGATGTGGTTTGCAGAAGAATTTTCTT<br>TATAAAATTGAAGTTTTAAGGGACGTCAGTGTTTATGCCATTTTTC<br>CAGTTCCAAAATGATTCCATTCCATTCTAGAAATTTGAAGTATGTA<br>ACCTGAAATCCTTAATAAAATTTGGATTTAATTTTATAAAATGTAC<br>TGGTGATATTTTGGGTGTTTTTTTTAAATGAATGTATATACTTTT<br>TTTTTGAAGAGTGGAGAGTAGTGATGTCTAGAGGGAGCTATTTTGT<br>GCTGAGGCCACTATGTTCTGTAAATATATAATTTTAAGAGCAACCT<br>CACAATCCCTGCTAAGTGGAGTTTATTATTTGAAGACTAAAATGGA<br>ATTCCATAGTTCCTGATAGGTTATATTCTGGGTTATTATTCTGAGT<br>TATCTACAAACATTTTTGAGATTTGTCTTTACACTCTGATTGTAGT<br>TTCCAGCAGCCCATGCACACTGCCAAGTAAGTCTCATTTTTTCCTG<br>TTAGAAATGGTGAAATATCATATAATCACTTATAAAGAAAACTGAT<br>ATGAAAAAATTTTAGAGTTGTTTGCTTTATGGTCACTCAAGTAGGG<br>TAAGTGTTCCACAAATTCCACAAGTTGATAGTTTAACATGGATGTC<br>TGAAAAGCCACATATATAATTTCTTAGGATTCTTAAATTAGTAAATC<br>TAGCTTACTGAAGCAGTATTAGCATCACTATTTTAGATTGCAAAAA<br>TACCTTAATTGTGTGGAACTGGCTTGTAGAGTGGTACTTAAGAAAA<br>ATGGGATTCTACCTCTATTTCTGTTTTAGCACACTTAATCAGGAAA<br>GGATATATTAACTTTCATAAAAATATTTTTGTTGTGTGAATAGGTT<br>AATGATATGGTAAGGCCCCTAAAATAACTGAATTAATTGTTTATTG<br>TAATTGTAGGCCATTCCCATTATTAAAAATAAAGACAAAACTTGAA<br>GTAACTGAAAATCTTATCGTGCTATGTAGAAATATTGAACTAATAT<br>TCAAATATTTGAATGCTTTGGTTTCAGGGATTGGTTTAAAATTGGA<br>GTCCTTTTTATGGGTTAGTCTTACAAAAATTTAAGCCTTTATATT<br>TTTGACTTTAAATCAAAACAAATGTTATTTAAATGTACAGAATAG<br>ATTGGTAGTGCAGAAGAGTGTAAGTTCTTCATAGGAGCTTTAGAAA<br>AGAGAAATATGTGCTAATTCAGTTTTTTTTAATCTGCACTGTACA<br>TATATACTTGGTAATTATGAGCTTGATTTTGTTTTTGGAAAATATGT<br>GTTCATAATTTAGGTAATTTGCTACTTAAAGCACTAAGTCTCTGAT<br>ACCTGAAAAGTACATGTAAATGGTGATGGTGAAATAATACTGCAGT<br>TAACTTAATAGATGTATACTGGTGATTTTGTATGCTGGATTAAAA<br>CTCCAGATATTAAAATATAACCTGGATAAAAAGCC | |
| NOL3 | NM_001185057 | GGCATTCAGAGAGTAGATGCCAGTCCTGGGAAAGGCAGGGGAGGAG<br>AGGAGAGCCACGGCTGACGCTTGGGGACAGAAGGAGGAGCCTGAGG<br>AGGAGACAGGACAGAGCGTCTGGAGAGGCAGGAGGACACCGAGTTC<br>CCCGTGTTGGCCTCCAGGTCCTGTGCTTGCGGAGCCGTCCGGCGGC<br>TGGGATCGAGCCCCGACAATGGGCAACGCGCAGGAGCGGCCGTCAG<br>AGACTATCGACCGCGAGCGGAAACGCCTGGTCGAGACGCTGCAGGC<br>GGACTCGGGACTGCTGTTGGACGCGCTGCTGGCGCGGGGCGTGCTC<br>ACCGGGCCAGAGTACGAGGCATTGGATGCACTGCCTGATGCCGAGC | 11 |

TABLE 1-continued

| Gene Name | RefSeq Accession | Sequence | SEQ ID NO: |
|---|---|---|---|
| | | GCAGGGTGCGCCGCCTACTGCTGCTGGTGCAGGGCAAGGGCGAGGC CGCCTGCCAGGAGCTGCTACGCTGTGCCCAGCGTACCGCGGGCGCG CCCGGACCCCGCTTGGGACTGGCAGCACGCTACCGGGACCGCAGCTA TGACCCTCCATGCCCAGGCCACTGGACGCCGGAGGCACCCGGCTCG GGGACCACATGCCCCGGGTTGCCCAGAGCTTCAGACCCTGACGAGG CCGGGGGCCCTGAGGGCTCCGAGGCGGTGCAATCCGGGACCCCGGA GGAGCCAGAGCCAGAGCTGGAAGCTGAGGCCTCTAAAGAGGCTGAA CCGGAGCCGGAGCCAGAGCCAGAGCTGGAACCCGAGGCTGAAGCAG AACCAGAGCCGGAACTGGAGCCAGAACCGGACCCAGAGCCCGAGCC CGACTTCGAGGAAAGGGACGAGTCCGAAGATTCCTGAAGGCCAGAG CTCTGACAGGCGGTGCCCCGCCCATGCTGGATAGGACCTGGGATGC TGCTGGAGCTGAATCGGATGCCACCAAGGCTCGGTCCAGCCCAGTA CCGCTGGAAGTGAATAAACTCCGGAGGGTCGGACGGGACCTGGGCT CTCTCCACGATTCTGGCTGTTTGCCCAGGAACTTAGGGTGGGTACC TCTGAGTCCCAGGGACCTGGGCAGGCCCAAGCCCACCACGAGCATC ATCCAGTCCTCAGCCCTAATCTGCCCTTAGGAGTCCAGGCTGCACC CTGGAGATCCCAAACCTAGCCCCCTAGTGGGACAAGGACCTGACCC TCCTGCCCGCATACACAACCCATTTCCCCTGGTGAGCCACTTGGCA GCATATGTAGGTACCAGCTCAACCCCACGCAAGTTCCTGAGCTGAA CATGGAGCAAGGGGAGGGTGACTTCTCTCCACATAGGGAGGGCTTA GAGCTCACAGCCTTGGGAAGTGAGACTAGAAGAGGGGAGCAGAAAG GGACCTTGAGTAGACAAAGGCCACACACATCATTGTCATTACTGTT TTAATTGTCTGGCTTCTCTCTGGACTGGGAGCTCAGTGAGGATTCT GACCAGTGACTTACACAAAAGGCGCTCTATACATATTATAATATAT TCGCTTACTAAATGAATAAGGACTTTCCAAAAAAAAAAAAAAAAA AAAAAAAAAAAA | |
| TECPR2 | NM_001172631 | CCCCCGGCGGAGCCAGCTGCTGCTCTTCGGTGCTGGCCCCGGTGCC GGCCCCGTTGCCCAGGGAACAGGCTCCCGGCAGCCCCGCGGCCCG GAGTCCATCCCGCCTCCTCCGGCCCGGCGGGGCCGACGAGTCCGGA GGGGCTGCCGCGGGAGCCCCCAGGTTTCCCTAGATGACAAATAAAC ATTCCTTTTCCTGCGTGAAGATAGTCTGTGGAAACCTTGGCCATGG CATCGATATCAGAGCCTGTTACATTCAGAGAGTTCTGCCCGTTGTA CTATCTCCTCAATGCCATTCCGACAAAGATCCAGAAGGGTTTCCGC TCTATCGTGGTCTATCTCACGCCCTCGACACCAACGGGGACTACA TCGCGGTGGGCAGCAGCATCGGCATGCTCTATCTGTACTGCCGGCA CCTCAACCAGATGAGGAAGTACAACTTTGAGGGGAAGACGGAATCT ATCACTGTGGTGAAGCTGCTGAGCTGCTTTGATGACCTGGTGGCAG CAGGCACAGCCTCTGGCAGGGTTGCAGTTTTTCAACTTGTATCTTC ATTGCCAGGGAGAAATAAACAGCTTCGGAGATTTGATGTCACTGGT ATTCACAAAAATAGCATTACAGCTCTGGCTTGGAGCCCCAATGGAA TGAAATTGTTCTCTGGAGATGACAAAGGCAAAATTGTTTATTCTTC TCTGGATCTAGACCAGGGGCTCTGTAACTCCCAGCTGGTGTTGGAG GAGCCATCTTCCATTGTGCAGCTGGATTATAGCCAGAAAGTGCTGC TGGTCTCTACTCTGCAAAGAAGTCTGCTCTTTTACACTGAAGAAAA GTCTGTAAGGCAAATTGGAACACAACCAAGGAAAAGTACTGGGAAA TTTGGTGCTTGTTTTATACCAGGACTCTGTAAGCAAAGTGATCTAA CCTTGTATGCGTCACGGCCCGGGCTCCGGCTATGGAAGGCTGATGT CCACGGGACTGTTCAAGCCACGTTTATCTTAAAAGATGCTTTTGCC GGGGGAGTCAAGCCTTTTGAACTGCACCCGCGTCTGGAATCCCCCA ACAGTGGAAGTTGCAGCTTACCTGAGAGGCACCTGGGGCTTGTTTC ATGTTTCTTTCAAGAAGGCTGGGTGCTGAGTTGGAATGAATATAGT ATCTATCTCCTAGACACAGTCAACCAGGCCACAGTTGCTGGTTTGG AAGGATCCGGTGATATTGTGTCTGTTTCGTGCACAGAAAATGAAAT ATTTTTCTTGAAAGGAGATAGGAACATTATAAGAATTTCAAGCAGG CCTGAAGGATTAACATCAACAGTGAGAGATGGTCTGGAGATGTCTG GATGCTCAGAGCGTGTCCACGTGCAGCAAGCGGAGAAGCTGCCAGG GGCCACAGTTTCTGAGACGAGGCTCAGAGGCTCTTCCATGGCCAGC TCCGTGGCCAGCGAGCCAAGGAGCAGGAGCAGCTCGCTCAACTCCA CCGACAGCGGCTCCGGGCTCCTGCCCCCTGGGCTCCAGGCCACCCC TGAGCTGGGCAAGGGCAGCCAGCCCCTGTCACAGAGATTCAACGCC ATCAGCTCAGAGGACTTTGACCAGGAGCTTGTCGTGAAGCCTATCA AAGTGAAAGGAAGAAGAAGAAGAAGAAGACAGAAGGTGGAAGCAG GAGCACCTGTCACAGCTCCCTGGAATCGACACCCTGCTCCGAATTT CCTGGGGACAGTCCCCAGTCCTTGAACACAGACTTGCTGTCGATGA CCTCAAGTGTCCTGGGCAGTAGCGTGGATCAGTTAAGTGCAGAGTC TCCAGACCAGGAAAGCAGCTTCAATGGTGAAGTGAACGGTGTCCCA CAGGAAAATACTGACCCCGAAACGTTTAATGTCCTGGAGGTGTCAG GATCAATGCCTGATTCTCTGGCTGAGGAAGATGACATTAGAACTGA AATGCCACACTGTCACCATGCACATGGGCGGGAGCTGCTCAATGGA GCGAGGGAAGATGTGGGAGGCAGTGATGTCACGGGACTCGGAGATG AGCCGTGTCCTGCAGATGATGGACCAAATAGCACACAGTTACCCTT CCAAGAACAGGACAGCTCTCCTGGGGCGCATGATGGGGAAGACATC CAACCCATTGGCCCCCAAAGCACTTTTTGTGAAGTCCCCCTCCTGA ACTCACTCACTGTGCCTTCCAGCCTCAGCTGGGCCCCAAGTGCTGA ACAGTGGCTGCCTGGGACCAGAGCTGATGAAGGCAGCCCCGTGGAG CCCAGCCAAGAGCAGGACATCCTAACCAGCATGGAGGCCTCTGGCC | 12 |

TABLE 1-continued

| Gene Name | RefSeq Accession | Sequence | SEQ ID NO: |
|---|---|---|---|
| | | ACCTCAGCACAAATCTCTGGCATGCTGTCACTGATGATGACACAGG<br>TCAGAAAGAAATACCCATTTCTGAACGTGTCTTGGGGAGTGTGGGA<br>GGACAGCTGACTCCGGTCTCTGCCTTGGCAGCCAGCACTCACAAGC<br>CCTGGCTTGAGCAGCCTCCACGGGATCAGACATTGACGTCCAGCGA<br>TGAGGAGGACATCTATGCCCACGGGCTTCCTTCTTCATCCTCAGAG<br>ACGAGTGTGACAGAGCTCGGACCTAGTTGCTCCCAGCAGGACCTGA<br>GCCGGCTGGGTGCAGAGGACGCCGGGCTGCTCAAGCCAGATCAGTT<br>TGCAGAAAGCTGGATGGGCTACTCGGGTCCCGGCTATGGCATCCTC<br>AGCTTGGTGGTCTCCGAGAAGTATATCTGGTGCCTGGACTACAAAG<br>GCGGCCTGTTCTGCAGCGCGTTGCCGGGCGCCGGGCTGCGCTGGCA<br>GAAGTTTGAAGATGCTGTCCAGCAGGTGGCAGTCTCGCCCTCAGGA<br>GCCCTTCTCTGGAAGATTGAACAGAAATCTAACCGGGCTTTTGCTT<br>GTGGGAAAGTCACCATCAAGGGGAAGCGGCACTGGTACGAAGCCCT<br>GCCCCAGGCAGTGTTTGTGGCCCTGAGCGATGACACGGCCTGGATC<br>ATCAGGACCAGTGGGGACCTATACTTGCAGACAGGTCTGAGCGTGG<br>ATCGCCCTTGTGCCAGAGCCGTAAAGGTGGACTGTCCCTACCCGCT<br>GTCCCAGATCACAGCCCGGAACAATGTGGTGTGGGCGCTGACAGAG<br>CAGAGGGCCCTCCTGTACCGGGAGGGCGTGAGCAGCTTCTGTCCGG<br>AAGGCGAGCAGTGGAAGTGTGACATTGTCAGCGAAAGGCAAGCTTT<br>AGAACCCGTCTGCATAACGCTCGGGGATCAGCAGACTCTCTGGGCC<br>CTGGACATCCATGGGAACCTGTGGTTCAGAACTGGCATTATTTCCA<br>AGAAGCCCCAAGGAGATGACGACCATTGGTGGCAAGTGAGCATCAC<br>GGACTATGTGGTGTTTGACCAGTGCAGCTTATTTCAGACGATAATC<br>CATGCCACTCACTCGGTGGCCACAGCAGCCCAAGCCCCCGTAGAAA<br>AGGTGGCAGATAAGCTGCGCATGGCGTTTTGGTCCCAGCAGCTTCA<br>GTGCCAGCCAAGCCTTCTCGGGGTCAATAACAGCGGTGTCTGGATC<br>TCCTCGGGCAAGAATGAATTCCACGTCGCTAAGGGAAGTCTCATAG<br>GCACCTACTGGAATCATGTGGTTCCCCGTGGGACAGCTTCTGCTAC<br>AAAATGGGCCTTTGTGTTGGCTTCTGCAGCTCCCACGAAGGAAGGA<br>AGCTTCCTGTGGCTGTGCCAGAGCAGCAAGGACCTGTGCAGCGTCA<br>GCGCCCAGAGCGCACAGTCGCGGCCCTCCACGGTGCAGCTGCCTCC<br>CGAAGCCGAGATGCGCGCCTATGCCGCCTGCCAGGATGCGCTGTGG<br>GCGCTGGACAGCCTCGGCCAGGTGTTCATCAGGACGCTCTCCAAGA<br>GCTGCCCCACGGGCATGCACTGGACCAGGCTGGACCTCTCCCAGCT<br>AGGAGCTGTAAAATTGACAAGCTTGGCATGTGGAAATCAGCACATC<br>TGGGCCTGTGATTCCAGGGGTGGAGTTTACTTCCGTGTAGGGACTC<br>AGCCTCTCAATCCCAGTCTCATGCTTCCAGCCTGGATAATGATTGA<br>GCCACCTGTCCAGGTAAGCAGAAGTTAGCTGGTGGAACTCACTCTT<br>CAGTAAGACAGAAACTGTGAGGATGCTGGTACTGGGAAAAAGGATC<br>TGCACAGCCTCTAGAGGCCTCCCAGCAAATGCGGGGAGCCATGCCC<br>CCAGGGTCTACACACTCTCGTTCATCAACATCACAACTGGAATTCG<br>GGATTTGTGAAGTTTAGAGCTGAACAGACTGTTACAGATTATGAGT<br>CAACACGTATATTTTCTCTTTCAAAATAATAATATTTCGTTTTTGA<br>CTTTTTACTAAGTGAATATTATTTTTTAAATCTGCCTATATATTGG<br>AACCTCTATTTTATAATAATAATGATAATAAATCAGTACCCAGAAG<br>TATAAAGAAGGTAAAAGTTACTTTGAAAAAAAAAAAAAAAAAAAA<br>AAAAAAAAAA | |

Definitions

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

As used herein, the terms "polynucleotide" and "nucleic acid molecule" are used interchangeably to mean a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence that serves as a probe in a microarray analysis preferably comprises a chain of nucleotides, more preferably DNA and/or RNA. In other embodiments, a nucleic acid molecule or nucleic acid sequence comprises other kinds of nucleic acid structures such a for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the terms "hybridize," "hybridizing", "hybridizes," and the like, used in the context of polynucleotides, are meant to refer to conventional hybridization conditions, such as hybridization in 50% formamide/6×SSC/0.1% SDS/100 μg/ml ssDNA, in which temperatures for hybridization are above 37 degrees and temperatures for washing in 0.1×SSC/0.1% SDS are above 55 degrees C., and preferably to stringent hybridization conditions.

As used herein, the term "normalization" or "normalizer" refers to the expression of a differential value in terms of a standard value to adjust for effects which arise from technical variation due to sample handling, sample preparation, and measurement methods rather than biological variation of biomarker concentration in a sample. For example, when measuring the expression of a differentially expressed protein, the absolute value for the expression of the protein can be expressed in terms of an absolute value for the expression of a standard protein that is substantially constant in expression.

The terms "diagnosis" and "diagnostics" also encompass the terms "prognosis" and "prognostics", respectively, as well as the applications of such procedures over two or more time points to monitor the diagnosis and/or prognosis over time, and statistical modeling based thereupon. Furthermore, the term diagnosis includes: a. prediction (determining if a patient will likely develop aggressive disease (hyperproliferative/invasive)), b. prognosis (predicting whether a patient will likely have a better or worse outcome at a pre-selected time in the future), c. therapy selection, d. therapeutic drug monitoring, and e. relapse monitoring.

The term "providing" as used herein with regard to a biological sample refers to directly or indirectly obtaining the biological sample from a subject. For example, "providing" may refer to the act of directly obtaining the biological sample from a subject (e.g., by a blood draw, tissue biopsy, lavage and the like). Likewise, "providing" may refer to the act of indirectly obtaining the biological sample. For example, providing may refer to the act of a laboratory receiving the sample from the party that directly obtained the sample, or to the act of obtaining the sample from an archive.

"Accuracy" refers to the degree of conformity of a measured or calculated quantity (a test reported value) to its actual (or true) value. Clinical accuracy relates to the proportion of true outcomes (true positives (TP) or true negatives (TN) versus misclassified outcomes (false positives (FP) or false negatives (FN)), and may be stated as a sensitivity, specificity, positive predictive values (PPV) or negative predictive values (NPV), or as a likelihood, odds ratio, among other measures.

The term "biological sample" as used herein refers to any sample of biological origin potentially containing one or more biomarkers. Examples of biological samples include tissue, organs, or bodily fluids such as whole blood, plasma, serum, tissue, lavage or any other specimen used for detection of disease.

The term "subject" as used herein refers to a mammal, preferably a human. The terms "subject" and "patient" are used interchangeably herein.

"Treating" or "treatment" as used herein with regard to a condition may refer to preventing the condition, slowing the onset or rate of development of the condition, reducing the risk of developing the condition, preventing or delaying the development of symptoms associated with the condition, reducing or ending symptoms associated with the condition, generating a complete or partial regression of the condition, or some combination thereof.

Biomarker levels may change due to treatment of the disease. The changes in biomarker levels may be measured by the present disclosure. Changes in biomarker levels may be used to monitor the progression of disease or therapy.

The term "stable disease" refers to a diagnosis for the presence of a NET, however the NET has been treated and remains in a stable condition, i.e. one that that is not progressive, as determined by imaging data and/or best clinical judgment.

The term "progressive disease" refers to a diagnosis for the presence of a highly active state of a NET, i.e. one has not been treated and is not stable or has been treated and has not responded to therapy, or has been treated and active disease remains, as determined by imaging data and/or best clinical judgment.

The terms "effective amount" and "therapeutically effective amount" of an agent or compound are used in the broadest sense to refer to a nontoxic but sufficient amount of an active agent or compound to provide the desired effect or benefit.

The term "benefit" is used in the broadest sense and refers to any desirable effect and specifically includes clinical benefit as defined herein. Clinical benefit can be measured by assessing various endpoints, e.g., inhibition, to some extent, of disease progression, including slowing down and complete arrest; reduction in the number of disease episodes and/or symptoms; reduction in lesion size; inhibition (i.e., reduction, slowing down or complete stopping) of disease cell infiltration into adjacent peripheral organs and/or tissues; inhibition (i.e. reduction, slowing down or complete stopping) of disease spread; decrease of auto-immune response, which may, but does not have to, result in the regression or ablation of the disease lesion; relief, to some extent, of one or more symptoms associated with the disorder; increase in the length of disease-free presentation following treatment, e.g., progression-free survival; increased overall survival; higher response rate; and/or decreased mortality at a given point of time following treatment.

The terms "cancer" and "cancerous" refer to or describe the physiological condition in mammals that is typically characterized by unregulated cell growth. Included in this definition are benign and malignant cancers. Examples of cancer include but are not limited to, carcinoma, lymphoma, blastoma, sarcoma, and leukemia. More particular examples of such cancers include adrenocortical carcinoma, bladder urothelial carcinoma, breast invasive carcinoma, cervical squamous cell carcinoma, endocervical adenocarcinoma, cholangiocarcinoma, colon adenocarcinoma, lymphoid neoplasm diffuse large B-cell lymphoma, esophageal carcinoma, glioblastoma multiforme, head and neck squamous cell carcinoma, kidney chromophobe, kidney renal clear cell carcinoma, kidney renal papillary cell carcinoma, acute myeloid leukemia, brain lower grade glioma, liver hepatocellular carcinoma, lung adenocarcinoma, lung squamous cell carcinoma, mesothelioma, ovarian serous cystadenocarcinoma, pancreatic adenocarcinoma, pheochromocytoma, paraganglioma, prostate adenocarcinoma, rectum adenocarcinoma, sarcoma, skin cutaneous melanoma, stomach adenocarcinoma, testicular germ cell tumors, thyroid carcinoma, thymoma, uterine carcinosarcoma, uveal melanoma. Other examples include breast cancer, lung cancer, lymphoma, melanoma, liver cancer, colorectal cancer, ovarian cancer, bladder cancer, renal cancer or gastric cancer. Further examples of cancer include neuroendocrine cancer, non-small cell lung cancer (NSCLC), small cell lung cancer, thyroid cancer, endometrial cancer, biliary cancer, esophageal cancer, anal cancer, salivary, cancer, vulvar cancer or cervical cancer.

The term "tumor" refers to all neoplastic cell growth and proliferation, whether malignant or benign, and all pre-cancerous and cancerous cells and tissues. The terms "cancer," "cancerous," "cell proliferative disorder," "proliferative disorder" and "tumor" are not mutually exclusive as referred to herein.

As used in this Specification and the appended claims, the singular forms "a," "an" and "the" include plural referents unless the context clearly dictates otherwise.

Unless specifically stated or obvious from context, as used herein, the term "or" is understood to be inclusive and covers both "or" and "and".

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Derivation of the PRRT Predictive Quotient (PPQ): An 8-Marker Gene Panel Combined with Grade The PRRT predictive quotient (PPQ) comprises expression of genes involved in growth factor expression/metabolism (Table 2) and tissue grade. It provides two biomarker outputs—"positive" (or predict responder) and "negative" (or predict non-responder). The model was developed from an initial cohort of 54 patients and then clinically validated in four separate cohorts (n=214).

PANK2 and PLD3) and optionally genes involved in proliferation (P) (NAP1L1, NOL3, and TECPR2). Expression levels were normalized to ALG9. In some embodiments, summated GF+M values ≥5.9 are scored "1", values <5.9 are "0". In some embodiments, summated GF+M+P values ≥10.9 are scored "1", values <10.9 are "0". From tissue histology, low grade (G1/G2, well-differentiated, or bronchial typical or atypical carcinoid) are scored "0"; high grade (G3, poorly differentiated) are scored "1". The logistic regression classification was used to combine these data into a prediction model with the generation of a score for each sample. The PPQ of a sample was derived from:

PPQ=39.22787−40.80341*(summated GF+$M$ gene expression)−18.441*(grade) or

PPQ=39.22787−40.80341*(summated GF+$M$+$P$ gene expression)−18.441*(grade)

A binary output could be generated from the model.

(1) Responder refers to individuals predicted by the PPQ as achieving disease stabilization or demonstrating a partial response. These are scored as biomarker "positive" and exhibit p-values <0.5.

TABLE 2

| GEP-NEN Biomarker or Housekeeping Gene | | NCBI Chromosome location | UniGene | | Amplicon produced using forward and reverse primers | Exon |
|---|---|---|---|---|---|---|
| Symbol | Name | [Cytogenetic band] | ID | RefSeq | Length (bp) | Boundary |
| ALG9 (Housekeeping Gene) | asparagine-linked glycosylation 9, alpha-1,2-mannosyltransferase homolog | Chr. 11 - 111652919-111742305 [11q23.1] | Hs.503850 | NM_024740.2 | 68 | 4-5 |
| ARAF1 | v-raf murine sarcoma 3611 viral oncogene homolog | Chr. X - 47420578-47431320 [Xp11.3] | Hs.446641 | NM_001654.3 | 74 | 10-11 |
| ATP6V1H | ATPase, H+ transporting, lysosomal 50/57 kDa, V1, Subunit H | Chr.8: 54628115-54755850 [8q11.23] | Hs.491737 | NM_015941 | 102 | 13-14 |
| BRAF | v-raf murine sarcoma viral oncogene homolog B1 | Chr. 7 - 140433812-140624564 [7q34] | Hs.550061 | NM_004333.4 | 77 | 1-2 |
| KRAS | v-Ki-ras2 Kirsten rat sarcoma viral oncogene homolog | Chr. 12 - 25358180-25403854 [12p12.1] | Hs.505033 | NM_004985.3 | 130 | 4-5 |
| NAP1L1 | nucleosome assembly protein 1-like 1 | Chr. 12 - 76438672-76478738 [12q21.2] | Hs.524599 | NM_139207.2 | 133 | 1-2 |
| NOL3 | nucleolar protein 3 (apoptosis repressor with CARD domain), transcript variant 3 | Chr. 16: 67204405-67209643 [16q22.1] | Hs.513667 | NM_001185057 | 118 | 1-2 |
| OAZ2 | ornithine decarboxylase antizyme 2 | Chr. 15: 64979773-64995462 [15q22.31] | Hs.713816 | NM_002537 | 96 | 1-2 |
| PANK2 | pantothenate kinase 2 | Chr.20: 3869486-3904502 [20p13] | Hs.516859 | NM_024960 | 126 | 4-5 |
| PLD3 | phospholipase D family, member 3, transcript variant 1 | Chr.19: 40854332-40884390 [19q13.2] | Hs.257008 | NM_001031696 | 104 | 6-7 |
| RAF1 | v-raf-1 murine leukemia viral oncogene homolog 1 | Chr. 3 - 12625100-12705700 [3p25.2] | Hs.159130 | NM_002880.3 | 90 | 7-8 |
| TECPR2 | tectonin beta-propeller repeat containing 2, transcript variant 2 | Chr. 14: 102829300-102968818 [14q32.31] | Hs. 195667 | NM_001172631 | 61 | 12-13 |

A two-step protocol (RNA isolation, cDNA production and PCR) is used to measure expression of growth factor (GF)-related genes (ARAF1, BRAF, KRAS and RAF-1), genes involved in metabolism (M) (ATP6V1H, OAZ2, (2) A non-responder was defined as an individual exhibiting progressive disease at the time of follow-up (PRRT failure). These are considered biomarker "negative" and exhibit p-values ≥0.5.

Five examples of the output are provided in Table 3.

TABLE 3

These are examples of output from the Algorithm

| Sample # | GF Signalome* | Metabolome** | Proliferome*** | Summated expression (GF + M) | Summated expression (GF + M + P) | GEP Score | Histology Grade<sup>&</sup> | Grade Score | Logistic Regression | p-value$ | PPQ Classifier# |
|---|---|---|---|---|---|---|---|---|---|---|---|
| 1 | 41.5 | 25.7 | 10.2 | 67.24 | 77.44 | 1 | G1 | 0 | −1.57554 | 0.0258 | R |
| 2 | 17.92 | 5.40 | 3.1 | 23.32 | 26.42 | 1 | G3 | 1 | −20.0165 | $9.36 \times 10^{-21}$ | R |
| 3 | 6.33 | 2.07 | 14.8 | 8.405 | 23.205 | 1 | Typical carcinoid (lung) | 0 | −1.57554 | 0.0258 | R |
| 4 | 3.93 | 1.94 | 2.1 | 5.87 | 7.97 | 0 | G1 | 0 | 39.22787 | 1.0 | NR |
| 5 | 3.14 | 1.41 | 4.3 | 4.56 | 8.86 | 0 | 1 | 1 | 20.78687 | 1.0 | NR |

*Normalized gene expression of ARAF1, BRAF, KRAS and RAF-1;
**Normalized gene expression of APT61VH, OAZ2, PANK2, and PLD3;
***Normalized gene expression of NAP1L1, NOL3, and TECPR2;
<sup>&</sup>Low grade (G1/G2, well-differentiated, or bronchial typical or atypical carcinoid); high grade (G3, poorly differentiated);
$Values > 0.5 are classified as non-responders; and
R = responder (PPQ-positive); NR = non-responder (PPQ-negative).

This model has the following metrics: $Chi^2=41.6$, DF=2, p<0.00001, Cox & Snell $R^2=0.537$, Nagelkerke $R^2=0.722$.

The accuracy of the classifier is 94% in the test population. This included: 97% responders and 91% non-responders.

This cohort was increased to 72 patients. The PPQ accurately predicted responders at initial (100%) and final (100%) follow-up (Table 4). Non-responders were predicted in 65% (initial) and 84% (final) (Fishers, p=NS). Overall, at the final follow-up, 67/72 (93%) were correctly predicted. PRRT-responders were predicted in 100% and non-responders in 84% of cases (Table 4). An evaluation of progression-free survival identified that in responders predicted by PPQ, the mPFS was not reached. For those predicted not to respond, the mPFS was 8 months. This was significantly different (HR 36.4, p<0.0001) (FIG. 1). The sensitivity of the test was 100%, the NPV was 100%.

TABLE 4

Predictive Accuracy of PPQ in the PRRT-treated cohorts

| | FOLLOW-UP* (AFTER PRRT) | | OVERALL | | | | |
|---|---|---|---|---|---|---|---|
| | R | NR | (R + NR) | Se** | Sp** | PPV** | NPV** |
| TEST COHORT (n = 72) | 41/41 (100%) | 26/31 (84%) | 67/72 (93%) | 100% | 84% | 89% | 100% |
| VALIDATION COHORT I (n = 44) | 28/29 (97%) | 14/15 (93%) | 42/44 (95%) | 97% | 93% | 97% | 93% |
| VALIDATION COHORT II (n = 42) | 30/32 (94%) | 10/10 (100%) | 40/42 (95%) | 94% | 100% | 100% | 83% |
| OVERALL (n = 158) | 99/102 (97%) | 50/56 (89%) | 149/158 (94%) | 97% | 89% | 94% | 94% |

PRRT-responders were predicted in 100% and non-responders in 84% of cases (Table 4). An evaluation of progression-free survival identified that in responders predicted by PPQ, the mPFS was not reached. For those predicted not to respond, the mPFS was 8 months. This was significantly different (HR 36.4, p<0.0001) (FIG. 1). The sensitivity of the test was 100%, the NPV was 100%.

This model has the following metrics: $Chi^2=41.6$, DF=2, p<0.00001, Cox & Snell $R^2=0.537$, Nagelkerke $R^2=0.722$.

The accuracy of the classifier is 94% in the test population. This included: 97% responders and 91% non-responders.

In Table 4, *Follow-up was ~6-9 months after the end of the last PRRT cycle; **Se=sensitivity, Sp=specificity, PPV=positive predictive value, NPV=negative predictive value.

Predicting Response to PRRT

Figure 2:
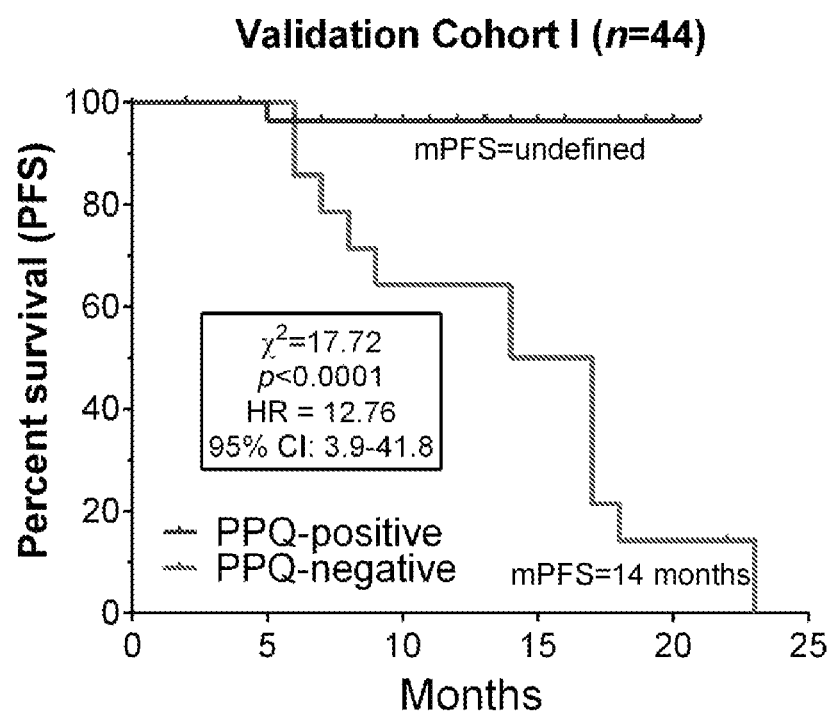
FIG. 2 is a graph showing the utility of the PRRT Prediction Quotient for predicting PFS in Validation Cohort I. The mPFS was not reached in those predicted to respond. In those predicted not to respond, the mPFS was 14 months (HR 17.7, p<0.0001).

Validation I (n=44): The PPQ accurately predicted responders in 97% at follow-up. Non-responders were predicted in 93% (final). Overall, 42/44 (95%) were correctly predicted (Table 4). An evaluation of survival identified the mPFS was not reached in those predicted to respond. For "non-responders", the mPFS was 14 months (HR 17.7, p<0.0001) (FIG. 2). The sensitivity of the test was 97%, the NPV was 93%.

Figure 3:
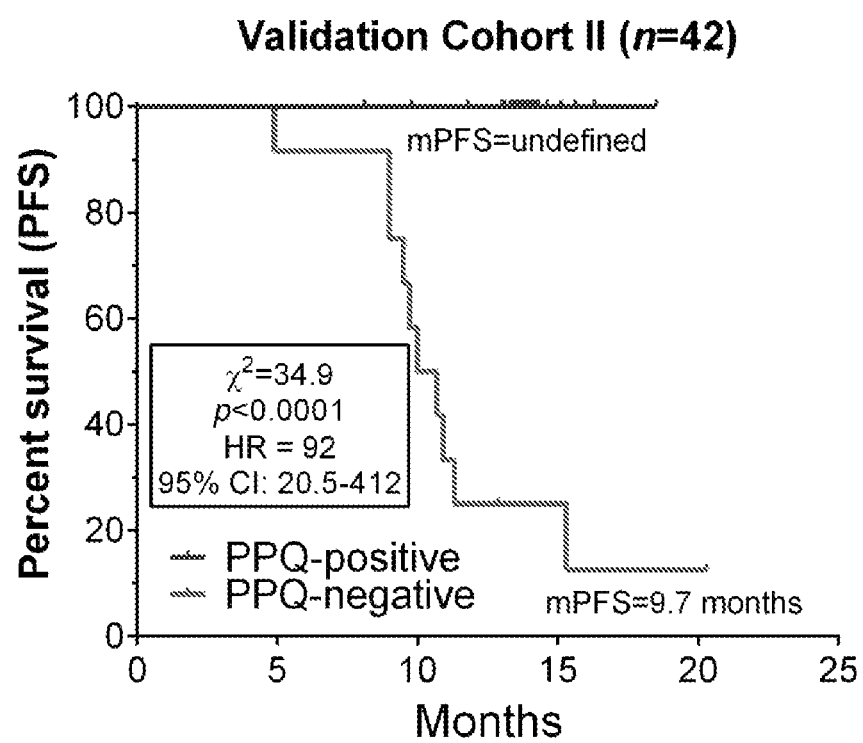
FIG. 3 is a graph showing the utility of the PRRT Prediction Quotient for predicting PFS in Validation Cohort II. In prediction-responders, the mPFS was not reached. For those predicted not to respond, the mPFS was 9.7 months. This was significantly different (HR 92, p<0.0001).

Validation II (n=42): The PPQ accurately predicted responders in 94% at follow-up. Non-responders were predicted in 100%. Overall, at the final follow-up, 40/42 (95%) were correctly predicted. PRRT-responders were predicted in 95% and non-responders in 100% (Table 4). An evaluation of survival identified the mPFS was not reached in those predicted to respond. For "non-responders", the mPFS was 9.7 months (HR 92, p<0.0001) (FIG. 3). The sensitivity of the test was 94%, the NPV was 95%.

Specificity of PPQ—Predicting Response to Non-Radioactive Somatostatin

Figure 4:
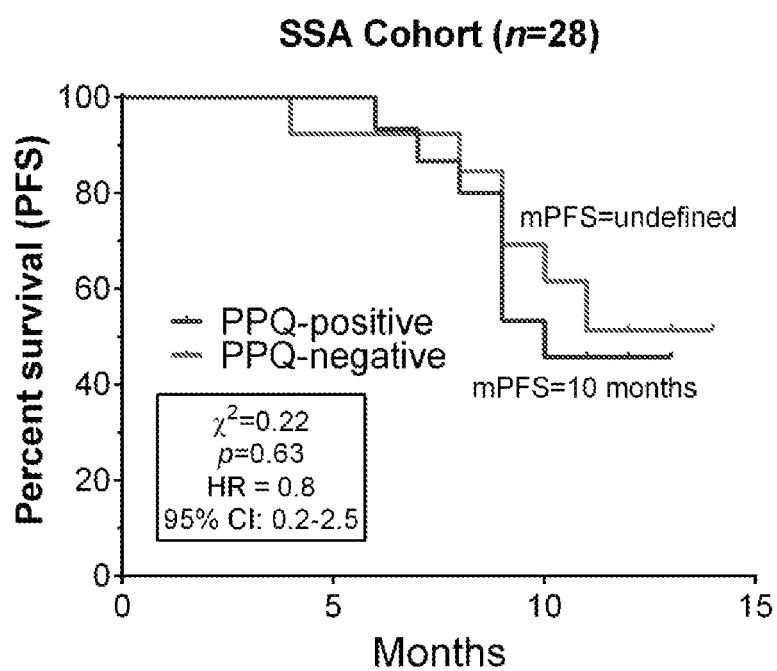
FIG. 4 is a graph showing the utility of the PRRT prediction quotient for predicting PFS in SSA treated patients. In prediction-responders, the mPFS was 10 months. For those predicted not to respond, the mPFS was not reached. This was not significantly different (HR 0.8, p=NS).

The PPQ was retrospectively determined in 28 patients treated only with SSAs. At follow-up, 15 (54%) were stable and 13 (46%) had developed progressive disease. The PPQ correctly predicted disease stabilization in 8 (53%) and progressive disease in 6 (47%, p=NS). Survival analysis identified no impact on PFS (FIG. 4). The sensitivity and NPV were 53% and 46%, respectively. The PPQ did not predict response to SSA.

Specificity of PPQ—Function as a Prognostic Marker

Figure 5:
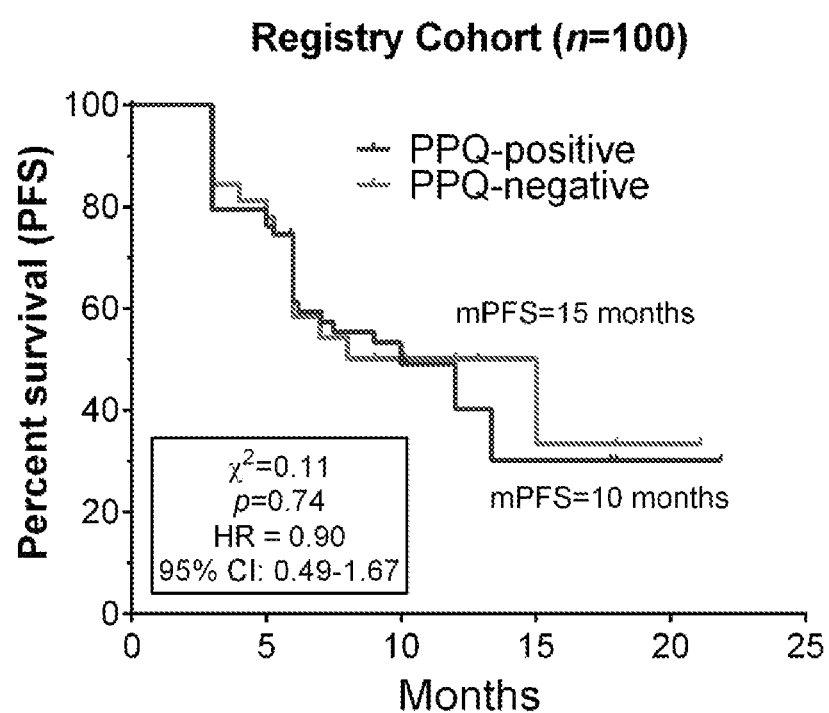
FIG. 5 is a graph showing the utility of the PRRT Prediction Quotient for predicting PFS in Registry-enrolled patients. In prediction-responders, the mPFS was 10 months. For those predicted not to respond, the mPFS was 15. This was not significantly different (HR 0.9, p=NS).

The PPQ was retrospectively determined in 100 patients included in a Registry. Analysis was undertaken on the group as a whole irrespective of treatment. At follow-up, 48 (48%) were stable and 52 (52%) had developed progressive disease. The PPQ correctly predicted disease stabilization in 32 (67%) and progressive disease in 19 (37%, p=NS). Survival analysis identified no impact on PFS (FIG. 5). The sensitivity and NPV were 67% and 50%. The PPQ did not function as a prognostic biomarker over the follow-up time-period.

Demonstrating Predictive Utility for PRRT

To demonstrate a biomarker is predictive of treatment, studies should evaluate biomarker levels those in whom a treatment benefit is expected as well as in those not treated with the agent. Because biomarkers may have both predictive and prognostic features, the association between a biomarker and outcome, regardless of treatment, are required to be evaluated.

Figure 6A:
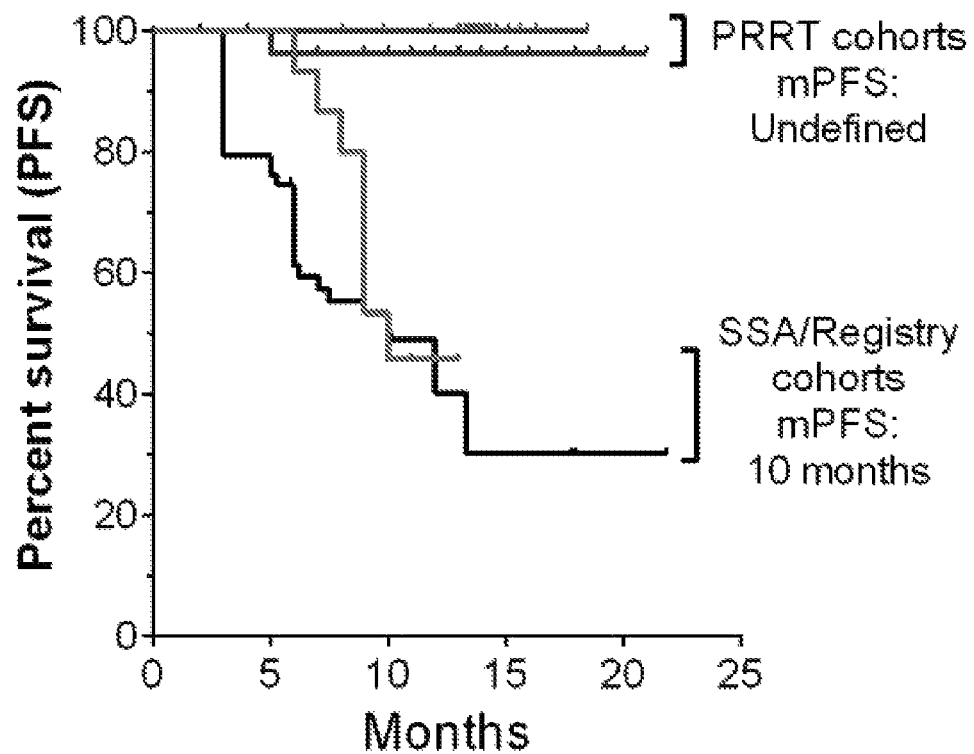
FIGS. 6A-6D are graphs showing demonstration of utility of the PPQ as a predictive marker.
Figure 6B:
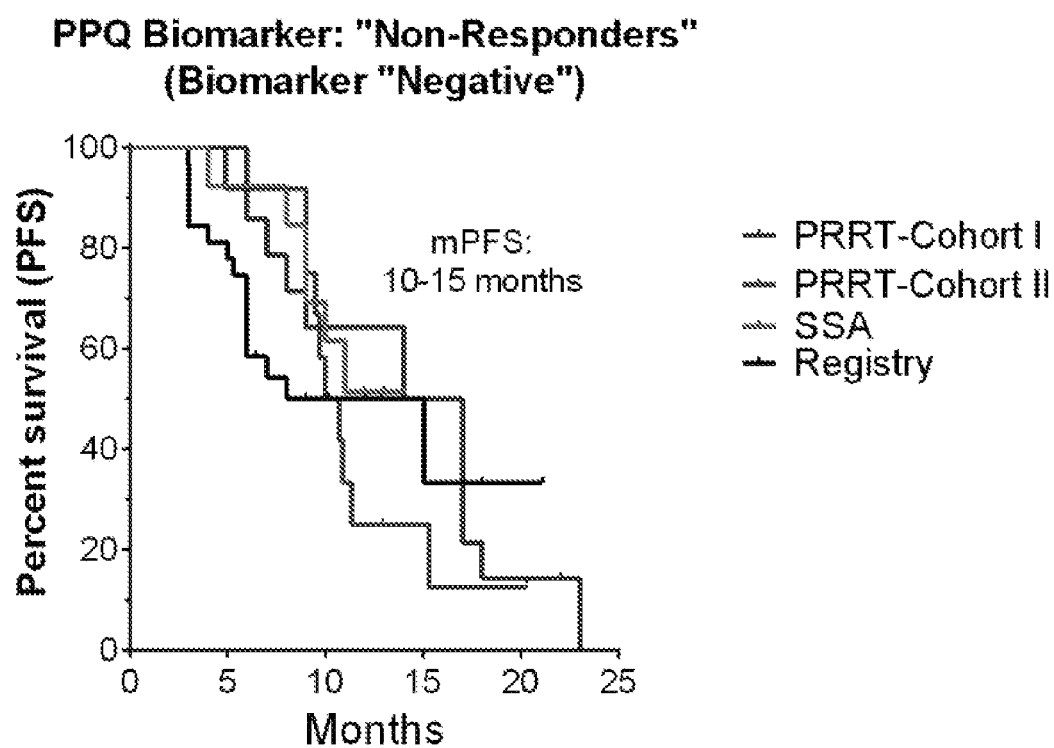

A comparison of the Kaplan-Meier survival curves (PFS) between each of these cohorts is represented in FIG. 6A (predicting "responders") and FIG. 6B (predicting "non-responders"). A "treatment effect" was only noted in those who were biomarker "positive" i.e., predicted to be a "responder" and undergoing PRRT (Validation I and Validation II cohorts). Specifically, a quantitative difference (statistically significant, p<0.0001) was noted in median PFS between the PRRT- and non-PRRT-treated groups. This effect occurred irrespective of whether they were all biomarker "positive". In contrast, no difference in PFS was noted in the biomarker "negative" group. This effect was noted irrespective of treatment. These data demonstrate that the PPQ functions as a predictive marker.

Figure 6C:
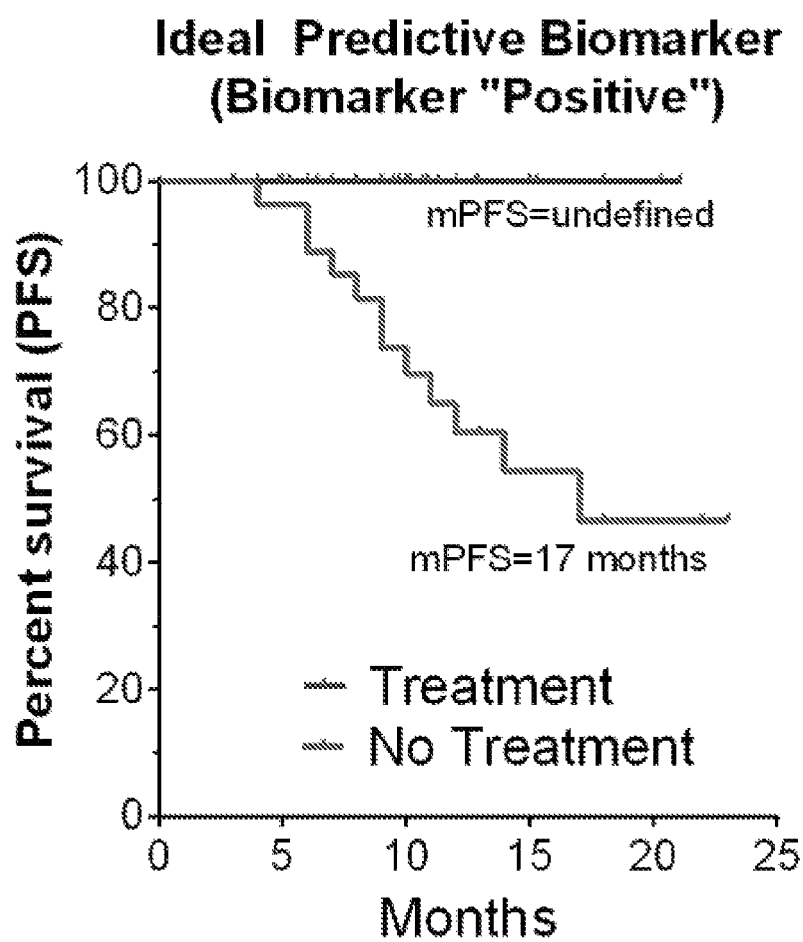
Figure 6D:
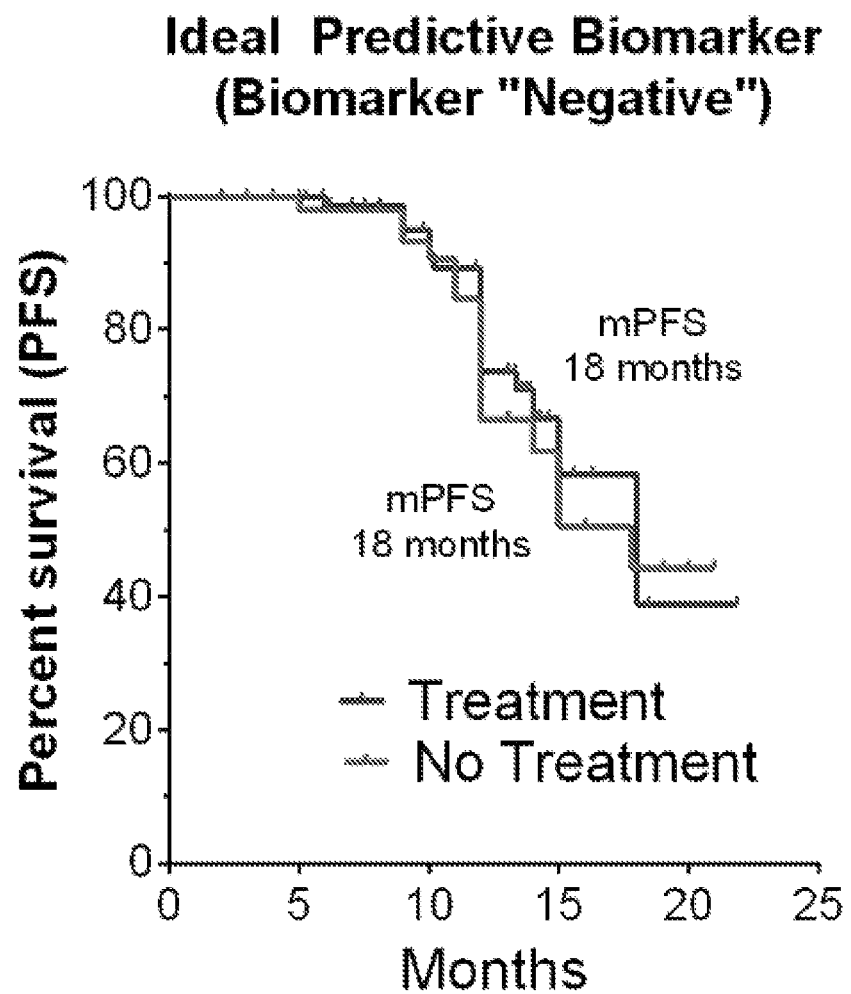

The metrics for an idealized biomarker are included in FIGS. 6C-D. The treatment effect was only noted in those who were treated and were PPQ biomarker "positive" (FIG. 6C—these are the two validation cohorts). It is important to highlight that this particular example identifies the idealized biomarker is not prognostic. This is highlighted by the similar survival curves in the biomarker positive and negative group in the absence. A comparison of FIG. 6A (Biomarker positive) identify that the survival curves of the SSA-treated cohort and the Registry cohort (both not treated with PRRT—10 months) are the not different from the survival curves of the PRRT-treated cohorts in FIG. 6B (Biomarker negative—survival 10-15 months) confirm that the PPQ is not prognostic.

Evaluation of PPQ-Negative Patients

Figure 7:
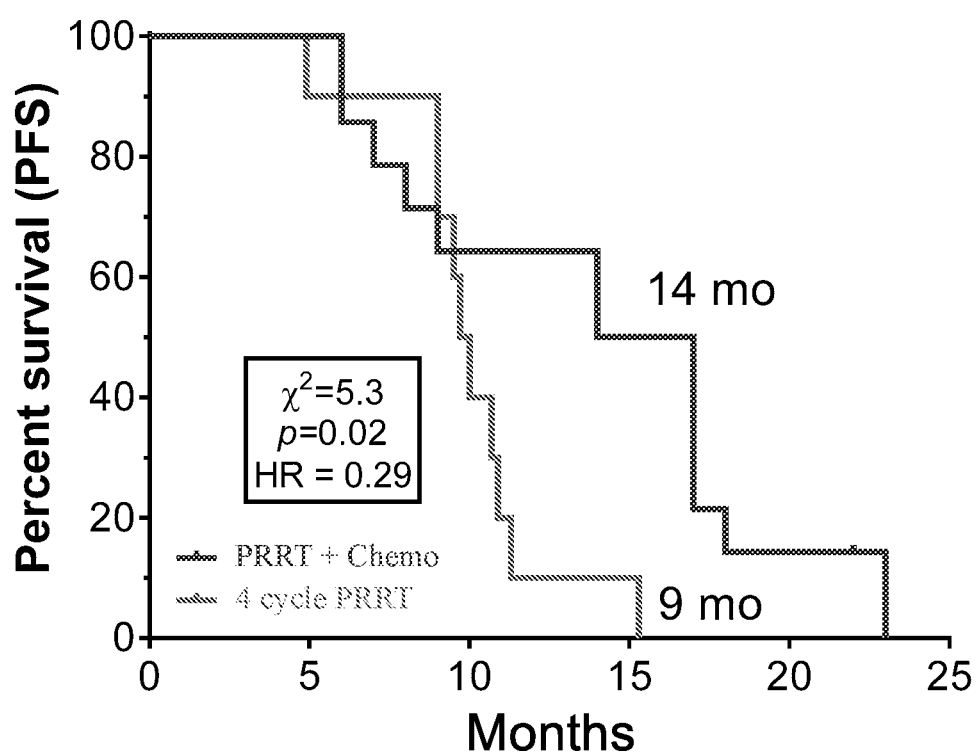
FIG. 7 shows the progression-free survival (PFS) of PPQ negative subjects after treatment with PRRT or a combination of PRRT and chemotherapy.

Clinical outcomes of patients that were identified by the PPQ to be a predicted non-responder to PRRT therapy were further analyzed. The PPQ predicted non responders that were treated with the standard 4 cycle PRRT of Lutathera exhibited a median PFS of 9 months, as shown in FIG. 7. Conversely, PPQ predicted non responders that underwent a personalized approach where chemotherapy was added to the protocol exhibited a longer PFS of 14 months, as shown in FIG. 7. These data demonstrate that patients with a PPQ-negative (predicted non-responder) and who have additional therapies will respond better than those on standard therapy. Thus, the PPQ can be used to identify patients that require additional agents (e.g. immune-related treatments or chemotherapy) to be used with PRRT and thereby optimize outcomes.

REFERENCES

1. Bodei L, Kwekkeboom D J, Kidd M, Modlin I M, Krenning E P. Radiolabeled Somatostatin Analogue Therapy Of Gastroenteropancreatic Cancer. Semin Nucl Med. 2016; 46: 225-238. doi: 210.1053/j.semnuclmed.2015.1012.1003.
2. Reubi J C, Laissue J, Waser B, Horisberger U, Schaer J C. Expression of somatostatin receptors in normal, inflamed, and neoplastic human gastrointestinal tissues. Ann N Y Acad Sci. 1994; 733: 122-137.
3. Bodei L, Kwekkeboom D J, Kidd M, Modlin I M, Krenning E P. Radiolabeled Somatostatin Analogue Therapy Of Gastroenteropancreatic Cancer. Semin Nucl Med. 2016; 46: 225-238.
4. Cives M, Strosberg J. Radionuclide Therapy for Neuroendocrine Tumors. Curr Oncol Rep. 2017; 19: 9.
5. Brabander T, van der Zwan W A, Teunissen J J M, et al. Long-Term Efficacy, Survival, and Safety of [177Lu-DOTAO,Tyr3]octreotate in Patients with Gastroenteropancreatic and Bronchial Neuroendocrine Tumors. Clin Cancer Res. 2017; 23: 4617-4624.
6. Sansovini M, Severi S, Ambrosetti A, et al. Treatment with the radiolabelled somatostatin analog Lu-DOTATATE for advanced pancreatic neuroendocrine tumors. Neuroendocrinology. 2013; 97: 347-354. doi: 310.1159/000348394. Epub 000342013 May 000348322.
7. Ezziddin S, Khalaf F, Vanezi M, et al. Outcome of peptide receptor radionuclide therapy with 177Lu-octreotate in advanced grade 1/2 pancreatic neuroendocrine tumours. Eur J Nucl Med Mol Imaging. 2014; 41: 925-933.
8. Mariniello A, Bodei L, Tinelli C, et al. Long-term results of PRRT in advanced bronchopulmonary carcinoid. Eur J Nucl Med Mol Imaging. 2016; 43: 441-452.
9. Strosberg J, El-Haddad G, Wolin E, et al. Phase 3 Trial of 177Lu-Dotatate for Midgut Neuroendocrine Tumors. N Engl J Med. 2017; 376: 125-135.
10. Kwekkeboom D J, Kam B L, van Essen M, et al. Somatostatin-receptor-based imaging and therapy of gastroenteropancreatic neuroendocrine tumors. Endocr Relat Cancer. 2010; 17: R53-73.
11. Charoenpitakchai M, Liu E, Zhao Z, et al. In liver metastases from small intestinal neuroendocrine tumors, SSTR2A expression is heterogeneous. Virchows Arch. 2017; 470: 545-552.
12. Oksuz M O, Winter L, Pfannenberg C, et al. Peptide receptor radionuclide therapy of neuroendocrine tumors with (90)Y-DOTATOC: is treatment response predictable by pretherapeutic uptake of (68)Ga-DOTATOC? Diagn Intery Imaging. 2014; 95: 289-300.

13. Gabriel M, Oberauer A, Dobrozemsky G, et al. 68Ga-DOTA-Tyr3-octreotide PET for assessing response to somatostatin-receptor-mediated radionuclide therapy. J Nucl Med. 2009; 50: 1427-1434.
14. Blaickner M, Baum R P. Relevance of PET for pretherapeutic prediction of doses in peptide receptor radionuclide therapy. PET Clin. 2014; 9: 99-112.
15. Oberg K, Krenning E, Sundin A, et al. A Delphic consensus assessment: imaging and biomarkers in gastroenteropancreatic neuroendocrine tumor disease management. Endocr Connect. 2016; 5: 174-187.
16. Yang Z, Tang L H, Klimstra D S. Effect of Tumor Heterogeneity on the Assessment of Ki67 Labeling Index in Well-differentiated Neuroendocrine Tumors Metastatic to the Liver: Implications for Prognostic Stratification. Am J Surg Pathol. 2011; 35: 853-860.
17. Ezziddin S, Attassi M, Yong-Hing C J, et al. Predictors of long-term outcome in patients with well-differentiated gastroenteropancreatic neuroendocrine tumors after peptide receptor radionuclide therapy with 177Lu-octreotate. J Nucl Med. 2014; 55: 183-190. doi: 110.2967/jnumed.2113.125336. Epub 122014 Jan 125316.
18. Thang S P, Lung M S, Kong G, et al. Peptide receptor radionuclide therapy (PRRT) in European Neuroendocrine Tumour Society (ENETS) grade 3 (G3) neuroendocrine neoplasia (NEN)—a single-institution retrospective analysis. Eur J Nucl Med Mol Imaging. 2017; 12: 017-3821.
19. Walenkamp A, Crespo G, Fierro Maya F, et al. Hallmarks of gastrointestinal neuroendocrine tumours: implications for treatment. Endocr Relat Cancer. 2014; 21: R445-460. doi: 410.1530/ERC-1514-0106.
20. Wang E, Zaman N, McGee S, Milanese J S, Masoudi-Nejad A, O'Connor-McCourt M. Predictive genomics: A cancer hallmark network framework for predicting tumor clinical phenotypes using genome sequencing data. Semin Cancer Biol. 2014; 18: 00050-00059.
21. Oxnard G R, Paweletz C P, Kuang Y, et al. Noninvasive detection of response and resistance in EGFR-mutant lung cancer using quantitative next-generation genotyping of cell-free plasma DNA. Clin Cancer Res. 2014; 20: 1698-1705. doi: 1610.1158/1078-0432.CCR-1613-2482. Epub 2014 January 1615.
22. Kidd M, Drozdov I, Modlin I. Blood and tissue neuroendocrine tumor gene cluster analysis correlate, define hallmarks and predict disease status. Endocr Relat Cancer. 2015; 22: 561-575. doi: 510.1530/ERC-1515-0092. Epub 2015 June 1532.
23. Li S C, Essaghir A, Martijn C, et al. Global microRNA profiling of well-differentiated small intestinal neuroendocrine tumors. Mod Pathol. 2013; 26: 685-696. doi: 610.1038/modpathol.2012.1216. Epub 2013 January 1018.
24. Modlin I, Drozdov I, Kidd M. The Identification of gut neuroendocrine tumor disease by multiple synchronous transcript analysis in blood. Plos One. 2013; e63364.
25. Bodei L, Kidd M, Modlin I M, et al. Measurement of circulating transcripts and gene cluster analysis predicts and defines therapeutic efficacy of peptide receptor radionuclide therapy (PRRT) in neuroendocrine tumors. Eur J Nucl Med Mol Imaging. 2016; 43: 839-851. doi: 810.1007/s00259-00015-03250-z. Epub 02015 November 00223.
26. Califano A, Alvarez M J. The recurrent architecture of tumour initiation, progression and drug sensitivity. Nat Rev Cancer. 2017; 17: 116-130. doi: 110.1038/nrc.2016.1124. Epub 2016 December 1015.
27. Trusheim M R, Berndt E R. The clinical benefits, ethics, and economics of stratified medicine and companion diagnostics. Drug Discov Today. 2015; 20: 1439-1450. doi: 1410.1016/j.drudis.2015.1410.1017. Epub 2015 November 1433.
28. Modlin I, Drozdov I, Alaimo D, et al. A multianalyte PCR blood test outperforms single analyte ELISAs for neuroendocrine tumor detection Endocr Relat Cancer. 2014; 21: 615-628.
29. Li X J, Hayward C, Fong P Y, et al. A blood-based proteomic classifier for the molecular characterization of pulmonary nodules. Sci Transl Med. 2013; 5: 207ra142. doi: 210.1126/scitranslmed.3007013.
30. Kaijser J, Sayasneh A, Van Hoorde K, et al. Presurgical diagnosis of adnexal tumours using mathematical models and scoring systems: a systematic review and meta-analysis. Hum Reprod Update. 2014; 20: 449-462. doi: 410.1093/humupd/dmt1059. Epub 2013 December 1099.
31. Risch H A, Lu L, Streicher S A, et al. Aspirin Use and Reduced Risk of Pancreatic Cancer. Cancer Epidemiol Biomarkers Prev. 2017; 26: 68-74. doi: 10.1158/1055-9965.EPI-1116-0508. Epub 2016 December 1120.
32. Ballman K V. Biomarker: Predictive or Prognostic? J Clin Oncol. 2015; 33: 3968-3971. doi: 3910.1200/JCO.2015.3963.3651. Epub 2015 September 3921.
33. Pritzker K P. Predictive and prognostic cancer biomarkers revisited. Expert Rev Mol Diagn. 2015; 15: 971-974. doi: 910.1586/14737159.14732015.11063421. Epub 14732015 July 14737151.

EQUIVALENTS

While the present invention has been described in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A method of treating a subject with peptide receptor radiotherapy (PRRT), wherein the subject has a neuroendocrine tumor (NET), the method comprising:
    determining the expression level of at least 12 biomarkers from a test sample from the subject by contacting the test sample with a plurality of agents specific to detect the expression of the at least 12 biomarkers, wherein the 12 biomarkers comprise ARAF1, BRAF, KRAS, RAF-1, ATP6V1H, OAZ2, PANK2, PLD3, NAP1L1, NOL3, TECPR2, and ALG9;
    normalizing the expression level of each of ARAF1, BRAF, KRAS, RAF-1, ATP6V1H, OAZ2, PANK2, PLD3, NAP1L1, NOL3, and TECPR2 to the expression level of ALG9, thereby obtaining a normalized expression level of each of ARAF1, BRAF, KRAS, RAF-1, ATP6V1H, OAZ2, PANK2, PLD3, NAP1L1, NOL3, and TECPR2;
    summing the normalized expression level of each of ARAF1, BRAF, KRAS, RAF-1, ATP6V1H, OAZ2, PANK2 PLD3, NAP1L1, NOL3, and TECPR2, thereby obtaining a summated expression level;
    determining a first score, wherein the first score is 1 when the summated expression level is equal to or greater than a first predetermined cutoff value, or the first score is 0 when the summated expression level is below the first predetermined cutoff value;

determining a second score based on the histological grade of the NET, wherein the second score is 1 when the NET is designated high grade, or the second score is 0 when the NET is designated low grade;

calculating a third score based on the following equation:

Third Score=39.22787−40.80341*(First Score)−18.441*(Second Score);

determining that the third score is equal to or greater than a second predetermined cutoff value, thereby identifying that the subject will be responsive to PRRT; and administering PRRT to the subject identified as being responsive to PRRT.

2. The method of claim 1, wherein the first predetermined cutoff value is 10.9.

3. The method of claim 1, wherein the second predetermined cutoff value is 0.

4. The method of claim 1, wherein at least one of the at least 12 biomarkers is RNA, cDNA, or protein.

5. The method of claim 4, wherein when the biomarker is RNA, the RNA is reverse transcribed to produce cDNA, and the produced cDNA expression level is detected.

6. The method of claim 1, wherein the test sample comprises blood, serum, plasma, neoplastic tissue or any combination thereof.

7. The method of claim 1, wherein the test sample comprises blood.

8. The method of claim 1, wherein the NET is designated high grade when the NET is poorly differentiated.

9. The method of claim 1, wherein the NET is designated low grade when the NET is well differentiated, bronchial typical carcinoid, or bronchial atypical carcinoid.

10. The method of claim 1, wherein administering PRRT to the subject comprises administering a $^{177}$Lu-based-PRRT.

11. The method of claim 10, wherein the $^{177}$Lu-based-PRRT is $^{177}$Lu-DOTA-Tyr$^3$-Thr$^8$-octreotide.

\* \* \* \* \*